(12) United States Patent
Elowitz et al.

(10) Patent No.: US 11,674,144 B2
(45) Date of Patent: Jun. 13, 2023

(54) FRACTIONAL REGULATION OF TRANSCRIPTION

(71) Applicant: California Institute of Technology, Pasadena, CA (US)

(72) Inventors: Michael Elowitz, Los Angeles, CA (US); Lacramioara Bintu, Pasadena, CA (US); John Yong, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 236 days.

(21) Appl. No.: 15/132,190

(22) Filed: Apr. 18, 2016

(65) Prior Publication Data
US 2016/0304872 A1    Oct. 20, 2016

Related U.S. Application Data

(60) Provisional application No. 62/148,366, filed on Apr. 16, 2015.

(51) Int. Cl.
| | | |
|---|---|---|
| *C12N 15/62* | (2006.01) | |
| *C12Q 1/68* | (2018.01) | |
| *C12N 5/071* | (2010.01) | |
| *C12N 15/63* | (2006.01) | |

(52) U.S. Cl.
CPC .................. *C12N 15/635* (2013.01)

(58) Field of Classification Search
None
See application file for complete search history.

(56) References Cited

U.S. PATENT DOCUMENTS

| | | | |
|---|---|---|---|
| 2002/0188103 A1* | 12/2002 | Bestor ....................... | C07K 7/06 530/350 |
| 2007/0142285 A1* | 6/2007 | Backs ............ | C12Y 305/01098 514/16.4 |
| 2014/0068797 A1* | 3/2014 | Doudna ............... | C12N 15/102 800/18 |
| 2016/0201089 A1* | 7/2016 | Gersbach ........... | A61K 48/0058 435/320.1 |
| 2019/0032049 A1* | 1/2019 | Naldini ................... | C12N 9/22 |

FOREIGN PATENT DOCUMENTS

| | | | | |
|---|---|---|---|---|
| WO | WO-2012143401 A1 | * | 10/2012 | ............. C12N 15/86 |

OTHER PUBLICATIONS

Vire et al. (2006) The Polycomb group protein EZH2 directly controls DNA methylation. Nature Letters, 439:871-824 (Year: 2006).*
Halford et al. (2004) How do site-specific DNA-binding proteins find their targets? Nucleic Acids Research, 32(10):3040-3052 (Year: 2004).*
Karapetyan et al. (2015) Role of DNA binding sites and slow unbinding kinetics in titration-based oscillators. Physical Review E, 92(062712), pp. 1-9 (Year: 2015).*
Velasco et al. (2010) Dnmt3b recruitment through E2F6 transcriptional repressor mediates germ-line gene silencing in murine somatic tissues. PNAS, 107(20):9281-9286 (Year: 2010).*
Thomas et al. (2005) HEK293 cell line: a vehicle for the expression of recombinant proteins. Journal of Pharmacological and Toxicological Methods, 51:187-200 (Year: 2005).*
Coulon et al. (2013) Eukaryotic transcriptional dynamics: from single molecules to cell populations. Nature Reviews Genetics, 14: 572-584 (Year: 2013).*
Si, Y. "Determination of the Causal Potential of Histone Modifications on Transcription and Chromatin Structure", Master of Science Thesis, University of Southern California, published by ProQuest, Aug. 2012, 51 pages (Year: 2012).*
Li et al. (2007) Chimeric DNA methyltransferases target DNA methylation to specific DNA sequences and repress expression of target genes. Nucleic Acids Research, 35(1):100-112 (Year: 2007).*
Urlinger et al. (2000) Exploring the sequence space for tetracycline dependent transcriptional activators: Novel mutations yield expanded range and sensitivity. PNAS, 97(14):7963-7968 (Year: 2000).*
Stolzenburg et al. (2015) Stable oncogenic silencing in vivo by programmable and targeted de novo DNA methylation in breast cancer. Oncogene, 34:5427-5435 (Year: 2015).*
Haynes and Silver, Synthetic Reversal of Epigenetic Silencing, JBC, 2011, pp. 27176-27182.*
Palmisano, Amino acid starvation induces reactivation of silenced transgenes and latent HIV-1 provirus via down-regulation of histone deacetylase 4 (HDAC4), PNAS, 2012, 2284-2293.*
Ayyanathan, Kasirajan et al.; "Regulated recruitment of HP1 to a euchromatic gene induces mitotically heritable, epigenetic gene silencing: a mammalian cell culture model of gene variegation"; Genes & Development; 17; 2003; pp. 1855-1869.
Biggar, Stephen R. et al.; "Cell signaling can direct either binary or graded transcriptional responses"; EMBO J.; vol. 20; No. 12; 2001; pp. 3167-3176.
Bintu, Lacramioara et al.; "Dynamics of epigenetic regulation at the single-cell level"; Science; Feb. 2016; vol. 351; Issue 6274; pp. 720-724.
Bintu, Lacramioara et al., Supplementary Material for "Dynamics of epigenetic regulation at the single-cell level," www.sciencemag.org/content/351/6274/720/suppl/DC1, Feb. 2016; vol. 351; pp. 1-29.
Bird, Adrian; "DNA methylation patterns and epigenetic memory"; Genes & Development; 16; pp. 6-21.
Blackledge, Neil P. et al.; "Variant PRC1 complex-dependent H2A ubiquitylation drives PRC2 recruitment and polycomb domain formation"; Cell; vol. 157; Issue 6; Jun. 5, 2014; pp. 1445-1459.

(Continued)

*Primary Examiner* — Maria Marvich
(74) *Attorney, Agent, or Firm* — Sheppard, Mullin, Richter & Hampton LLP

(57) ABSTRACT

A method of controlling the number of cells in a population of cells having silenced transcription of a target nucleic acid as a function of time includes recruiting a chromatin regulator (CR) to a site proximal to a transcription initiation site of the target nucleic acid to form a fraction of silenced cells in the population of cells. The chromatin regulator may be EED, KRAB, DNMT3, HDAC4, EZH2, REST, or a combination thereof.

17 Claims, 48 Drawing Sheets
(32 of 48 Drawing Sheet(s) Filed in Color)
Specification includes a Sequence Listing.

(56) References Cited

OTHER PUBLICATIONS

Blake, William J. et al.; "Noise in eukaryotic gene expression"; Nature; 422; Apr. 10, 2003; pp. 633-637.
Boros, Joanna et al.; "Polycomb repressive complex 2 and H3K27me3 cooperate with H3K9 methylation to maintain heterochromatin protein 1α at chromatin"; Mol. Cell. Biol.; vol. 34; No. 19; Oct. 2014; pp. 3662-3674.
Busslinger, Meinrad et al.; "Epigenetic control of immunity"; Cold Spring Harb. Perspect. Biol.; 6, Jun. 2, 2014; a019307.
Cai, Long et al.; "Stochastic protein expression in individual cells at the single molecule level"; Nature 440; Mar. 16, 2006; pp. 358-362.
Coulon, Antoine et al.; "Eukaryotic transcriptional dynamics: From single molecules to cell populations"; Nat. Rev. Genet.; 14; 2013; pp. 572-584.
Dodd, Ian B. et al.; "Theoretical analysis of epigenetic cell memory by nucleosome modification"; Cell; vol. 129; Issue 4; May 18, 2007; pp. 813-822.
Egger, Gerda et al.; "Epigenetics in human disease and prospects for epigenetic therapy"; Nature; 429; May 27, 2004; pp. 457-463.
Fraga, Mario F. et al.; "Epigenetics and aging: the targets and the marks"; Trends Genet.; Aug. 2007; vol. 23; Issue 8; pp. 413-418.
Friedman, Nir et al.; "Linking stochastic dynamics to population distribution: an analytical framework of gene expression"; Phys. Rev. Lett.; 97; Oct. 19, 2006; 168302.
Fussenegger, Martin et al.; "Streptogramin-based gene regulation systems for mammalian cells"; Nat. Biotechnol.; 18; 2000; pp. 1203-1208.
Gilbert, Luke A. et al.; "CRISPR-Mediated Modular RNA-Guided Regulation of Transcription in Eukaryotes"; Cell; vol. 154; Issue 2; Jul. 18, 2013; pp. 442-451.
Hansen, Klaus H. et al.; "A model for transmission of the H3K27me3 epigenetic mark"; Nat. Cell Biol.; 10; 2008; pp. 1291-1300.
Hathaway, Nathaniel A. et al.; "Dynamics and memory of heterochromatin in living cells"; Cell; 149; Jun. 22, 2012; pp. 1447-1460.
Jin, Bilian et al.; "DNA methylation: Superior or subordinate in the epigenetic hierarchy?"; Genes Cancer; vol. 2; Issue 6; 2011; pp. 607-617.
Katan-Khaykovich, Yael et al.; "Dynamics of global histone acetylation and deacetylation in vivo: Rapid restoration of normal histone acetylation status upon removal of activators and repressors"; Genes & Development; 16; 2002; pp. 743-752.
Keung, Albert J. et al.; "Chromatin regulation at the frontier of synthetic biology"; Nat. Rev. Genet.; 16; Feb. 10, 2015; pp. 159-171.
Keung, Albert J. et al.; "Using targeted chromatin regulators to engineer combinatorial and spatial transcriptional regulation"; Cell; vol. 158; Issue 1; Jul. 3, 2014; pp. 110-120.
Kouzarides, Tony; "Chromatin modifications and their function"; Cell; Feb. 23, 2007; 128; pp. 693-705.
Kringstein, Andrew M. et al.; "Graded transcriptional response to different concentrations of a single transactivator"; PNAS; vol. 95; No. 23; Nov. 1998; pp. 13670-13675.
Li, En et al.; "DNA methylation in mammals"; Cold Spring Harb. Perspect. Biol.; 6; May 1, 2014; a019133.
Li, Tao et al.; "CTCF Regulates Allelic Expression of Igf2 by Orchestrating a Promoter-Polycomb Repressive Complex 2 Intrachromosomal Loop"; Molecular and Cellular Biology; Oct. 2008; vol. 28; No. 20; pp. 6473-6482.
Lienert, Florian et al.; "Synthetic biology in mammalian cells: Next generation research tools and therapeutics"; Nat. Rev. Mol. Cell Biol.; Feb. 2014; 15(2); pp. 95-107.
Locke, James C.W. et al.; "Using movies to analyse gene circuit dynamics in single cells"; Nat. Rev. Microbiol.; 7; May 2009; pp. 383-392.

Maeder, Morgan L. et al.; "Targeted DNA demethylation and activation of endogenous genes using programmable TALE-TET1 fusion proteins"; Nat. Biotechnol.; 31; Oct. 9, 2013; pp. 1137-1142.
Margolin, Judith F. et al.; "Krüppel-associated boxes are potent transcriptional repression domains"; Proc. Natl. Acad. Sci.; vol. 91; No. 10; May 1994; pp. 4509-4513.
Margueron, Raphael et al.; "The Polycomb complex PRC2 and its mark in life"; Nature; 469; Jan. 20, 2011; pp. 343-349.
Miska, Eric A. et al.; "HDAC4 deacetylase associates with and represses the MEF2 transcription factor"; EMBO J.; vol. 18; 1999; pp. 5099-5107.
Okano, Masaki et al.; "DNA methyltransferases Dnmt3a and Dnmt3b are essential for De Novo Methylation and Mammalian Development"; Cell; vol. 99; Issue 3; Oct. 29, 1999; pp. 247-257.
Pasini, Diego et al.; "Coordinated regulation of transcriptional repression by the RBP2 H3K4 demethylase and Polycomb-Repressive Complex 2"; Genes Dev.; vol. 22; Issue 10; May 15, 2008; pp. 1345-1355.
Pasini, Diego et al.; "Characterization of an antagonistic switch between histone H3 lysine 27 methylation and acetylation in the transcriptional regulation of Polycomb group target genes"; Nucleic Acids Res.; vol. 38; No. 15; Apr. 12, 2010; pp. 4958-4969.
Pirrotta, Vincenzo et al.; "Epigenetic silencing mechanisms in budding yeast and fruit fly: Different paths, same destinations"; Mol. Cell; vol. 18; Issue 4; May 13, 2005; pp. 395-398.
Raser, Jonathan M. et al.; "Noise in gene expression: Origins, consequences, and control"; Science; vol. 309; Issue 5743; Sep. 23, 2005; pp. 2010-2013.
Rosenfeld, Nitzan et al.; "Gene Regulation at the Single-Cell Level"; Science; Mar. 25, 2005; vol. 307; Issue 5717; pp. 1962-1965.
Song, Jie et al.; "Vernalization—a cold-induced epigenetic switch"; J. Cell Sci.; 125; 2012; pp. 3723-3731.
Sprinzak, David et al.; "Cis Interactions between Notch and Delta Generate Mutually Exclusive Signaling States"; Nature; May 6, 2010; vol. 465; Issue 7294; pp. 86-90.
Stewart-Ornstein, Jacob et al.; "Msn2 coordinates a stoichiometric gene expression program"; Curr. Biol.; vol. 23; Issue 23; Dec. 2, 2013; pp. 2336-2345.
Sutherland, Heidi G.E. et al.; "Reactivation of heritably silenced gene expression in mice"; Mamm. Genome; vol. 11; Issue 5; May 2000; pp. 347-355.
Tay, Savas et al.; "Single-cell NF-κB dynamics reveal digital activation and analogue information processing"; Nature; 466; Jul. 8, 2010; pp. 267-271.
Urlinger, Stefanie et al.; "Exploring the sequence space for tetracycline-dependent transcriptional activators: Novel mutations yield expanded range and sensitivity"; PNAS; Jul. 5, 2000; vol. 97; No. 14; pp. 7963-7968.
Urrutia, Raul; "KRAB-containing zinc-finger repressor proteins"; Genome Biol.; 2003; 4:231; 8pp.
Wakabayashi-Ito, Noriko et al.; "Characterization of the regulatory elements in the promoter of the human elongation factor-1α gene"; J. Biol. Chem.; vol. 269; Nov. 25, 1994; pp. 29831-29837.
Weber, Wilfried et al.; "Macrolide-based transgene control in mammalian cells and mice"; Nat. Biotechnol.; 20; 2002; pp. 901-907.
Yamaguchi, Shigeyuki et al.; "A Method for Producing Transgenic Cells Using a Multi-Integrase System on a Human Artificial Chromosome Vector"; PLOS One; Feb. 24, 2011; vol. 6; Issue 2; e17267; 11pp.
Yusufzai, Timur M. et al.; "The 5'-HS4 chicken β-globin insulator is a CTCF-dependent nuclear matrix-associated element"; PNAS; Jun. 8, 2004; vol. 101; No. 23; pp. 8620-8624.
Zhou, Vicky W. et al.; "Charting histone modifications and the functional organization of mammalian genomes"; Nat. Rev. Genet.; 12; 7-18; Jul. 2011.
Zhu, Jiang et al.; "Genome-wide chromatin state transitions associated with developmental and environmental cues"; Cell; 152; Jan. 31, 2013; pp. 642-654.

* cited by examiner

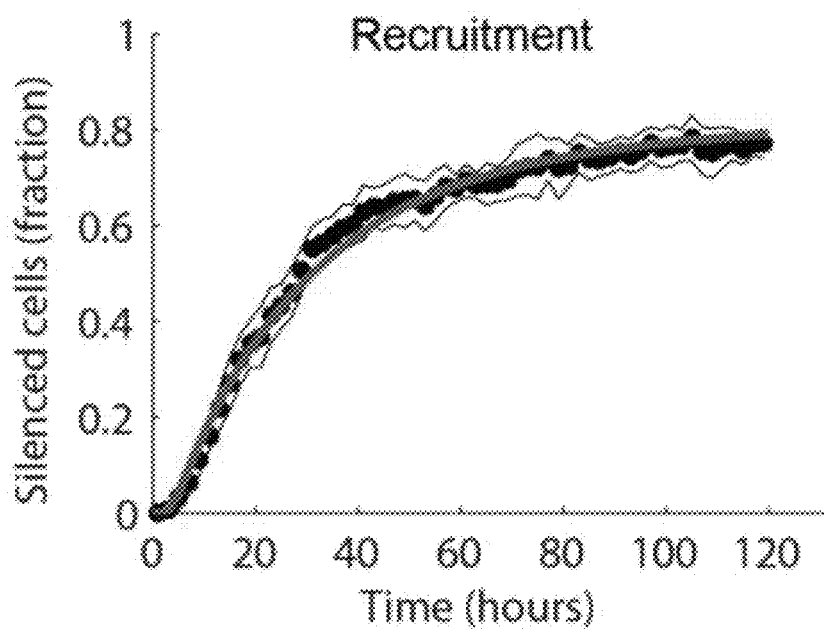
FIG. 14D
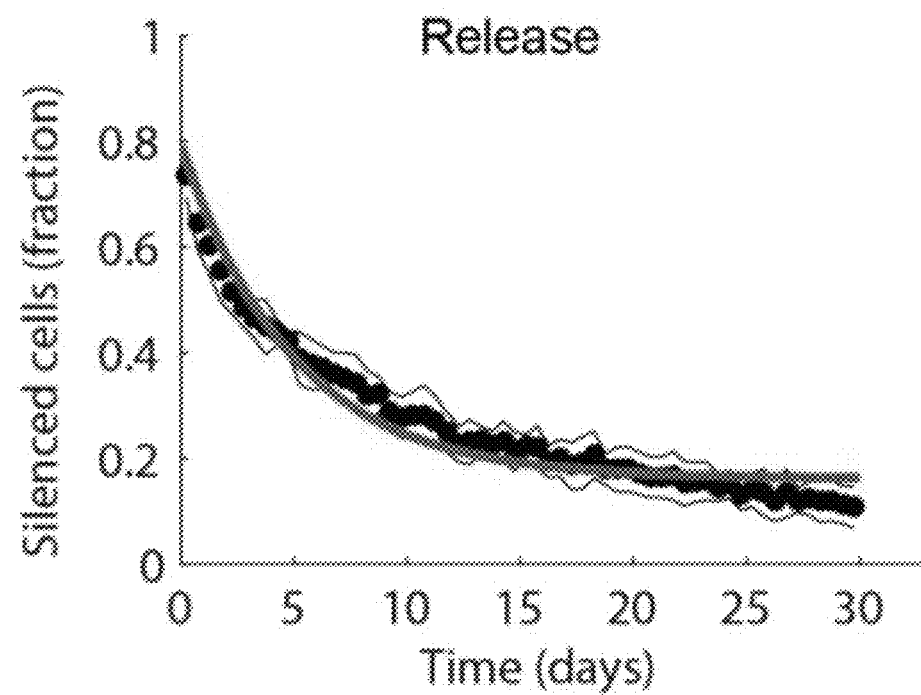

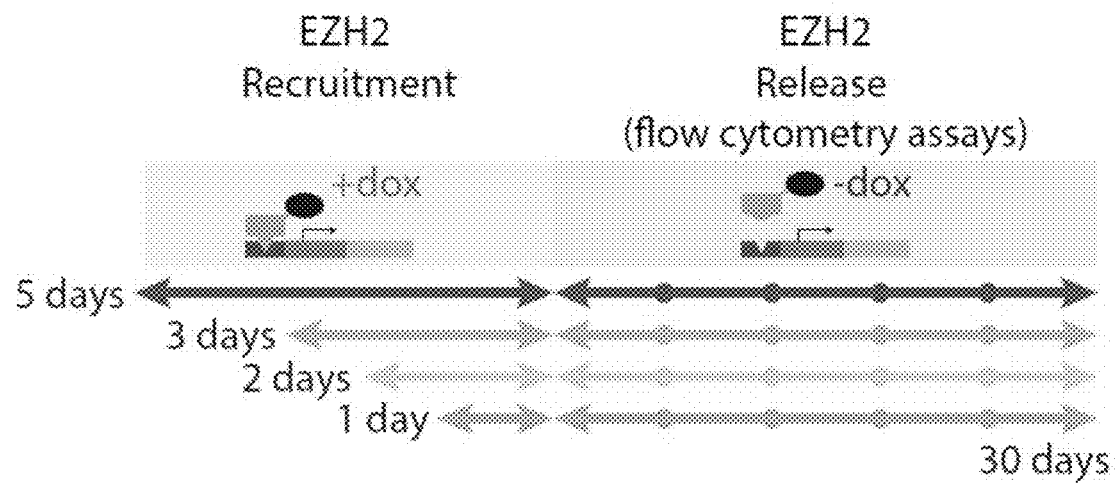
FIG. 17B
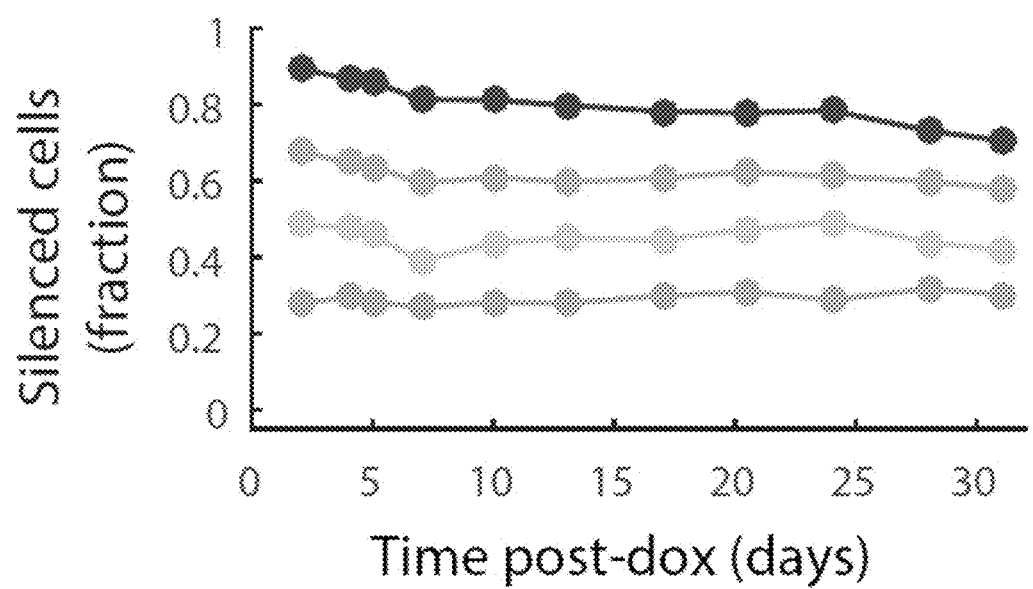

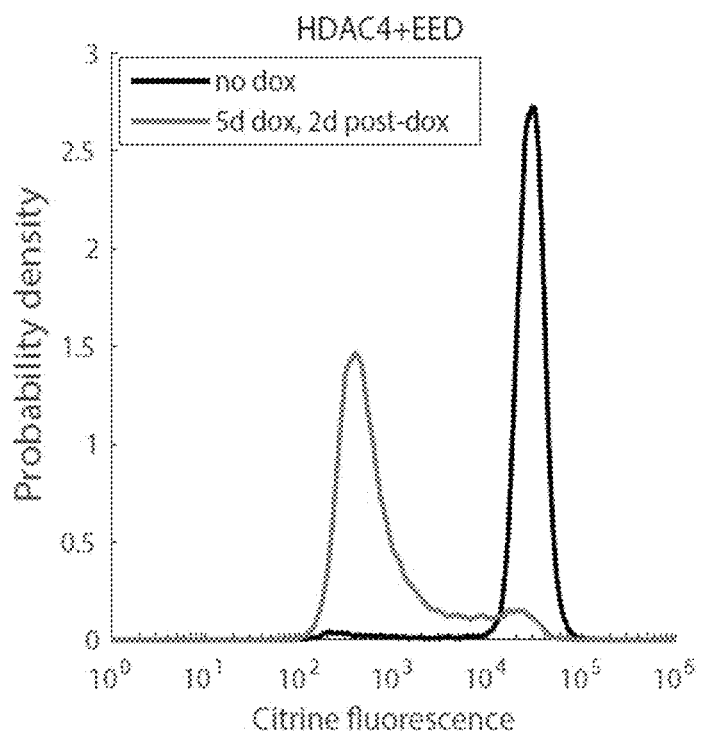
FIG. 18B
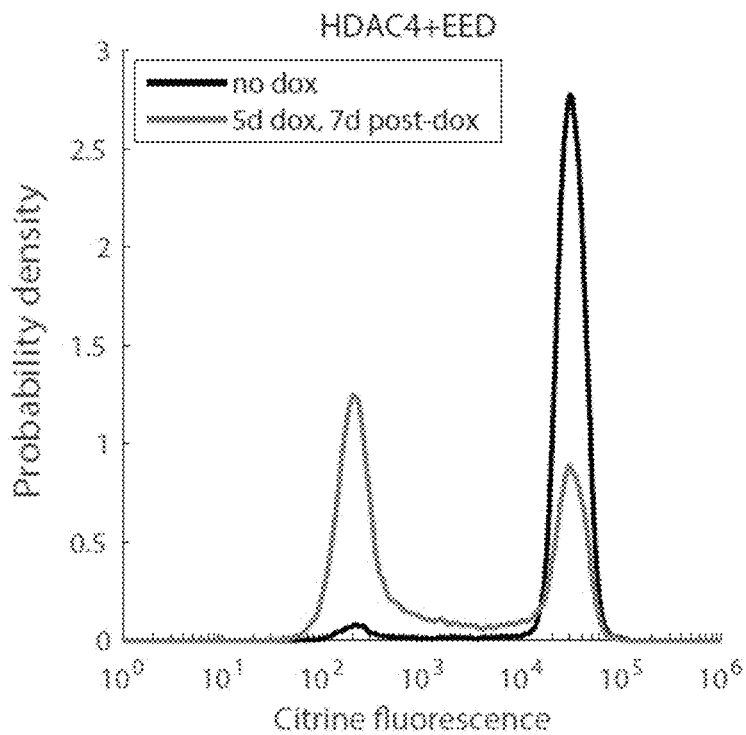

SEQUENCE LISTING

<160> NUMBER OF SEQ ID NOS: 8

<210> SEQ ID NO 1
<211> LENGTH: 20
<212> TYPE: DNA
<213> ORGANISM: artificial
<220> FEATURE:
<223> OTHER INFORMATION: pEF forward primer

<400> SEQUENCE: 1
acgtatgtcg aggtaggcgt                                              20

<210> SEQ ID NO 2
<211> LENGTH: 20
<212> TYPE: DNA
<213> ORGANISM: artificial
<220> FEATURE:
<223> OTHER INFORMATION: pEF reverse primer

<400> SEQUENCE: 2
ctaggcaccg gttcaattgc                                              20

<210> SEQ ID NO 3
<211> LENGTH: 27
<212> TYPE: DNA
<213> ORGANISM: artificial
<220> FEATURE:
<223> OTHER INFORMATION: citrine forward primer

<400> SEQUENCE: 3
cggcgacgta aacggccaca agttcag                                   27

<210> SEQ ID NO 4
<211> LENGTH: 21
<212> TYPE: DNA
<213> ORGANISM: artificial
<220> FEATURE:
<223> OTHER INFORMATION: citrine reverse primer

<400> SEQUENCE: 4
cttgccggtg gtgcagatga a                                         21

<210> SEQ ID NO 5
<211> LENGTH: 20
<212> TYPE: DNA
<213> ORGANISM: artificial
<220> FEATURE:
<223> OTHER INFORMATION: actin forward primer

<400> SEQUENCE: 5
actgggacga tatggagaag                                           20

<210> SEQ ID NO 6
<211> LENGTH: 20
<212> TYPE: DNA
<213> ORGANISM: artificial
<220> FEATURE:
<223> OTHER INFORMATION: actin reverse primer

<400> SEQUENCE: 6
ggtcatcttt tcacggttgg                                           20

<210> SEQ ID NO 7
<211> LENGTH: 20
<212> TYPE: DNA
<213> ORGANISM: artificial
<220> FEATURE:
<223> OTHER INFORMATION: Igf2 forward primer

<400> SEQUENCE: 7
ctgtggcctg taggtccttg                                           20

<210> SEQ ID NO 8
<211> LENGTH: 20
<212> TYPE: DNA
<213> ORGANISM: artificial
<220> FEATURE:
<223> OTHER INFORMATION: Igf2 reverse primer

<400> SEQUENCE: 8
cctctgcctt tccctcttgg                                           20

FRACTIONAL REGULATION OF TRANSCRIPTION

CROSS-REFERENCE TO RELATED APPLICATION(S)

The present application claims priority to and the benefit of U.S. Provisional Application Ser. No. 62/148,366 filed on Apr. 16, 2015, entitled "Fractional Control Devices Based on Chromatin Regulators," the entire content of which is incorporated herein by reference.

STATEMENT REGARDING FEDERALLY SPONSORED RESEARCH OR DEVELOPMENT

This invention was made with government support under Grant No. W911NF-11-2-0055 awarded by the Army and under Grant No. HD075605 awarded by the National Institutes of Health. The government has certain rights in the invention.

INCORPORATION BY REFERENCE

The instant application contains a Sequence Listing which has been submitted in ASCII format via EFS-Web and is hereby incorporated by reference in its entirety. Said ASCII copy, was created on Jul. 6, 2016, is named 79920SEQLISTING.txt, and is 1,708 bytes in size.

BACKGROUND

Cells use a system of chromatin regulators (CRs) and associated histone and DNA modifications to modulate gene expression and establish long-term epigenetic memory. This system is critical in development, aging, and disease, and may provide essential capabilities for incorporating regulation in synthetic biology. In these contexts, the temporal dynamics and cell-to-cell variability of gene expression are critical, but have been difficult to study because current methods usually provide static correlations between chromatin modifications and gene expression, and aggregate data across potentially heterogeneous cell populations. Therefore, it has remained unclear how strongly, how rapidly, and how uniformly each regulator can alter gene expression, and how long these effects persist

SUMMARY

In some embodiments of the present invention, a method of controlling the number of cells in a population of cells having silenced transcription of a target nucleic acid includes recruiting a chromatin regulator (CR) to a site proximal to a transcription initiation site of the target nucleic acid to form a fraction of silenced cells in the population of cells. The chromatin regulator may be EED, KRAB, DNMT3, HDAC4, EZH2, REST, or a combination thereof.

In some embodiments of the present invention, the method of controlling the number of cells in a population of cells includes recruiting a chromatin regulator followed by releasing the chromatin regulator thereby ending the recruitment first time period and starting the release second time period.

In some embodiments of the present invention, the chromatin regulator is DNMT3B and after releasing the chromatin regulator, the fraction of silenced cells is maintained in the second time period through subsequent cell divisions.

In some embodiments of the present invention, the chromatin regulator is HDAC4 and after releasing the chromatin regulator, the silenced transcription in the fraction of silenced cells is reversed.

In some embodiments of the present invention, the chromatin regulator is EED, KRAB, EZH2, or a combination thereof, and wherein after releasing the chromatin regulator, the fraction of silenced cells include a number of reversibly silenced number of cells and a number of permanently silenced cells.

BRIEF DESCRIPTION OF THE DRAWINGS

The patent or application file contains at least one drawing executed in color. Copies of this patent or patent application publication with color drawings will be provided by the Office upon request and payment of the necessary fee.

see last column, left bars. The observed conditional silencing probability was compared to the expected counterpart, assuming silencing events are stochastic and independent in the two sisters. This expected probability and its 95% confidence intervals (last column, right bars) were estimated using the same equation on results from a random permutation test with 100,000 trials; and while the observed probability is higher than the expected value for EED, DNMT3B, and HDAC4, these observed values were still closer to the expected values assuming complete independence, than to the expected value assuming complete correlation (P=1), or complete anti-correlation (P=0) between sister cells. These results indicate a substantial stochastic component in the silencing process.

Figure 10A:
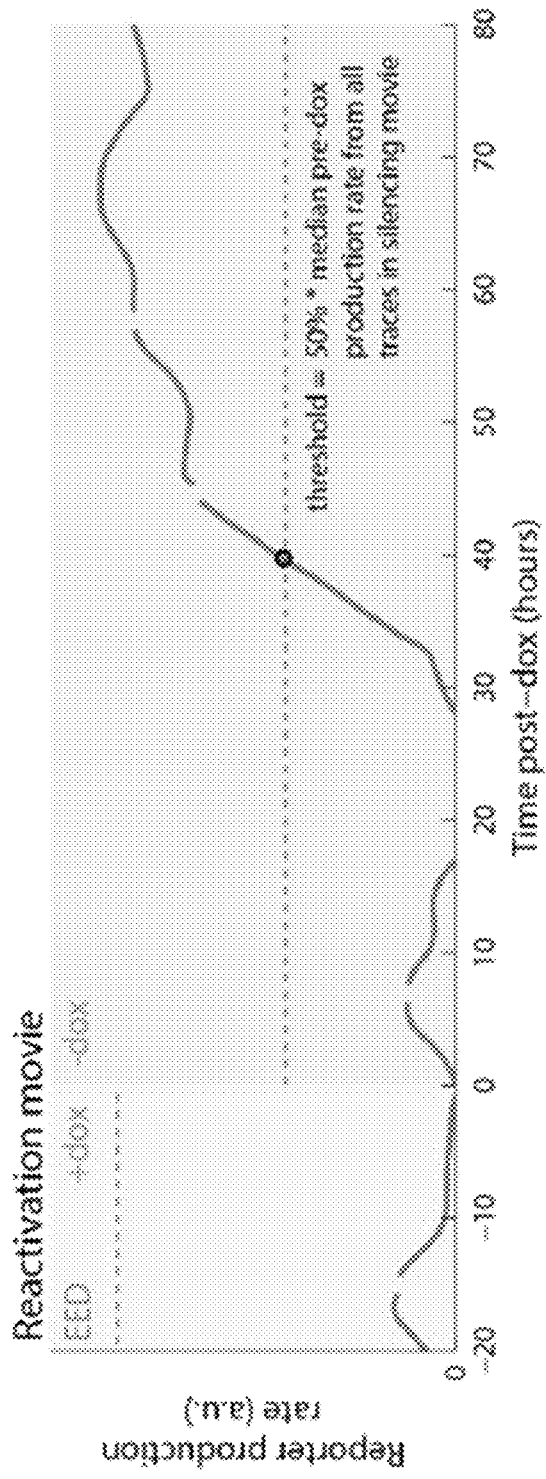

FIG. 10A shows graph of a fluorescence trace during a reactivation video (movie) captured using EED-mediated Citrine reporter production during both recruitment (in the presence of dox) and reactivation (removal of dox), according to embodiments of the present invention. The cyan curve is the smoothed time derivative of the cumulative fluorescence trace for the same cell lineage shown in FIG. 3A, where reactivation events were detected in a similar way as silencing events but in the opposite direction. The median pre-dox production rate from all lineage traces in a silencing movie immediately preceding the reactivation movie was used to set a single threshold to detect reaction events as indicated with dashed lines. Reactivation events were defined by an increase in production rate above this threshold that was sustained for ≥12 hours.

Figure 3A:
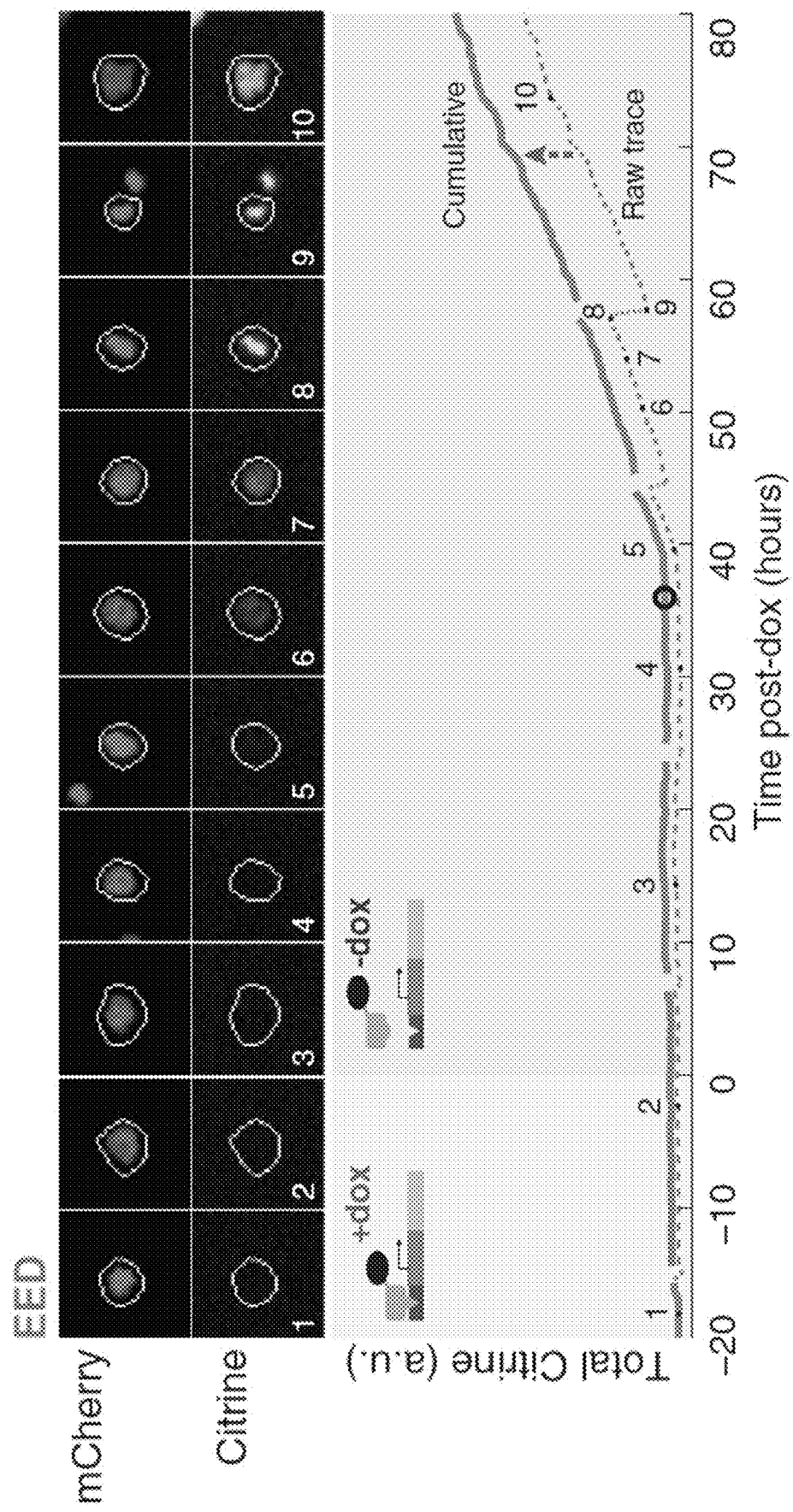
FIG. 3A shows a video filmstrip and corresponding fluorescence trace during EED release, according to embodiments of the present invention, in which the traces, numbers, and shading are as defined in FIG. 2A.
Figure 3B:
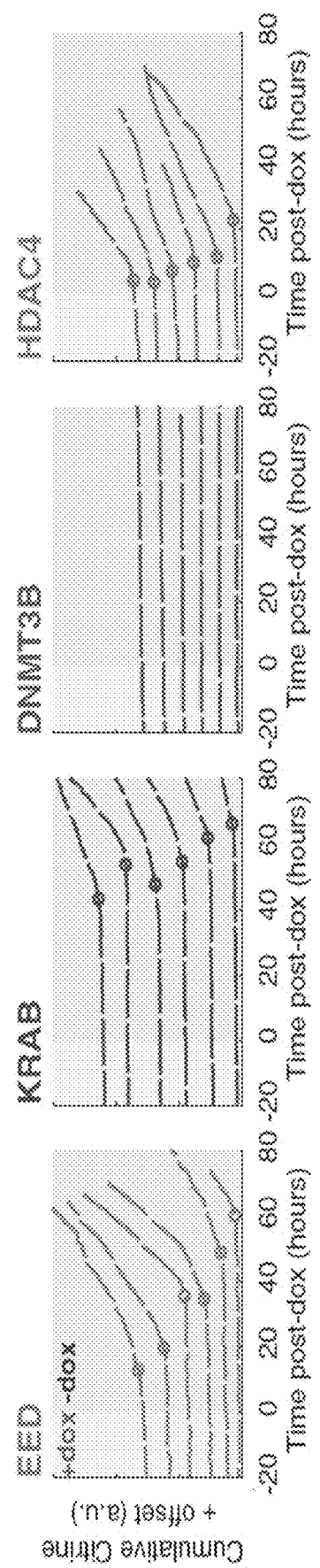
FIG. 3B is a graph of representative single-cell traces showing reactivation events for EED (cyan), KRAB (blue), and HDAC4 (green) as indicated by circles where only reactivated cells are shown, and where no reactivation events were observed for DNMT3B (red) so only silent cells were plotted, and traces are vertically offset for clarity, according to embodiments of the present invention.
Figure 10B:
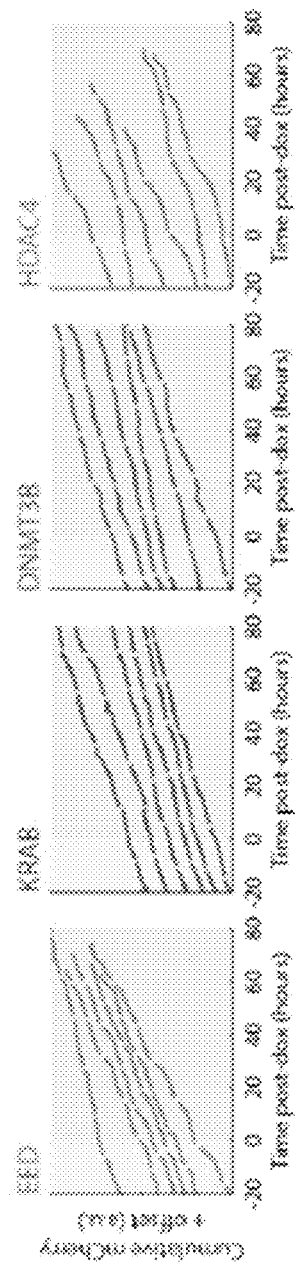

FIG. 10B shows graphs of single-cell fluorescence traces, according to embodiments of the present invention, for each of EED, KRAB, DNMT3B, and HDAC4 as indicated in the constitutive reporter H2B-mCherry channel of the same cell lineages as shown in FIG. 3B and arranged in the same order where traces are vertically offset for clarity; the control H2B-mCherry reporter showed steady production in all traces, indicating that dox-mediated silencing is likely specific to the H2B-Citrine reporter locus rather than a genome-wide effect.

Figure 3C:
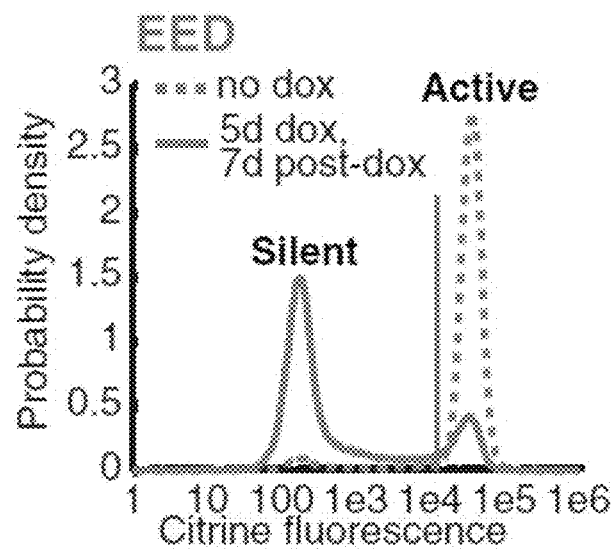
FIG. 3C is a graph of fluorescence from flow cytometry analysis of cells expressing EED in the absence of doxycycline (dox) (dotted line) or presence (5 days of dox, followed by 7 days no dox) (solid line), according to embodiments of the present invention, in which the silent cells (expression repressed) are represented by the low fluorescence peak to the left of the threshold line at 1e4 fluorescence intensity, and the active cells are to the right of the threshold line.
Figure 11A:
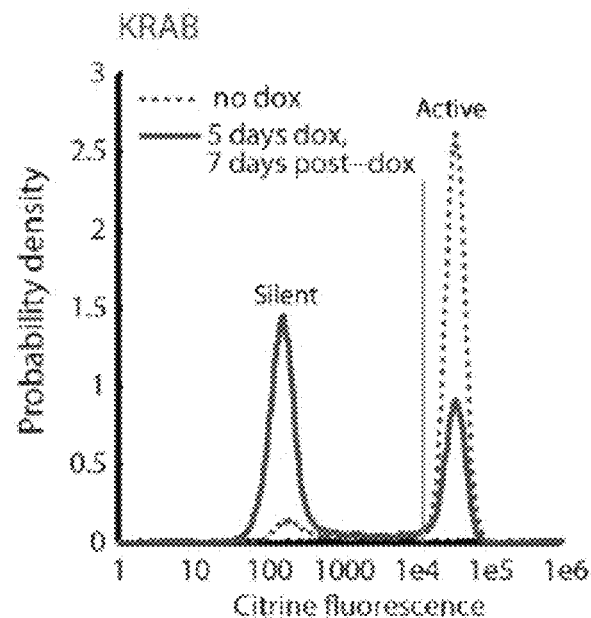
Figure 11B:
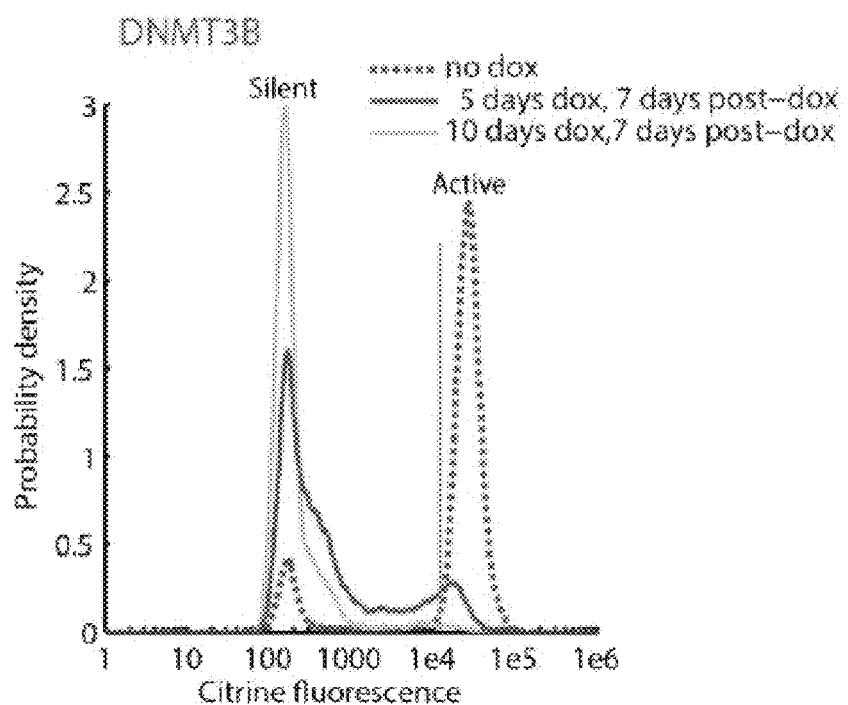
Figure 11C:
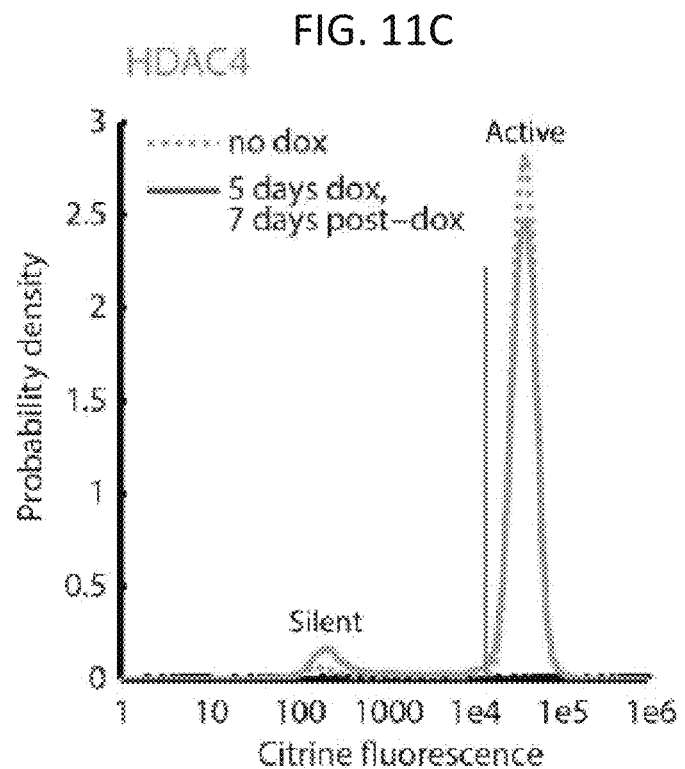

FIGS. 11A-11C are graphs, according to embodiments of the present invention, of Citrine reporter fluorescence distribution as measured by flow cytometry for KRAB, DNMT3B, and HDAC4, respectively, (similar to the graph of EED shown in FIG. 3C), where distributions are shown for cells treated with dox for 5 days, followed by 7 days of culture without dox (solid blue, red, or green lines, respectively) and for cells cultured in parallel with no dox (blue, red, or green dashed lines); where the vertical gray line in each graph represents the threshold used to determine the fraction of cells silent.

Figure 11D:
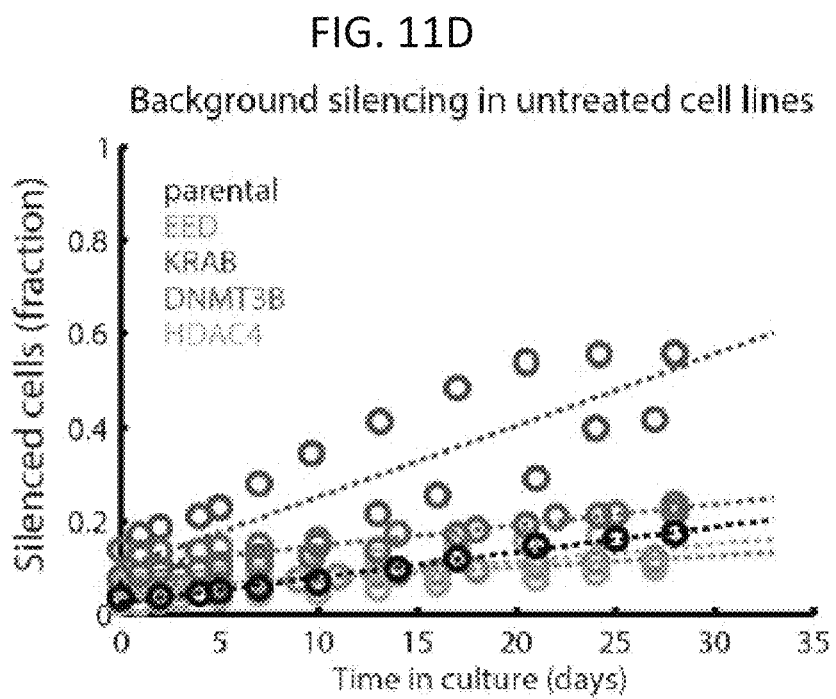

FIG. 11D is a graph showing that low rates of background silencing occur even in the absence of dox. For each CR, the background fraction of cells that were silenced in the absence of dox was subtracted from the observed fraction of silenced cells to generate the graphs shown in FIGS. 3D, 4C-4F, and 13B.

Figure 12A:
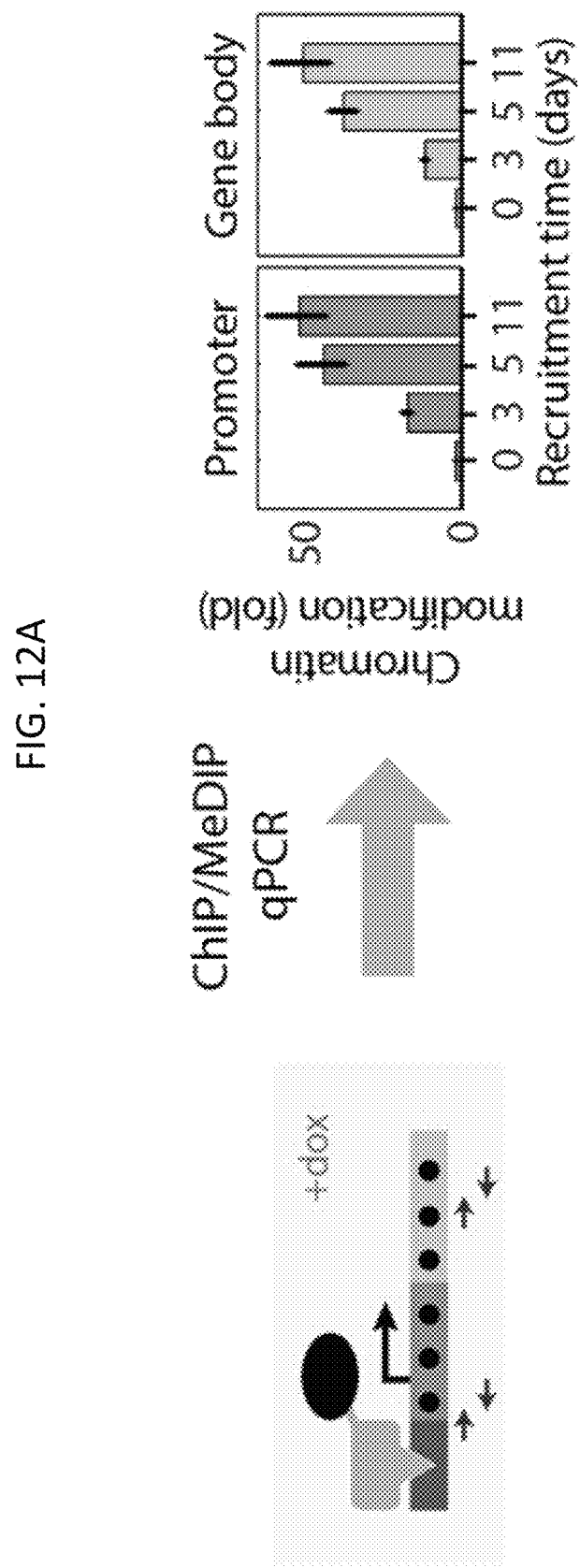

FIG. 12A is a schematic depicting an experimental strategy, according to embodiments of the present invention, for chromatin immunoprecipitation (ChIP) and methylDNA immunoprecipitation (MeDIP), followed by qPCR to quantify five common chromatin modifications at the promoter (arrows below orange region) and in the gene body (arrows below the yellow region) after different durations of CR recruitment (0, 3, 5, or 11 days of dox treatment), as described herein.

Figure 12B:
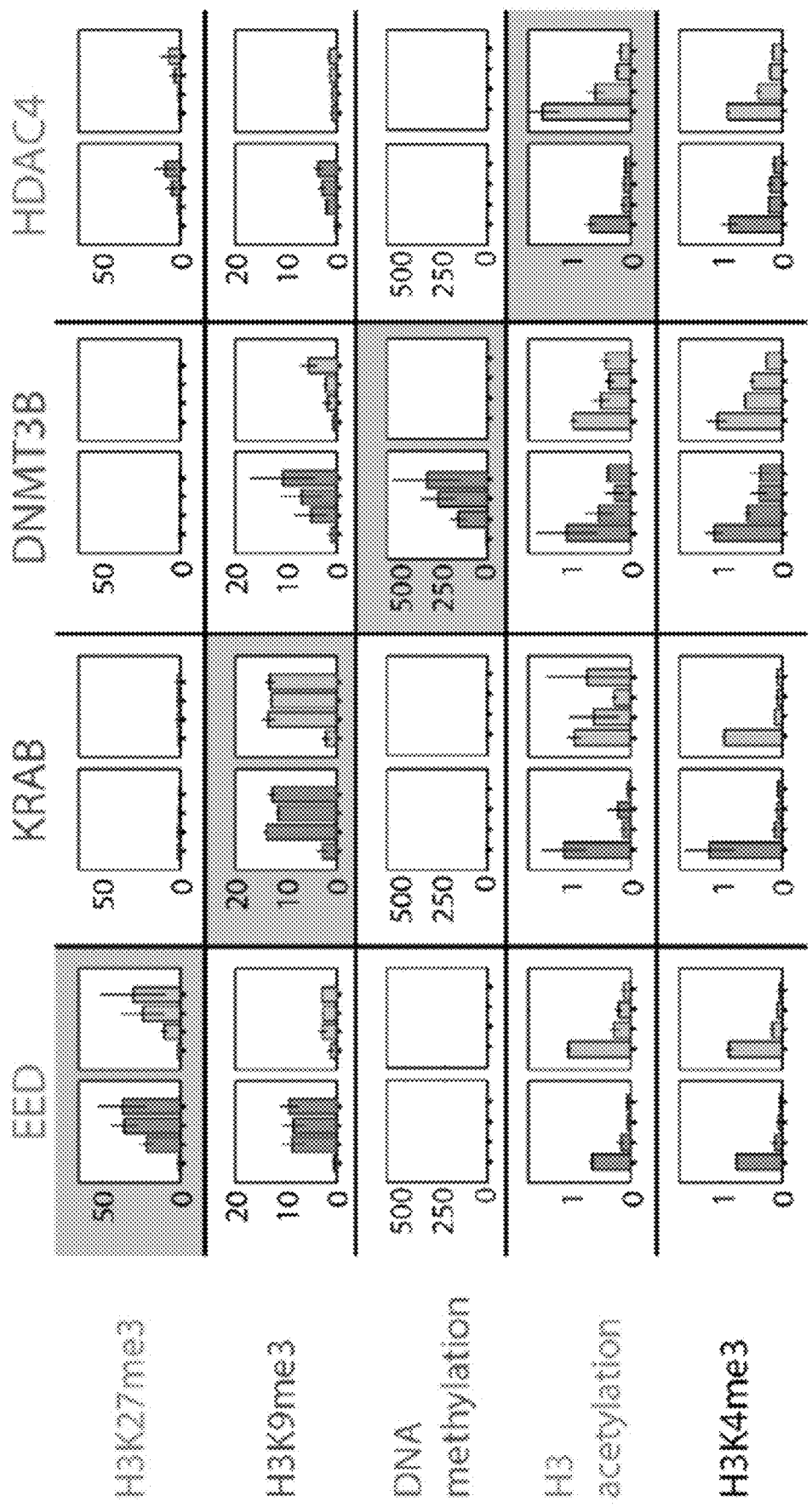

FIG. 12B shows the results from the experiments following the experimental strategy of FIG. 12A carried out to quantify the chromatin modifications of H3K27me3, H3K9me3, DNA methylation, H3 acetylation, and H3K4me3 at the pEF promoter (orange bars) and in the citrine reporter gene body (yellow bars) during CR recruitment of each of EED, KRAB, DNMT3B, and HDAC4, according to embodiments of the present invention, where qPCR signals were normalized by β-actin (for active marks) or IgF2 (for repressive marks) and plotted as fold-change (mean standard deviation (s.d.)) relative to the parental (reporter only) cell line. As shown in each profile, each CR promoted its corresponding modification (shaded plots), and recruitment of one CR also led, directly, or indirectly, to other modifications—e.g., active modifications (H3 acetylation and H3K4me3) decreased in all cases, and the repressive H3K9me3 modification associated with KRAB also appeared in response to EED and DNMT3B recruitment. In contrast, H3K27me3 and DNA methylation were more specific to EED and DNMT3B, respectively, and although molecular states produced by each of the CRs partially overlapped, each CR produced a silent state with a distinct molecular signature (i.e., each column is unique).

Figure 13A:
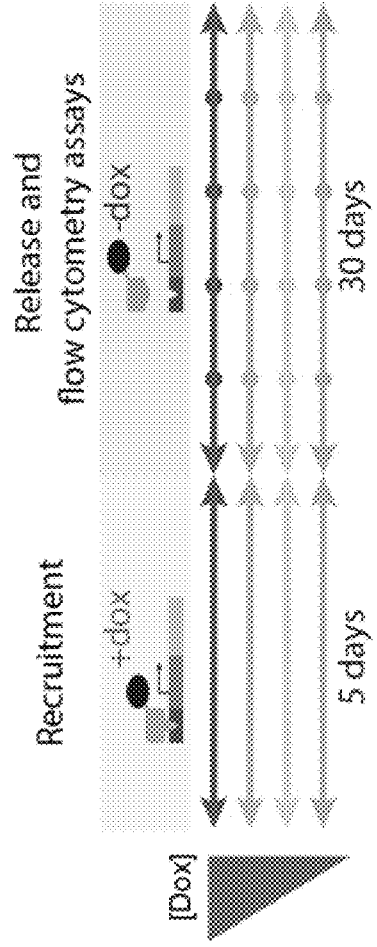

FIG. 13A is schematic showing an experimental design for elucidating that different CRs maintain their distinct dynamic modes at lower recruitment strengths, in which for each CR, cells were induced for 5 days at varying concentrations of dox (different colors arrows with dox concentrations increasing from green to red as shown; and the fraction of silent cells was measured by flow cytometry for 30 days following CR release (post-dox), according to embodiments of the present invention.

Figure 13B:
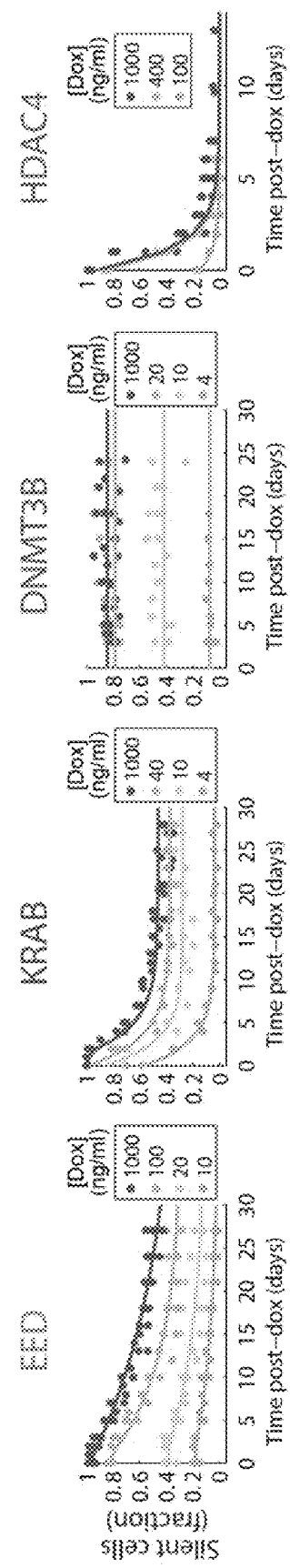

FIG. 13B shows graphs measuring the fraction of silent cells after recruitment in different dox concentrations as indicated for each of EED, KRAB, DNMT3B, and HDAC4, according to embodiments of the present invention, where the fraction of cells that remain silent after CR release is plotted against time (days) since dox was removed, and the dots represent data from at least two independent sets of flow cytometry experiments, and lines are fits to these data with the models as in FIGS. 4C-4F; where for each CR, the strength of recruitment (i.e., dox concentration) controls the fraction of silent cells in a similar manner to the duration of recruitment as compared to FIGS. 4C-4F, and even at a lower recruitment strength, EED and KRAB show hybrid memory, DNMT3B leads to irreversible silencing, and HDAC4 produces reversible silencing.

Figure 14A:
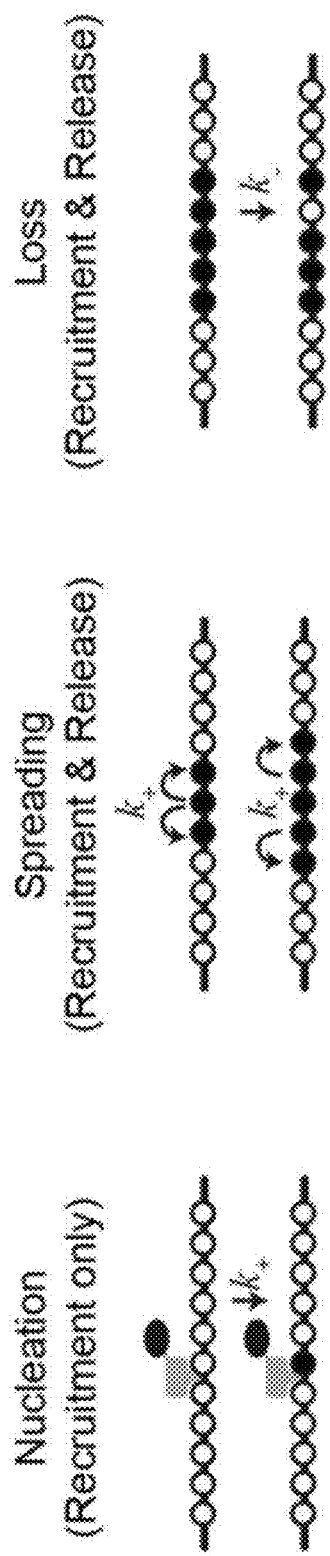

FIG. 14A is a schematic of a molecular model of chromatin modifications that lead to stochastic silencing and reactivation at constant rates, according to embodiments of the present invention. An array of nucleosomes (circles) that can each be in one of two states: unmodified (white), and modified (black), where upon recruitment of a R, the target nucleosome at the center becomes modified (left), at a rate $k_+$; and modifications can stochastically spread to the neighboring nucleosomes at the same rate $k_+$ (middle), and the modifications can be lost at a constant rate $k_-$ along the array (right). In the model, nucleation takes place only during recruitment of a CR, while spreading and loss happen both during recruitment and release of the CR, according to embodiments of the present invention.

Figure 14B:
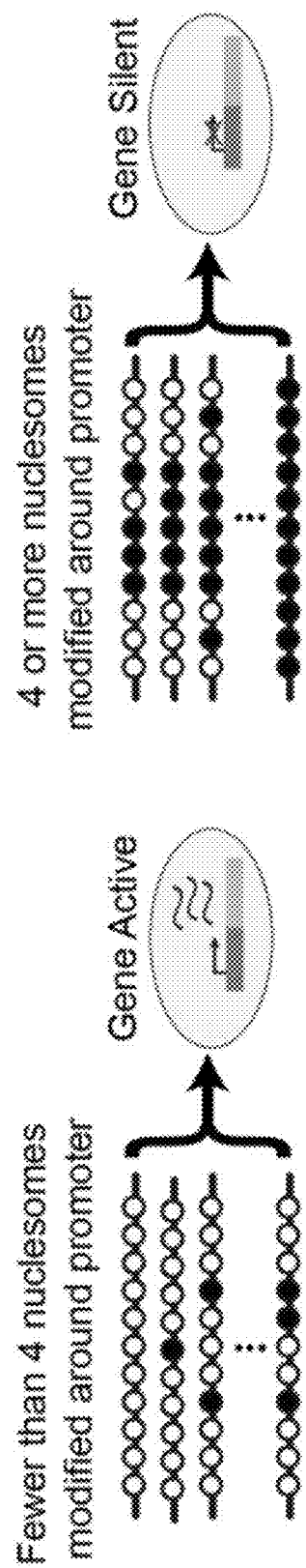

FIG. 14B is a schematic of a molecular model according to embodiments of the present invention that connects chromatin states to gene expression in which an arbitrary threshold is set: during the simulation, the gene is considered silent if 4 or more of the 11 nucleosomes closest to the target site are modified (left), and are otherwise considered active (right).

FIGS. 14C-14D are graphs measuring the fraction of silenced cells during Recruitment (FIG. 14C) or Release (FIG. 14D) for which the data obtained from a molecular simulation using the model described in FIG. 14A and FIG. 14B are shown in black. The gain/spreading and loss rates used in the simulation were: $k_+=0.176$ h$^{-1}$ and $k_-=0.117$ h$^{-1}$; black dots represent the average for 100 cells/arrays, and the black lines represent standard deviations over 10 trials. These simulated data can be fit by the three-state model shown in FIG. 4A (red lines), with the following rates: $k_S=0.7$ d$^{-1}$, $k_A=0.2$ d$^{-1}$, $k_r=0.06$ d$^{-1}$, and lag times before silencing $T_{lag1}=0.15$ d, and before reactivation $T_{lag2}=0$ d. These rates are comparable to the ones measured for EED and KRAB silencing and reactivation from experimental results, according to embodiments of the present invention.

Figure 15A:
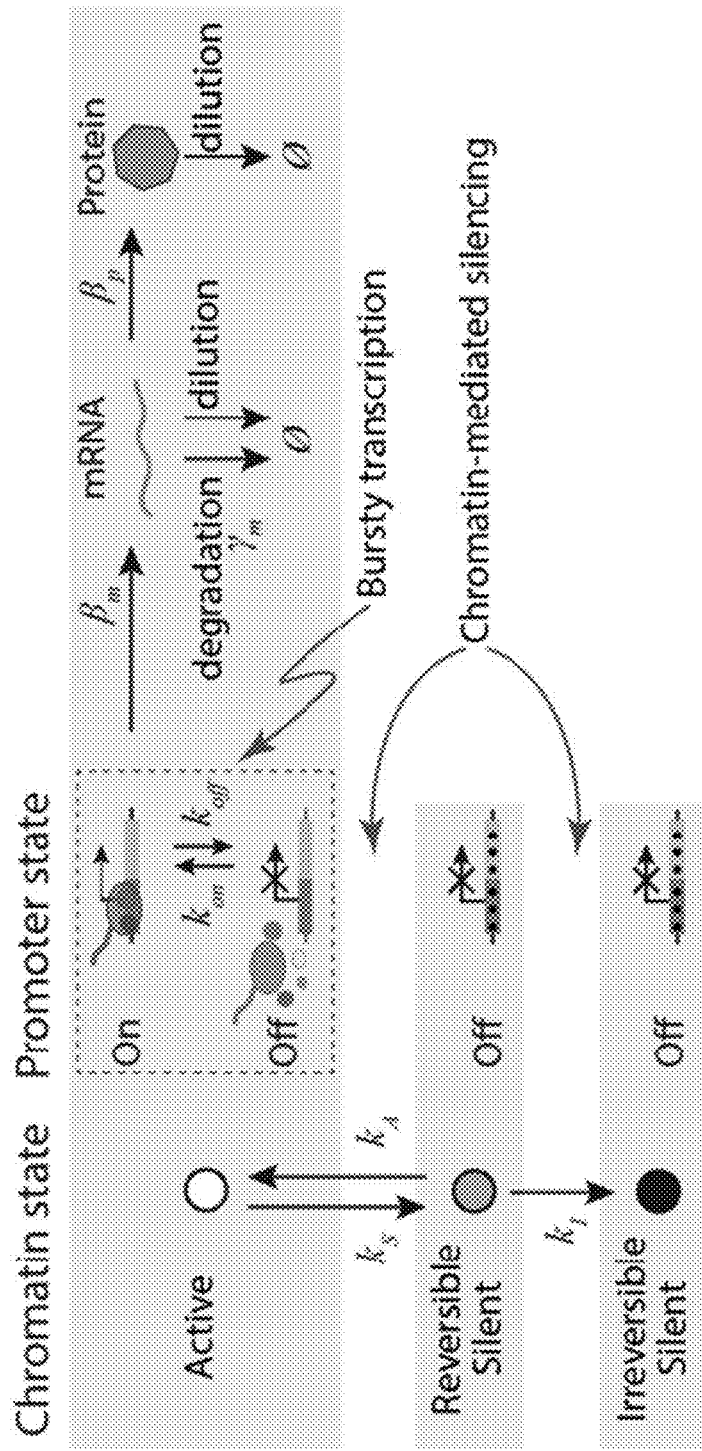

FIG. 15A is a schematic showing a three-state chromatin model combined with a stochastic transcription model by incorporating additional gene expression steps as disclosed herein, according to embodiments of the present invention.

FIGS. 15B-15E show graphs of citrine fluorescence distribution as measured by flow cytometry for EED, KRAB, DNMT3B, and HDAC4 cell lines, respectively, according to embodiments of the present invention. For each cell line, cells were treated at the indicated dox concentration (with a different color representing a different dox concentration) for five days before measurement, and no release time was allowed. The slow dilution of stable reporter protein contributes significantly to the observation of intermediate protein levels in bimodal distributions. The right graph for each CR in each of FIGS. 15B-15E shows a fluorescence distribution of cell populations for each CR simulated following the model shown in FIG. 15A and experimentally derived parameters of FIGS. 4G-4I.

FIGS. 16A-16D show graphs of reporter gene silencing using other chromatin repressors (CRs), where rTetR-CR fusions were induced by dox treatment for 5 days, and the resulting fluorescent distributions were measured using flow cytometry; where bimodal silencing was observed as shown for the EZH2 (FIG. 16A) and REST (FIG. 16B) CRs, and little or no silencing was observed for RNF2/RING1B (FIG. 16C) and HDAC3 (FIG. 16D), respectively, according to embodiments of the present invention.

Figure 4A:
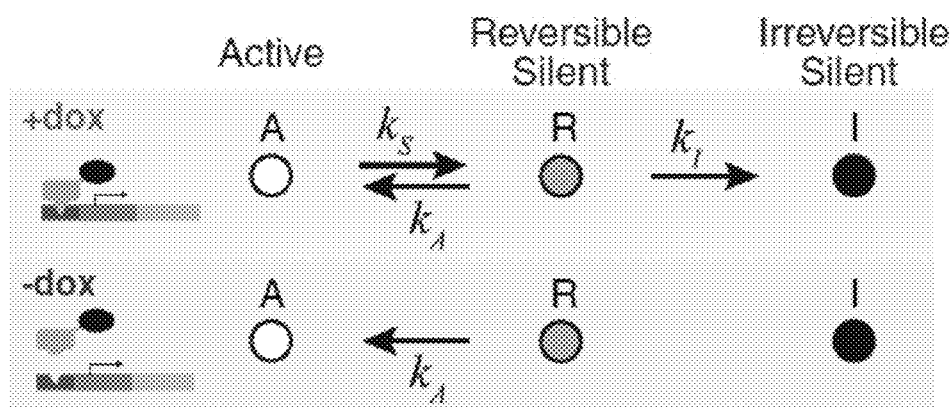
FIG. 4A is a schematic of a model based on stochastic transitions between states of actively expressing (A), reversibly silent (R), and irreversibly silent (I), according to embodiments of the present invention, in which the silencing rates ($k_S$ and $k_I$) depend on recruitment, whereas reactivation ($k_A$) is independent of recruitment.
Figure 4B:
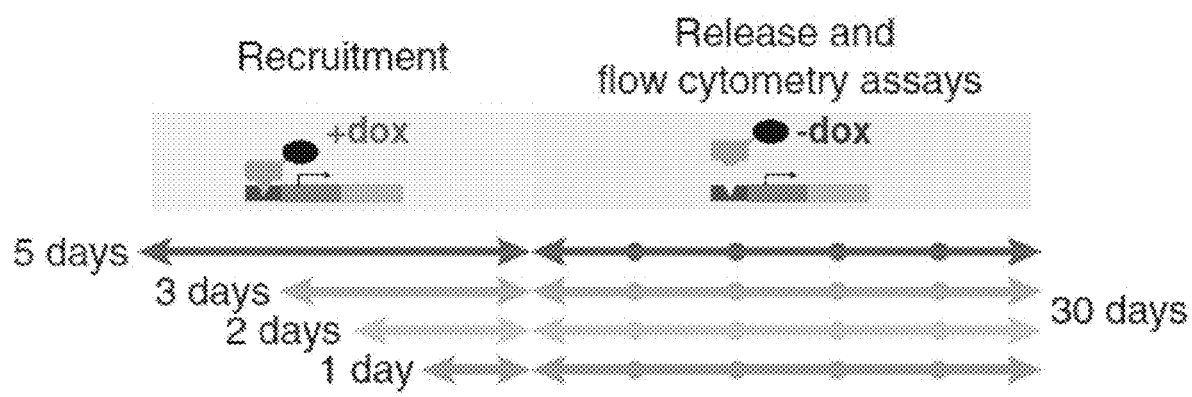
FIG. 4B is a schematic depicting an experimental strategy according to embodiments of the present invention, for which the duration of recruitment (presence of doxycycline) was varied from 1 to 5 days (colored arrows), and after removal of dox, the fraction of cells remaining silenced was measured for up to 30 days.

FIG. 17A is a schematic depicting an experimental strategy similar to FIG. 4B, according to embodiments of the present invention, for which the duration of EZH2 recruitment (presence of doxycycline) was assayed for 1, 2, 3, and 5 days as shown (colored arrows), and after removal of dox (Release), the fraction of cells remaining silenced for expression of citrines was measured for up to 30 days.

FIG. 17B is a graph showing the fraction of silenced cells measured over 30 days by flow cytometry after varying lengths (1, 2, 3, or 5 days indicated by green, yellow, orange, and red lines) of EZH2 recruitment as set forth in FIG. 17A, according to embodiments of the present invention.

FIG. 18A shows the fluorescence distribution of cells containing rTetR-HDAC4 and rTetR-EED in the absence of recruitment (no dox, black line) and after recruitment (cyan line) for 5 days of dox induced-recruitment of both CRs and 2 days of post-dox release, according to embodiments of the present invention.

FIG. 18B shows the fluorescence distribution of cells as described in FIG. 18A, except the post-dox release period was 7 days, according to embodiments of the present invention.

Figure 18C:
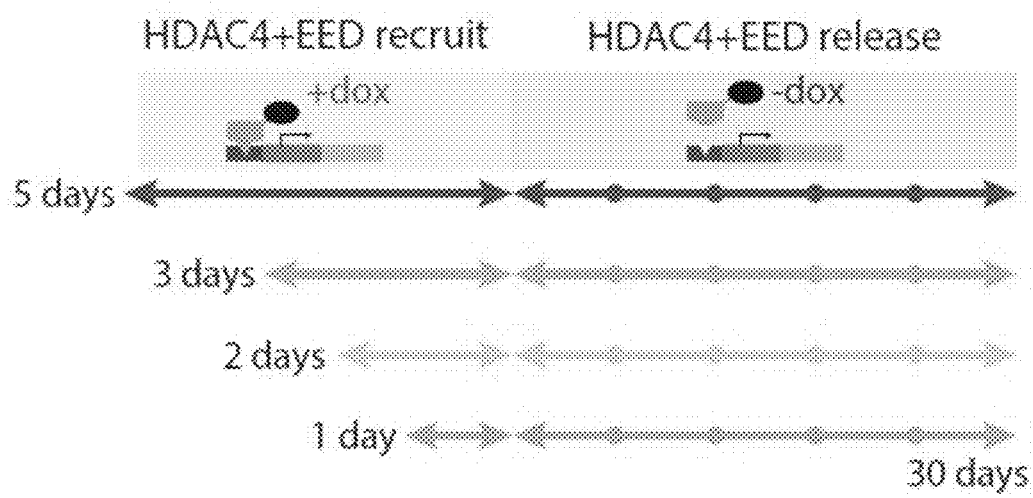

FIG. 18C is a schematic depicting an experimental strategy similar to FIGS. 4B and 17A, according to embodiments of the present invention, for which the duration of HDAC4 and EED recruitment (presence of doxycycline) was assayed for 1, 2, 3, and 5 days as shown (colored arrows), and after removal of dox (Release), the fraction of cells remaining silenced for expression of citrines was measured for up to 30 days.

Figure 18D:
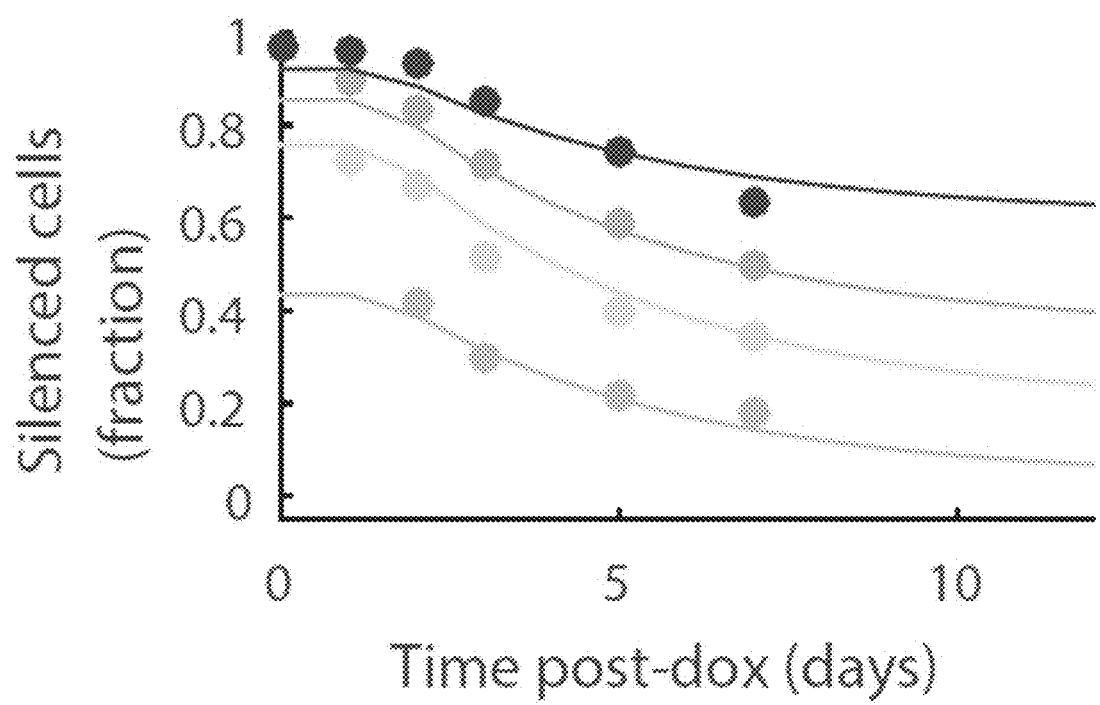

FIG. 18D is a graph showing the fraction of silenced cells measured over 30 days by flow cytometry after varying lengths (1, 2, 3, or 5 days indicated by green, yellow, orange, and red lines) of HDAC4 and EED recruitment as set forth in FIG. 18C, according to embodiments of the present invention.

DETAILED DESCRIPTION

Figure 1A:
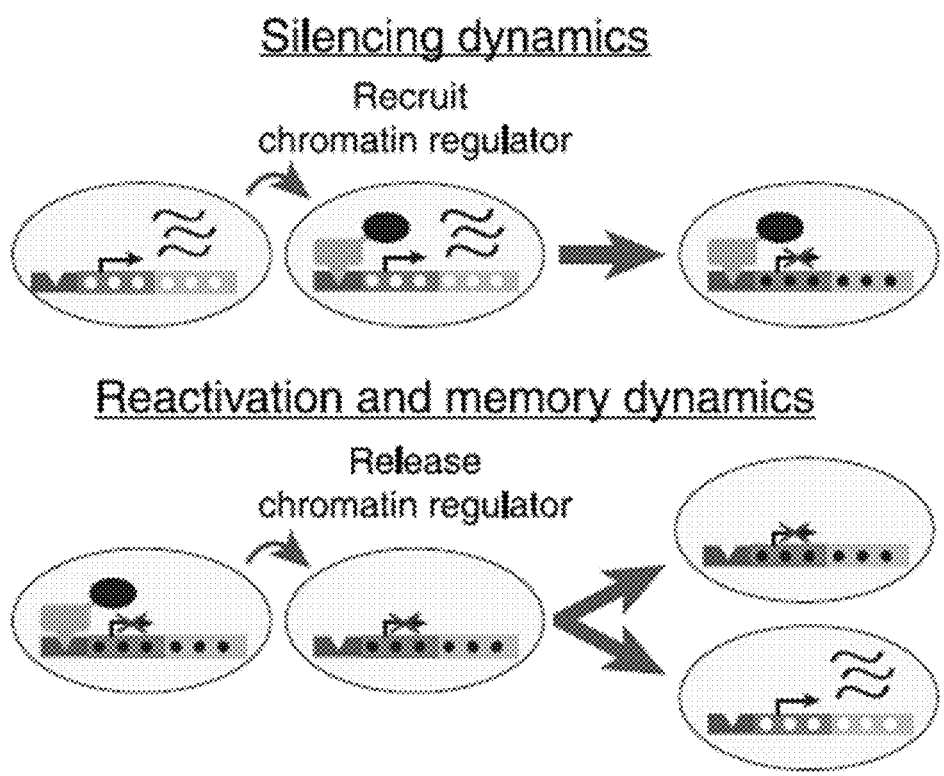
FIG. 1A is a schematic depicting how direct recruitment of a chromatin regulator (CR, black) to a reporter gene enables analysis of subsequent silencing dynamics (upper panel) according to embodiments of the present invention, where after silencing, the releasing of CR allows analysis of epigenetic memory and reactivation dynamics (lower panel), with white and black dots representing changes in chromatin modifications.

Chromatin regulators (CRs) play a major role in establishing and maintaining the expression of genes through regulation of transcription. Embodiments of the present invention include methods for regulating transcription of a target nucleic acid by regulating the recruitment of CRs to the site of transcription of the target nucleic acid. According to embodiments of the present invention, a target nucleic acid in a population of cells may be fractionally regulated by controlling the variables of CR recruitment. In some embodiments of the present invention, CR recruitment to the site of transcription results in the silencing of the target nucleic acid in a percentage of cells. In some embodiments, for example, the percentage of cells having silenced expression of the target nucleic acid may increase with the duration of CR recruitment. Additionally, the reversibility of the silenced expression may be controlled with selection of CR types and duration of the CR recruitment. According to embodiments of the present invention, a method of fractionally silencing expression of a target nucleic acid in a population of cells includes recruiting a chromatin regulator to the site of transcription of the target nucleic acid as depicted in FIG. 1A.

In some embodiments of the present invention, induced CR-silencing of a target nucleic acid in a fraction of a cell population may be reversible or irreversible. The reversibility or irreversibility of the induced CR-silencing is dependent upon the specific CR recruited to the site of the target nucleic acid and/or the duration of the recruitment.

According to embodiments of the present invention, the chromatin regulators capable of silencing expression of a target nucleic acid may include EED, KRAB, DNMT3, HDAC4, EZH2, REST, and combinations thereof.

As used herein, EED refers to the embryonic ectoderm development chromatin regulator. EED functions as part of the Polycomb repressive complex 2 (PRC2) which methylates histone H3 at lysine 27 (H3K27me3).

As used herein, KRAB refers to the Kruppel associated box chromatin regulator. KRAB functions within more than 400 zinc finger transcription factors and associates with other CRs that write or read H3K9me3.

As used herein, DNMT3B refers to DNA methyltransferase 3B chromatin regulator. DNMT3B causes de novo methylation of cytosine-guanine dinucleotides (CpGs).

As used herein, HDAC4 refers to histone deacteylase 4. HDAC4 removes acetyl groups from histones H3 and H4.

As used herein, EZH2 refers to the enhancer of zedste homolog 2. EZH2 is a histone-lysine N-methyltransferase enzyme that methylates histone 3 at lysine 27.

As used herein, REST refers to repressor element 1 (RE1) Silencing Transcription Factor. REST is a regulator of neuronal and glial cell fate in stem cell differentiation.

As used herein "recruitment," "recruiting," and like terms refer to the targeting of a chromatin regulator (CR) upstream or downstream of a target nucleic acid. In some embodiments, recruiting of a CR in cellulo is controlled using a system in which the CR is fused to a DNA binding domain with the corresponding DNA sequence inserted proximal to the transcription initiation site of the target nucleic acid. Techniques for engineering a fusion protein having a DNA binding domain are well known in the art. Non-limiting examples of DNA binding domain proteins capable of being fused to a CR for recruiting include the tetracycline (Tet) repressor (TetR), lactose inhibitor (LacI), Gal4, dead Cas9 (dCas9) (part of CRISPR), transcription activator-like effector (TALE) proteins, and zinc finger proteins as described in Lienert et al., 2014, Nat. Rev. Mol. Cell Biol., 15:95-107, the entire contents of which are herein incorporated by reference. The binding or expression of the DNA binding domain proteins may be regulated thereby allowing for control of the recruitment. For example, the reverse TetR (rTetR) protein only binds DNA in the presence of tetracycline or its derivative doxycycline. The reverse TetR (rTetR) protein fused to the chromatin regulators is used in some of the examples disclosed herein and regulated with doxycycline (dox).

As used herein, the phrase, "proximal to a transcription initiation site," refers to the nucleotide basepairs upstream or downstream of the target nucleic acid. In order to confer silencing, the CR is recruited to a proximal site that is at or within 5,000 basepairs (5 kb) upstream or downstream of the transcription initiation site of the target nucleic acid. In some embodiments, the site proximal to the transcription initiation site is at or within 4 kb upstream or downstream of the transcription initiation site of the target nucleic acid. In some embodiments, the site proximal to the transcription initiation site is at or within 3 kb upstream or downstream of the transcription initiation site of the target nucleic acid. In some embodiments, the site proximal to the transcription initiation site is at or within 2 kb upstream or downstream of the transcription initiation site of the target nucleic acid. In some embodiments, the site proximal to the transcription initiation site is 1 kb upstream or downstream of the transcription initiation site of the target nucleic acid.

As used herein, "duration of recruitment" and like terms refer to the amount of time a CR is targeted to a site proximal to the transcription initiation site of a target nucleic acid. The recruitment time period is also sometimes referred to as the first time period. For example, using the rTetR-CR system, the duration of recruitment is the amount of time the cell is exposed to tetracycline or doxycycline. As understood by those having ordinary skill in the art, the duration of recruitment and the results on silencing of the target nucleic acid will depend upon cell type, the CR or CRs being used, as well as the DNA binding domain fused to the CR. The duration of recruitment may be hours to days in length.

As used herein, "releasing of CR," "release", "release period," and like terms refer to the time period following the recruitment time period. The start of the release of CR begins when the recruitment time period ends. The releasing time period is also referred to as the second time period as it follows the first time period of recruitment. In some of the examples disclosed herein, the release of CR begins upon the removal of doxycycline (dox).

Figure 1B:
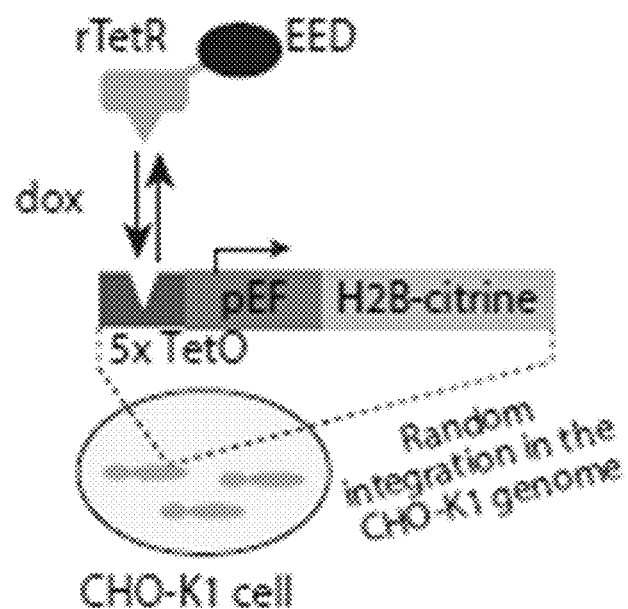
FIG. 1B shows two schematics depicting the cloning setup (upper schematic) and experimental workflow for silencing a target gene in the CHO-K1 genome (lower schematic), according to embodiments of the present invention, in which the reporter gene (pEF-H2B-Citrine) is stably inserted in the CHO-K1 genome using random integration. In this cell line, a second DNA construct encoding for a fusion between reverse tetracycline repressor (rTetR) and EED was also inserted for recruitment upstream of the reporter gene at the TetO binding sites by addition of doxycycline (dox). As shown in the workflow of the lower schematic, rTetR-EED is first recruited at the target reporter gene by dox addition for a time period T1 (middle panel, Recruit), and afterwards, rTetR-EED is released from the target reporter gene by washing out dox, and gene expression is measured after a time period T2 (right panel, Release).
Figure 1B:
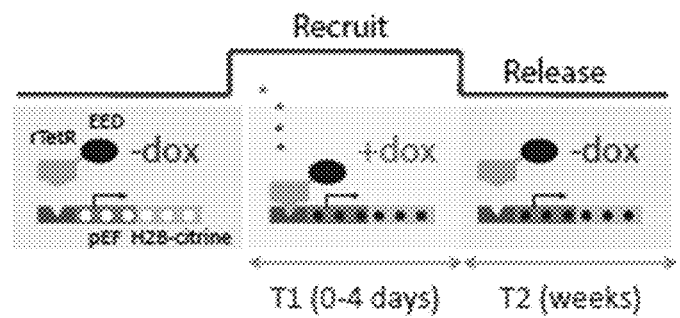
Figure 1C:
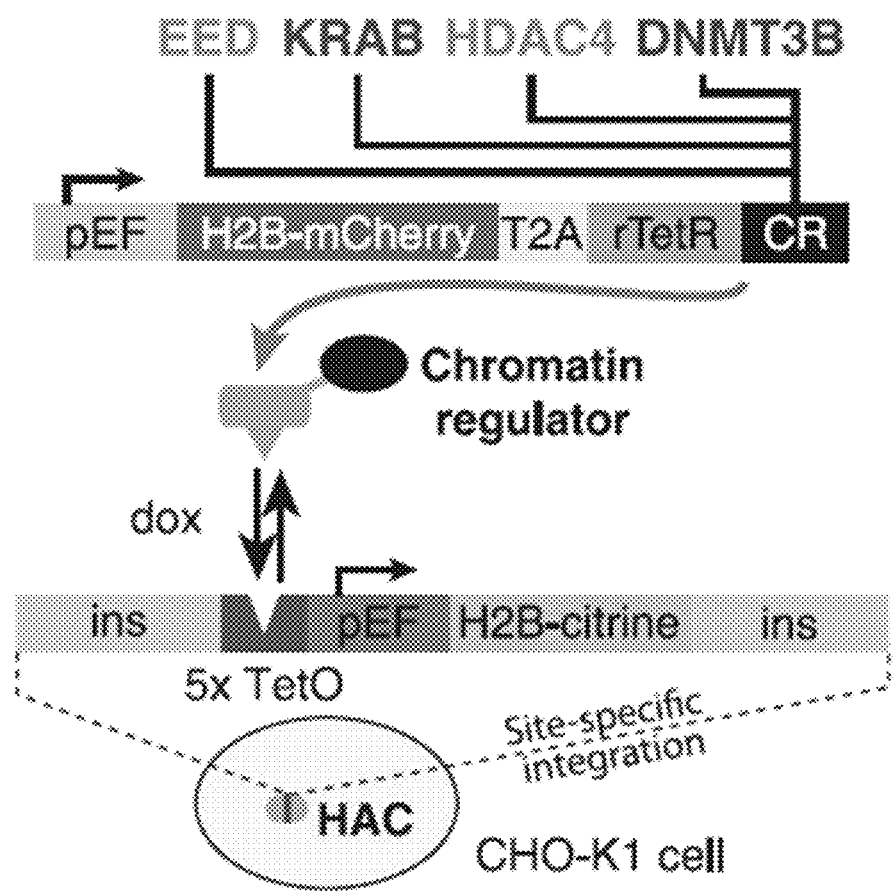
FIG. 1C is a schematic depicting a cloning construct, according to embodiments of the present invention, where the construct constitutively co-expresses H2B-mCherry and one of four CRs fused with the DNA-binding protein reverse tetracycline repressor (rTetR) (shown in top panel); engineered cells contain a target H2B-Citrine reporter gene driven by the mammalian elongation factor 1α promoter (pEF) containing five upstream rTetR binding sites (5× TetO) which, in the presence of doxycycline (dox), induce a conformational change in the CR-rTetR fusion protein to permit binding of rTetR to the TetO site, where the reporter is flanked by insulators (ins), and is site-specifically integrated on a human artificial chromosome (HAC) in CHO-K1 cells (bottom); and H2B domains localize fluorescent protein signals to the nucleus, thereby improving quantitation.

As used herein, "target nucleic acid," and like terms refer to the nucleic acid of interest to which a chromatin regulator (CR) is recruited. The target nucleic acid is expressed in a cell and may be integrated into the genome of a cell or expressed separate from the genome from a plasmid (FIG. 1B) or an artificial chromosome (e.g. a human artificial chromosome (HAC) (FIG. 1C). Expression of the target nucleic acid in a cell may occur in vitro or in vivo. For in vitro expression, the target nucleic acid may be expressed in a cultured cell. For in vivo expression, the target nucleic acid may be expressed in an animal subject model, for example, a mouse. Additionally, for some of the examples disclosed herein, the target nucleic acid encodes for the fluorescent reporter protein citrine which is constitutively expressed in the absence of doxycycline and repressed by rTetR-CR upon incubation with doxycycline. A target nucleic acid may be any nucleic acid that is capable of being transcribed in a desired cell or cell line. A target nucleic acid may encode for proteins, peptides, or RNAs. Non-limiting examples of RNAs include messenger RNA (mRNA), long noncoding RNA (lncRNA), interfering RNA (RNAi) including small interfering RNA (siRNA), short hairpin RNA (shRNA), microRNA (miRNA), and PIWI-interacting RNA (piRNA). As shown herein, in some embodiments, the target nucleic acid encodes for the histone 2B (H2B)-citrine fluorescent protein. The target nucleic acid may encode for any fluorescent protein, however, the target nucleic acid is not limited to proteins or fluorescent proteins. Following and controlling the effects of a nucleic acid of interest allows for further study of molecular and cellular mechanisms in a natural cell and in synthetic biology.

Embodiments of the present invention include methods for controlling the transcription of a target nucleic acid by regulating the recruitment of CRs to the site of transcription of the target nucleic acid in a population of cells. In some embodiments, controlling the transcription includes silencing transcription and may also include silencing of expression. In some embodiments of the present invention, silencing transcription of a target nucleic acid expressed in a population of cells includes recruiting a CR selected from EED, KRAB, DNMT3B, HDAC4, EZH2, REST, or combinations thereof to a site proximal to the transcription initiation site of the target nucleic acid. A cell that is capable of transcribing the target nucleic acid which upon recruitment of a CR as disclosed herein does not transcribe the target nucleic acid is referred to as a "silenced cell." Depending on the selected CR or CR combination as well as the duration of the recruitment (also referred to as the first time period), a percentage of the cells in the population will be silenced. The silencing of the target nucleic acid may be controlled. As shown herein (e.g., FIGS. 5B, 5C) the duration of the CR recruitment will affect the fraction of silenced cells. That is, an increase in the duration of the CR recruitment to a site proximal to the transcription initiation site in this first time period results in an increase in the fraction of silenced cells.

Figure 4C:
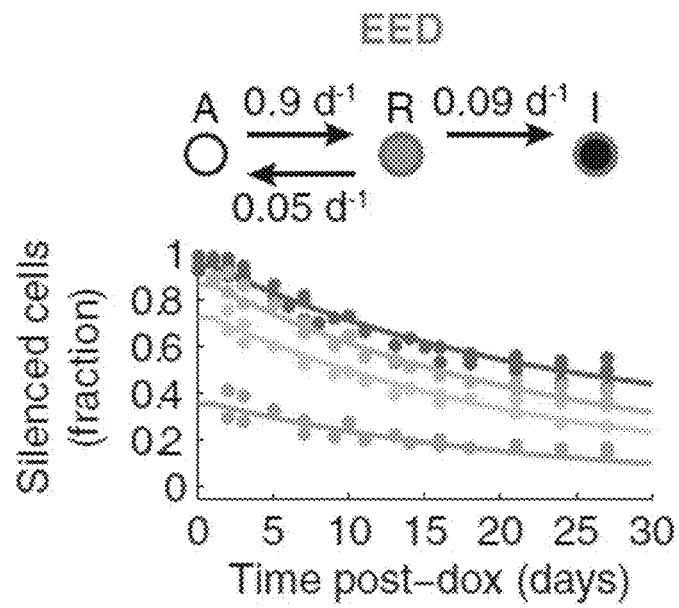
FIGS. 4C, 4D, 4E, and 4F are graphs of the fraction of silenced cells over days after removal of doxycycline (dox) measured using flow cytometry for EED, KRAB, DNMT3B, and HDAC4, respectively, according to embodiments of the present invention and as set forth in the schematic of FIG. 5B, in which the number of recruitment (+dox) days is represented by green (1 day), yellow (2 days), orange (3 days), and red (5 days).
Figure 4D:
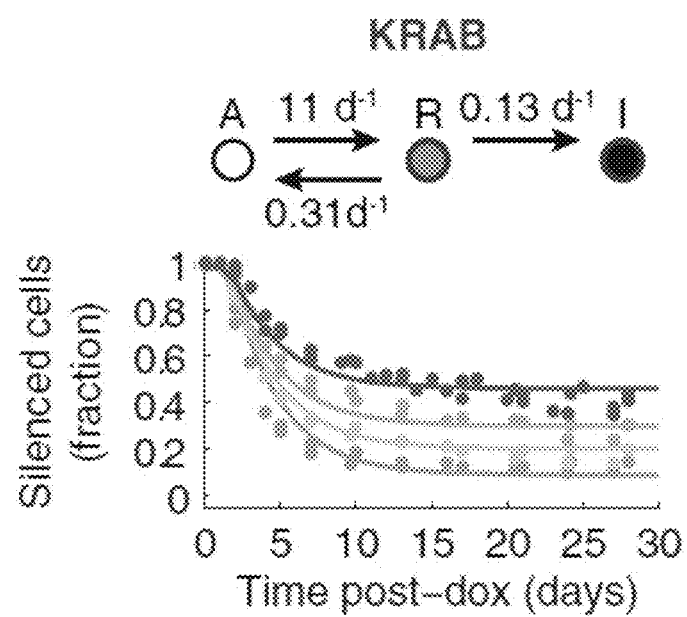
Figure 4E:
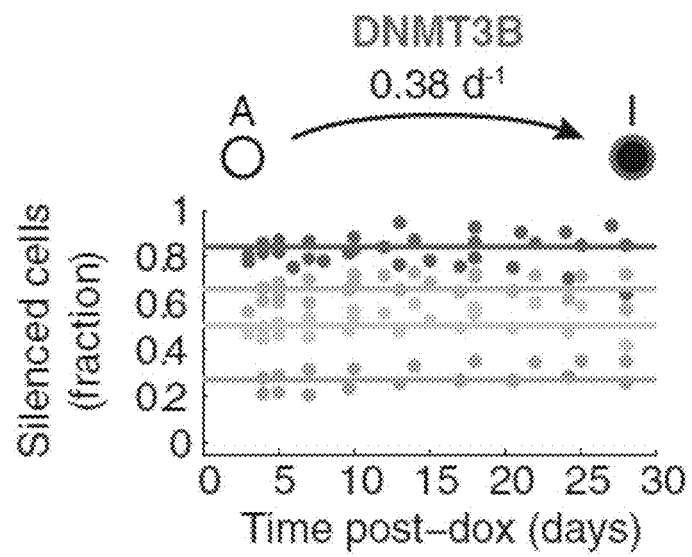
Figure 5A:
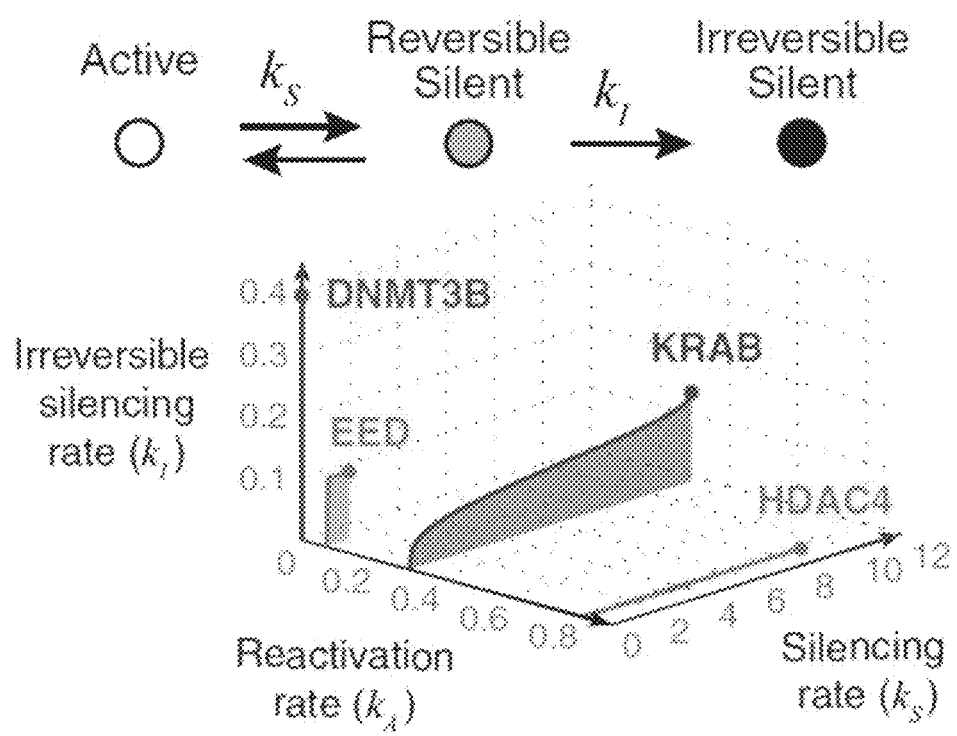
FIG. 5A is a schematic depicting the rate constants for reversible repression of expression (i.e., reversible silent), active expression, and irreversible repression of expression (i.e., reversible silent) over a range of recruitment strengths in which the curve occupied by each CR in the space shown determines its dynamic effects on gene expression and epigenetic memory and the corresponding colored dot at the end of each CR curve represents rate constants at full recruitment strength, according to embodiments of the present invention.
Figure 5B:
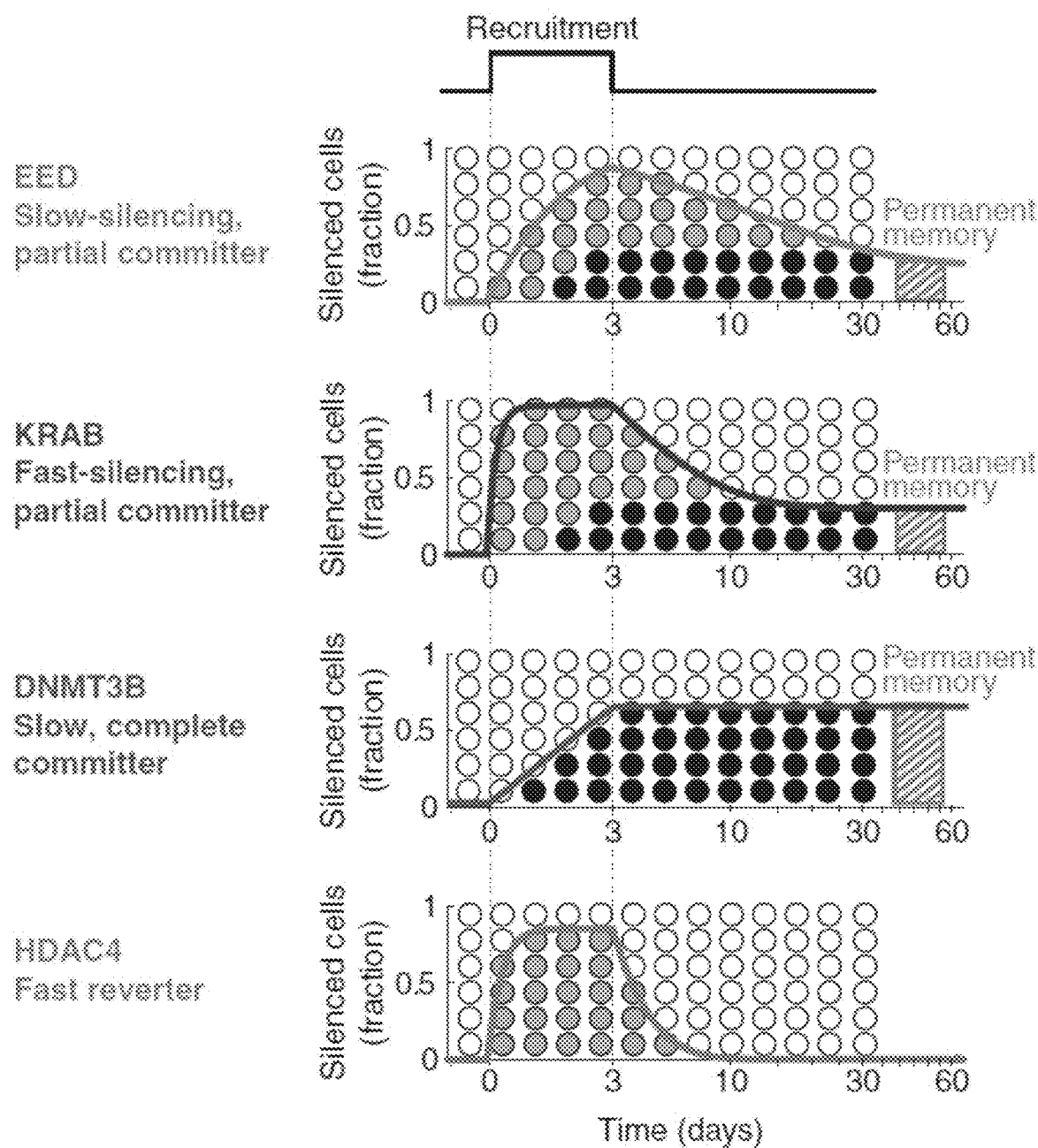
FIG. 5B is a set of four graphs, one for each of EED, KRAB, DNMT3B, and HDAC4 chromatin regulators (CRs) as indicated, showing the amount of silenced cells over 30 days with a recruitment of the respective CR plotted using the rate constants calculated at full recruitment strength for which the total fraction of silent cells in both the R (reversible) (gray circles) and I (irreversible) (black circles) states are indicated by the solid line encompassing both gray and black circles, where the fraction of cells in the I state (permanent memory) is indicated by the far right diagonal lined bar, according to embodiments of the present invention.

Furthermore, in some embodiments of the present invention, the CR-mediated silencing of the target nucleic acid may be permanent (i.e., irreversibly silenced) and maintained as silent in subsequent cell generations. In other words, permanent silencing of the target nucleic acid is not lost in the daughter cells, and is inherited through subsequent cell divisions. For example, silencing of a target nucleic acid using DNMT3B is permanent as shown in FIGS. 5B and 13B. In FIG. 5B, for DNMT3B, cells (black circles) that are silenced during recruitment are permanently silenced (black circles) upon release of recruitment in the second time period (the start of which is indicated by the dotted line). Also, as shown in FIGS. 4E and 13B for DNMT3B, while more cells are silenced with a longer recruitment period (compare red lines at 5 days of recruitment and green lines for 1 day), all cells that are silenced upon CR recruitment stay silenced upon release of recruitment for over 30 days, resulting in the straight horizontal lines as shown. As such, according to embodiments of the present invention, the fraction of cells that is silenced using DNMT3B during CR recruitment will be maintained as silent for transcription of the target nucleic acid after release of the CR at the end of the first period (i.e., start of the second period) in all subsequent cell divisions.

Figure 4F:
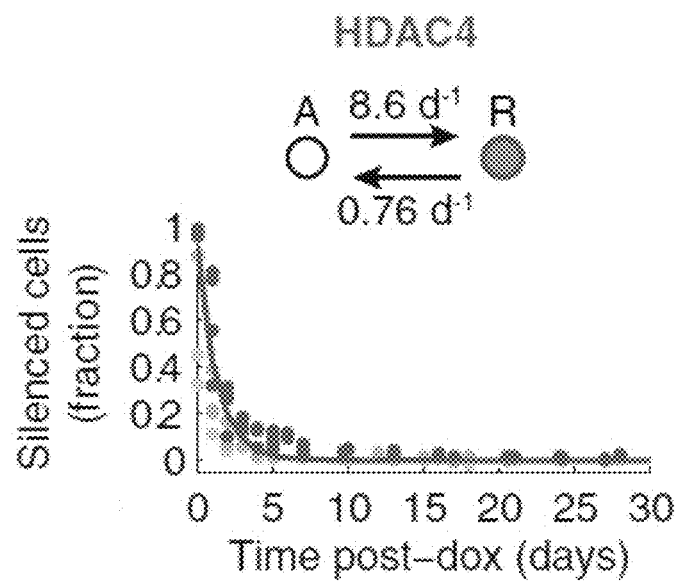

In some embodiments of the present invention, the silencing of the target nucleic acid may be reversible for all cells or approximately all (e.g., up to 95% or up to 99%) cells. For example, silencing of a target nucleic acid upon recruitment of HDAC4 may be reversed upon release of the CR (i.e., at the end of the CR recruitment), as shown in FIGS. 5B, 11C, and 13B. In FIG. 5B, for HDAC4, cells (gray circles) that are silenced during recruitment are reversibly silenced because upon release of recruitment in the second time period (the start of which is indicated by the dotted line), transcription of H2B-citrine resumes, thereby eliminating the number of silenced cells, as shown by the green line decreasing down to zero in the second time period. Also, as shown in FIGS. 4F and 13B for HDAC4, while more cells are silenced with a longer recruitment period (compare red lines at 5 days of recruitment and green lines for 1 day), all cells that are silenced upon CR recruitment resume expression of H2B-citrine upon release of recruitment for over 30 days, resulting in all colored lines decreasing to zero silenced cells as shown. As such, according to embodiments of the present invention, the fraction of cells that is silenced using HDAC4 during CR recruitment are reversibly silent and will resume transcription of the target nucleic acid after release of the CR at the end of the first period (i.e., start of the second period) in all subsequent cell divisions.

In some embodiments of the present invention, the fraction of silenced cells during CR-recruitment includes a first group of previously silenced cells that upon CR release are capable of transcribing the target nucleic acid and a second group of previously silenced cells that upon CR release maintain their silenced state. The percentage of previously silenced cells that are in the first group versus the second group may be controlled by the duration of the recruitment time (first time period) as shown and depicted in FIGS. 4A, 5A, and 5B. For example, in FIG. 5B, silencing of a target nucleic acid upon recruitment of EED, KRAB, and EZH2, and upon release of the CR (second time period) results in some reversibly silent cells (gray circles) and some irreversibly silent cells (black circles) for which the number of irreversibly silent cells increases as the number of days of CR recruitment increase as shown in FIGS. 4C and 4D with reference to FIG. 4B and FIG. 17B with reference to FIG. 17A.

In some embodiments of the present invention, one of DNMT3B, HDAC4, EED, KRAB, and EZH2 may be expressed in various combinations in a cell. The recruitment of the CRs in combination may be fused to the same DNA binding domain to transcribe the same target nucleic acid. In some embodiments, the CRs in combination may be fused to a different DNA binding domain to regulate the transcription of the same target nucleic acid or two different target nucleic acids. An example of HDAC4 and EED recruitment was performed simultaneously in the same cell for expression of H2B-citrine expression, the results of which are shown in FIGS. 18A, 18B, and 18D.

The following Examples are presented for illustrative purposes only, and do not limit the scope or content of the present application.

EXAMPLES

Reference is made to the materials and methods including the Supplemental Material of Bintu et al., 2016, *Science*, 351:720, DOI: 10.1126/science.aab2956, the entire contents of which are incorporated herein by reference.

Example 1

Figure 1D:
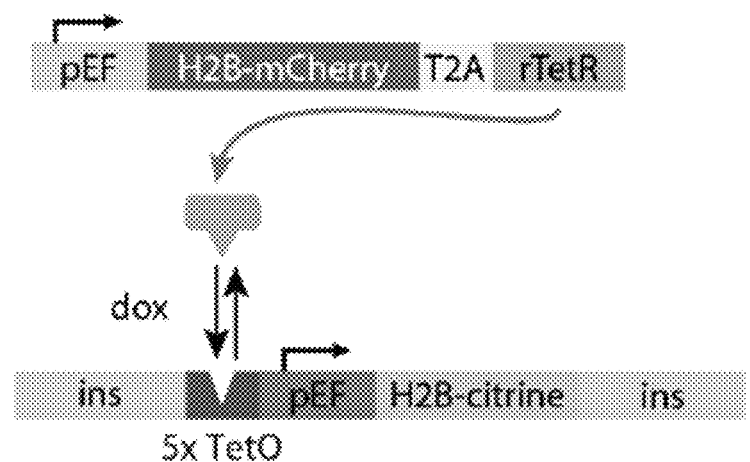
FIG. 1D is a schematic depicting a control cloning construct similar to the construct shown in FIG. 1B except the rTetR is not fused with a chromatin regulator (CR) in order to test whether recruitment of rTetR alone has any effect on reporter expression, according to embodiments of the present invention.
Figure 1E:
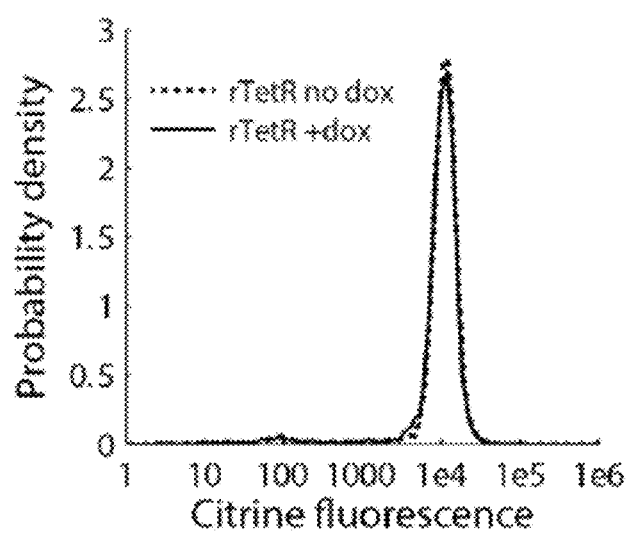
FIG. 1E shows a graph of citrine fluorescence levels in reporter cells measured in the presence (+dox) and absence of doxycycline (no dox) by flow cytometry, in which the amount of citrine fluorescence expression was the same under both conditions, indicating that rTetR recruitment alone as depicted in FIG. 1D, does not repress gene expression.
Figure 2A:
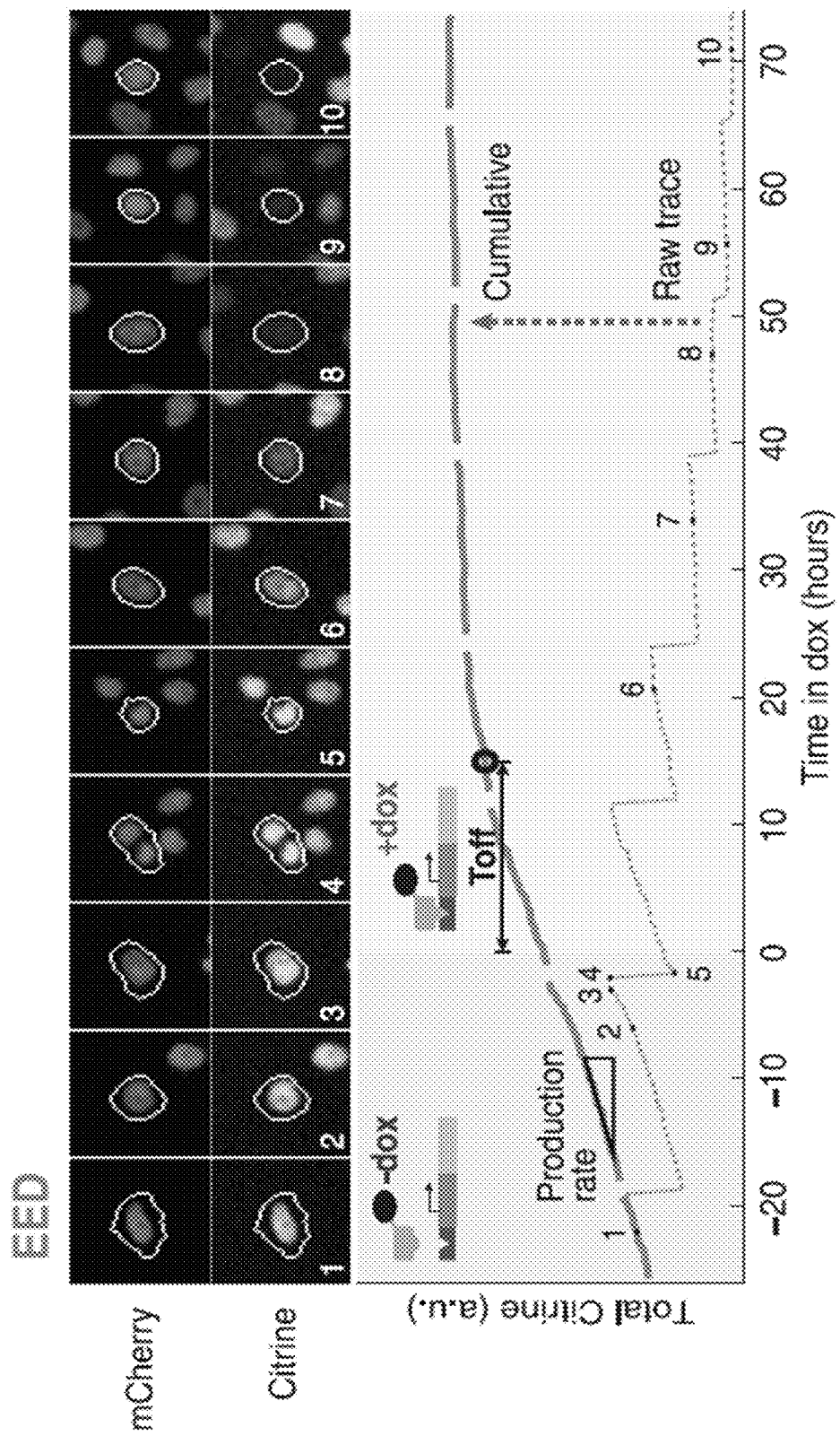
FIG. 2A shows a filmstrip sequence of a video (movie) of silencing dynamics in the presence of EED, according to embodiments of the present invention, in which total citrine fluorescence is plotted as the dotted line for the cell lineage circled in white, before (gray shading) and during (yellow shading) recruitment, where a cumulative fluorescence trace (solid cyan) was obtained by computationally restoring the fluorescence signal lost to the sister cell at each division; where this procedure facilitates continuous quantification of reporter production rate (slope of cumulative trace) and identification of silencing events (black circles), as disclosed herein, in which the numbers shown correspond to frames in the video filmstrip.
Figure 2B:
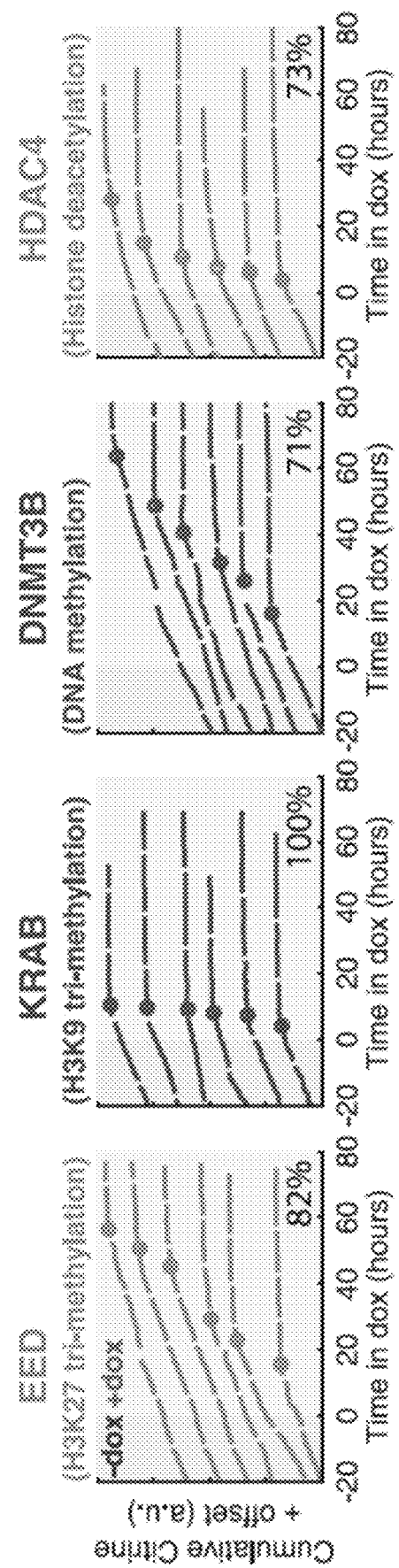
FIG. 2B shows representative single-cell traces of silencing events (circles) obtained during a video as described in FIG. 2 induced by recruitment of the indicated CR (EED, KRAB, DNMT3B, and HDAC4), in which only cells silenced during the video are shown and in which, for clarity, traces are offset by arbitrary amounts on the y-axis, and the percentage of traces that resemble those shown here is indicated on each plot.
Figure 6A:
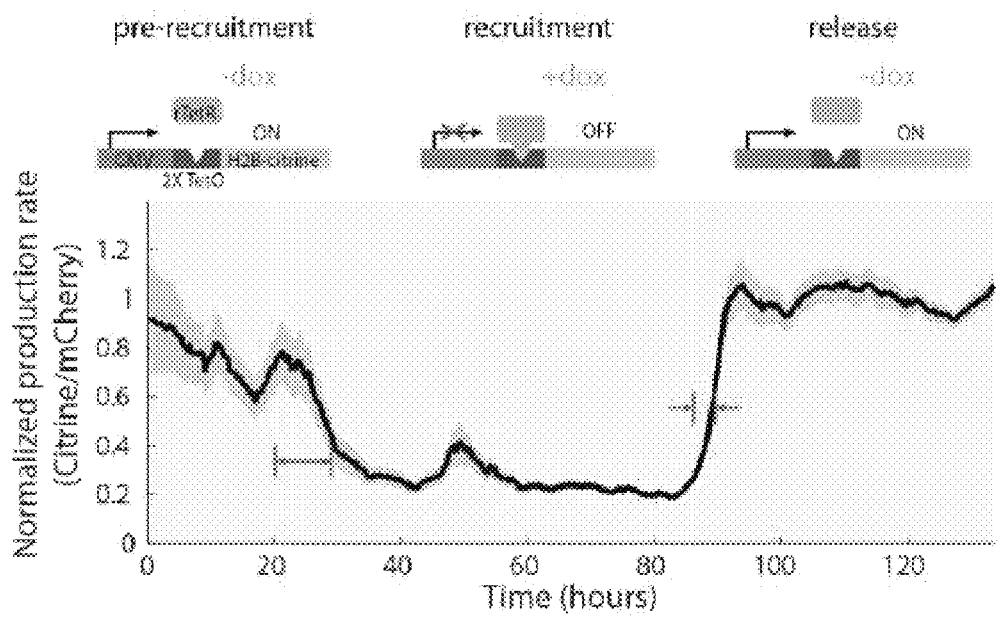
FIG. 6A shows a schematic (upper panel) of an expression construct in a cell line containing the rTetR domain alone recruited to a cytomegalovirus (CMV) promoter followed by 2 TetO sites for measuring the response time for pre-recruitment, recruitment, and release (derecruitment) as indicated, for which binding of rTetR directly represses expression by acting as a transcription roadblock; where the changes in reporter production rates were measured using time-lapse microscopy (lower panel), for which the mean Citrine production rate from FIG. 2A was calculated as a function of time (black curve) by averaging over single-cell traces at each time point, where since cells were undergoing division, the number of traces analyzed for each time point varied between 62 cells for the first time point to 926 cells for the last time point; the gray shading above and below the curve represents the standard error of measurement (SEM); addition of dox resulted in a reduction in gene expression within 8±2 hours as indicated with the red arrows and removal of dox relieved this repression within 2.5±2 hours as indicated with the green arrows, according to embodiments of the present invention.
Figure 6B:
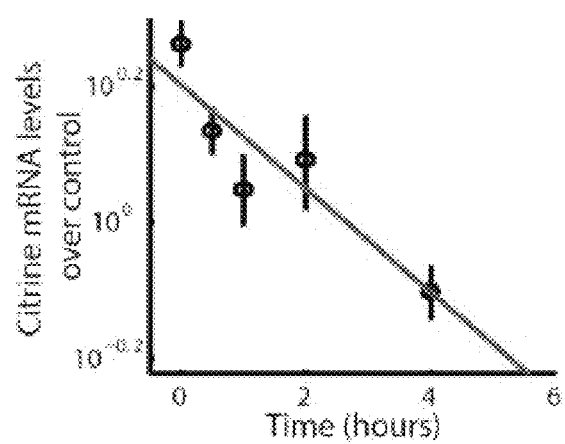
FIG. 6B is a graph, according to embodiments of the present invention, showing the half-life of Citrine mRNA measured by inhibiting transcription with actinomycin D (5 ug/ml) and then following the levels of mRNA as a function of time, where these values were measured by quantitative PCR (qPCR) and normalized against a constant amount of mCherry mRNA spiked in as an internal control; whereby fitting these data to an exponential decay (red line), the half-life of the reporter mRNA was determined to be 3.9 hours (with a 95% confidence interval of [0.9, 4.3] hours).

Reversible and Permanent Expression Silencing with Chromatin Regulators. Methods according to embodiments of the present invention are shown in the following examples using the EED, KRAB, DMNT3B, HDAC4, EZH2, and REST chromatin regulators (CRs) fused to a reversible tetracycline repressor (rTetR) protein to track the effects of these CRs on a target nucleic acid (e.g., gene) in individual cells. More specifically, the CRs were fused to reverse tet repressor (rTetR) as disclosed in Urlinger et al., 2000, *PNAS*, 97:7963-7968, the entire contents of which are herein incorporated by reference. The rTetR protein binds to DNA only in the presence of doxycycline (dox), providing control of the timing and duration of CR recruitment upstream of a fluorescent reporter gene expressing histone 2B (H2B)-Citrine (FIGS. 1B-1C). The reporter was randomly integrated into the genome of Chinese hamster ovary (CHO)-K1 cells (FIG. 1B) or was integrated on a human artificial chromosome (HAC) (FIG. 1C). All constructs were stably integrated in the CHO-K1 cells, a major model system for synthetic mammalian biology. Each cell line constitutively co-expressed H2B-mCherry, allowing cell tracking even when the reporter was silenced (FIGS. 1C, 2A). Control experiments indicated that recruitment of rTetR alone does not repress reporter expression (FIGS. 1D-1E), and that changes in gene regulation could be detected over timescales as short as 6 hours (FIGS. 6A-6B). Thus, this system enables analysis of the effects of recruitment and release of each CR on gene expression in individual cells.

Figure 7B:
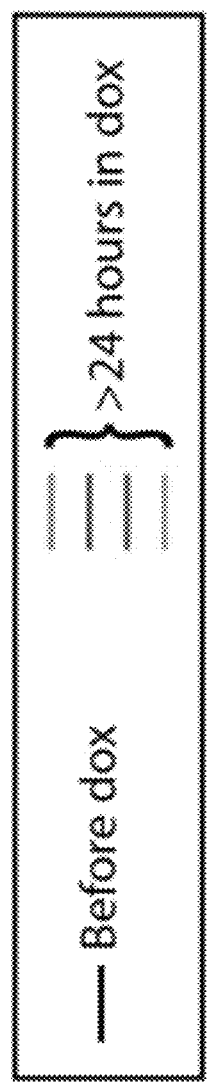
FIG. 7B shows graphs of the cell silencing effects for each chromatin regulator as indicated (EED, KRAB, DNMT3B, HDAC4) as a function of citrine reporter production before doxycycline (dox) and after 24 hours of dox, showing that production rates in most silenced cells collapse to a peak around zero, according to embodiments of the present invention.
Figure 7B:
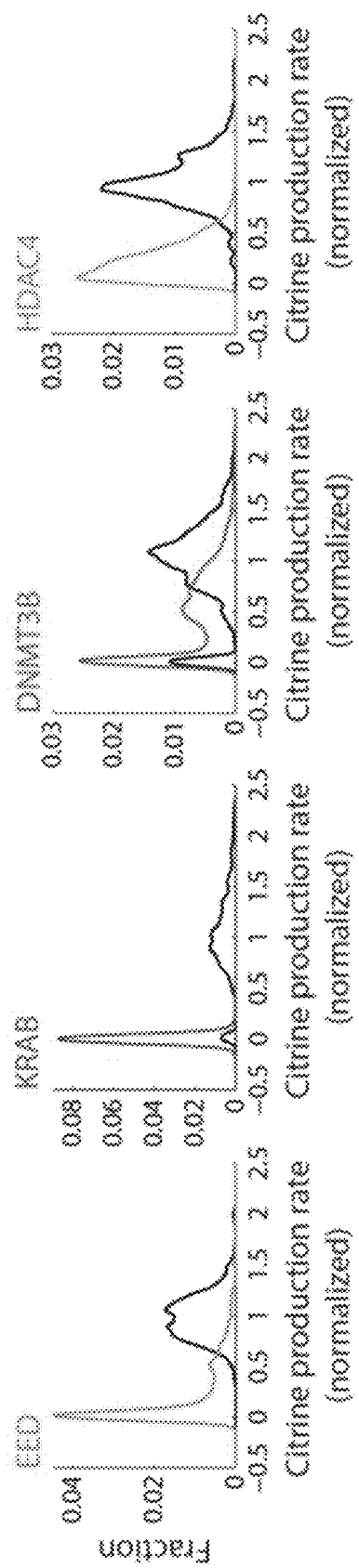
Figure 7C:
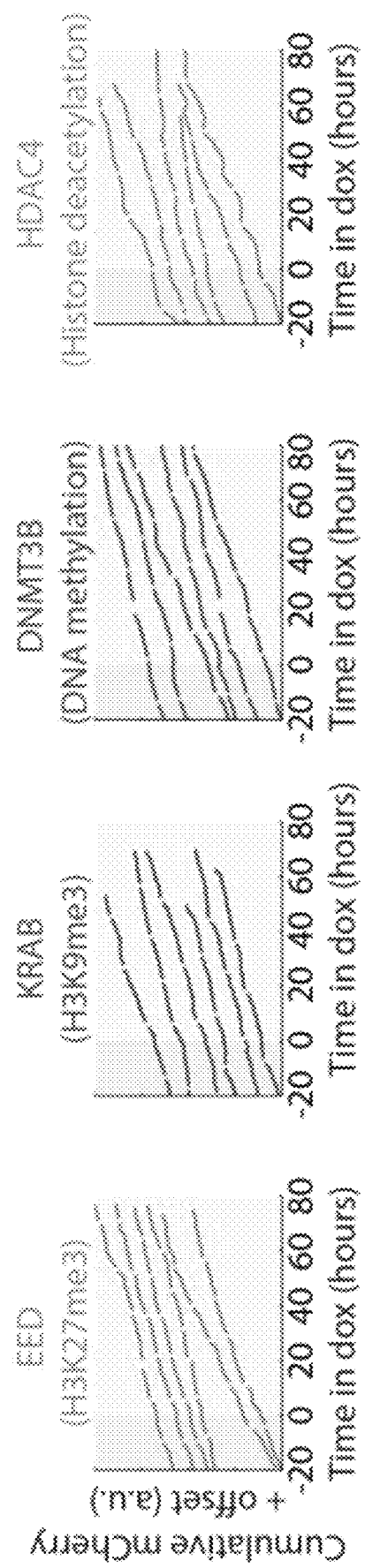
FIG. 7C shows graphs of single-cell fluorescence traces, according to embodiments of the present invention, for each of EED, KRAB, DNMT3B, and HDAC4 as indicated in the constitutive reporter H2B-mCherry channel of the same cell lineages as shown in FIG. 2B and arranged in the same order where traces are vertically offset for clarity; the control H2B-mCherry reporter showed steady production in all traces, indicating that dox-mediated silencing is likely specific to the H2B-Citrine reporter locus rather than a genome-wide effect.
Figure 8:
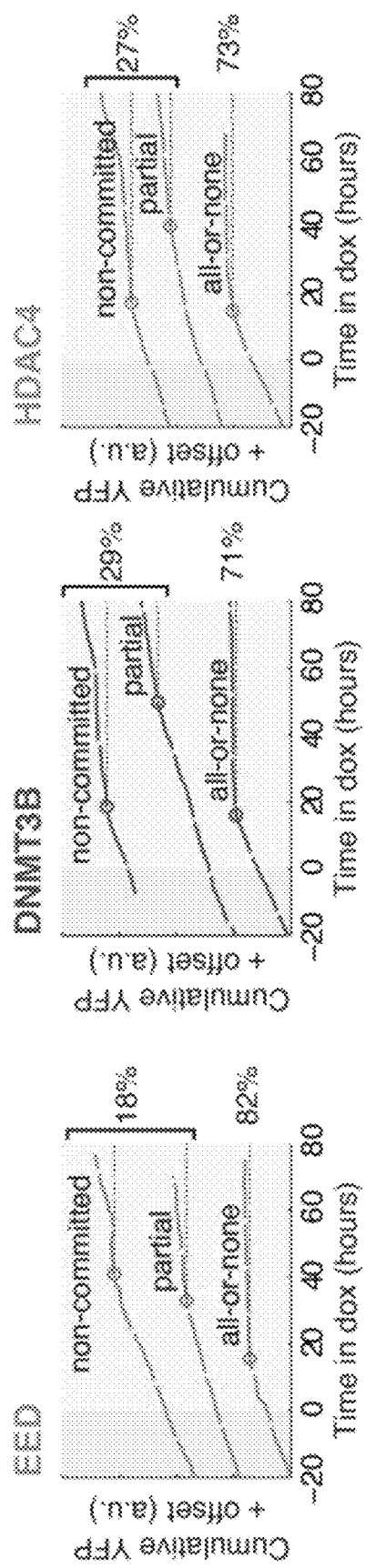
FIG. 8 shows graphs of silencing dynamics that deviated from all-or-none behaviors for each of EED, DNMT3B, and HDAC4 as indicated (no deviations were observed for KRAB), according to embodiments of the present invention, where for each graph, a representative example trace is shown for each of two types of non-typical behaviors, with observed frequencies indicated by percentages relative to all traces; partial silencing events are defined as traces that show reduced by not fully silenced expression and these are defined by a lack of full silencing within 1.5 cell cycles after the initial silencing event (middle trace); non-committed silencing events are those in which a strong silencing event is followed by a subsequent increase in activity (top trace); circles indicate detected silencing events and a comparative all-or-none silencing events is represented by the bottom trace.

To analyze how recruitment of each CR alters gene expression, time-lapse microscopy was used to follow silencing in individual cells after addition of dox (FIG. 2A). Recruitment of each CR strongly and specifically silenced H2B-Citrine expression (FIGS. 2B, 7B-7C), after hours or days as shown (FIGS. 2B-2C, 2G-2H). Silencing occurred in an all-or-none fashion in individual cells for EED, KRAB, DNMT3B, and HDAC4 (FIG. 2B), with median production rates dropping below 20% of their pre-silencing value within approximately 20 hours, or about one cell cycle (FIGS. 2D-2E; see also FIG. 8 for deviations from this behavior).

Figure 2C:
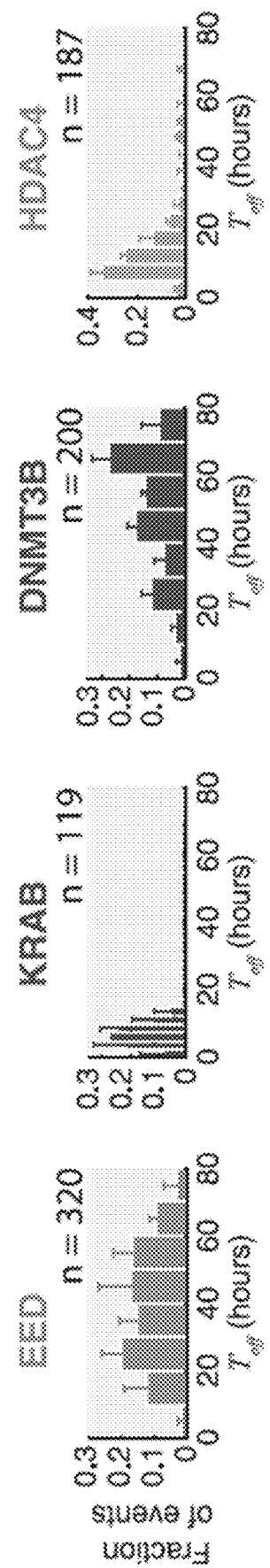
FIG. 2C shows the distributions of silencing times, $T_{off}$ (mean±s.d.) corresponding to the recruitment and silencing events of FIG. 3A, in which the number of events in each histogram, n, is indicated in each graph.
Figure 2D:
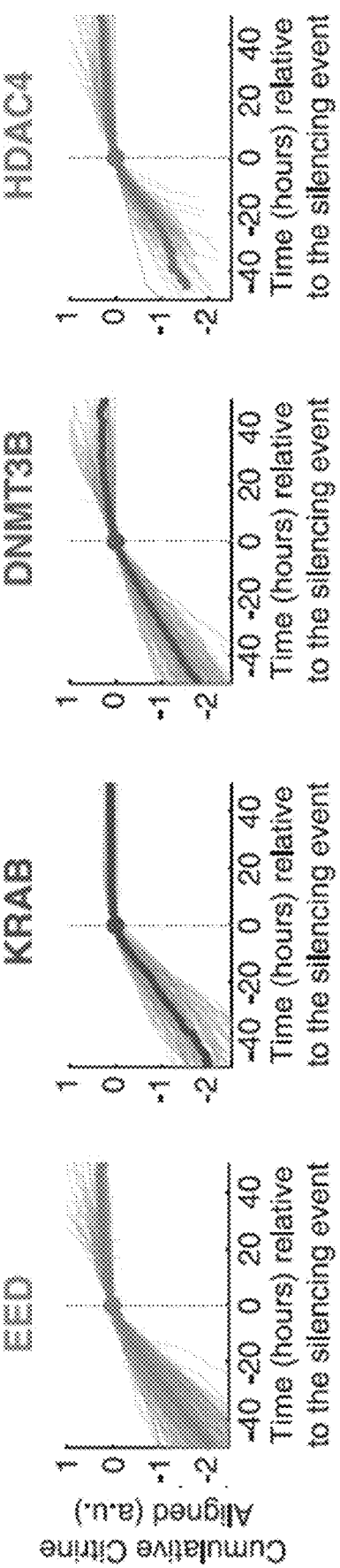
FIG. 2D shows graphs of single-cell cumulative fluorescence traces (gray lines) aligned at the silencing event (0 on the x-axis) and superimposed, according to embodiments of the present invention, in which the median of all traces is plotted for each CR as a colored line (EED in cyan, KRAB in blue, DNMT3B in red, and HDAC4 in green).
Figure 2E:
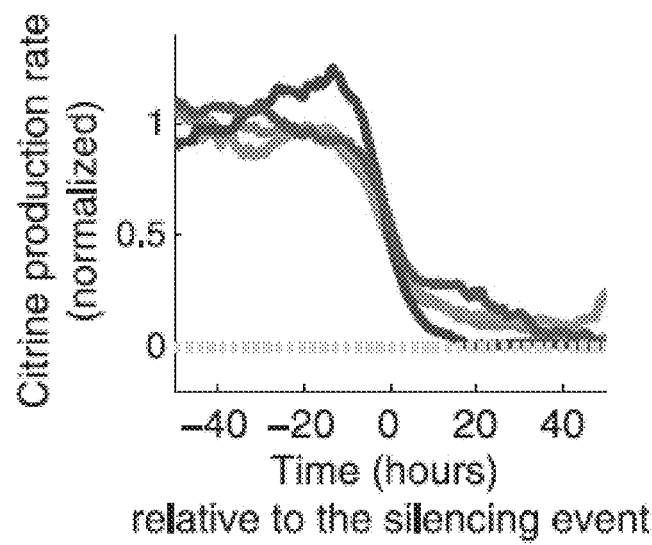
FIG. 2E is a graph of the median reporter production rates obtained from all the slopes of the individual traces in FIG. 2D, showing the all-or-none nature of silencing events for each CR: DNMT3B (red), EED (cyan), HDAC4 (green), and KRAB (blue), according to embodiments of the present invention.
Figure 2F:
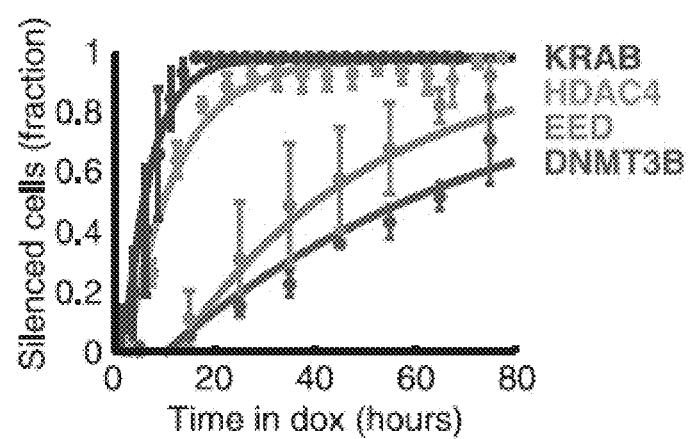
FIG. 2F is a graph showing the fraction of cells (indicated with dots, mean±s.d.), silenced as a function of time, for each CR: DNMT3B (red), EED (cyan), HDAC4 (green), and KRAB (blue), according to embodiments of the present invention, and the curved lines represent exponential fits to a single silencing rate with a time delay for each CR, as disclosed herein.
Figure 2G:
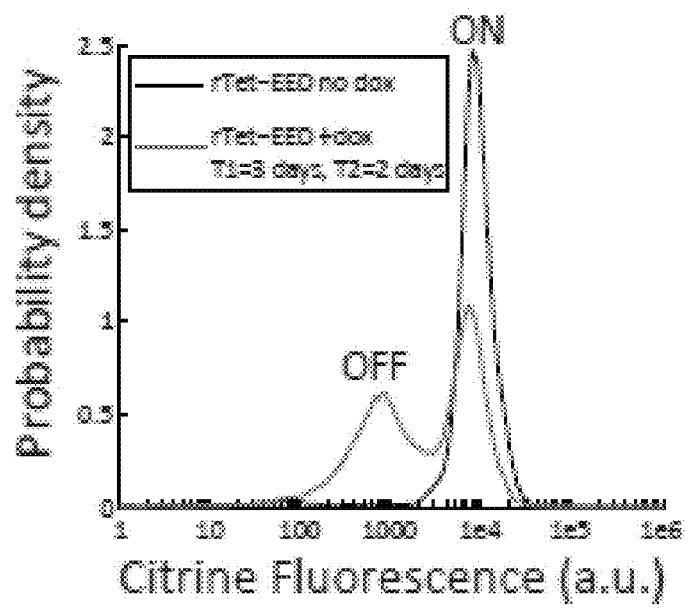
FIG. 2G is a graph showing citrine fluorescence measured by flow cytometry corresponding to gene expression of the reporter as depicted in FIG. 1B after T1=3 days and T2=2 days (purple), and with no dox as a control (black).
Figure 2H:
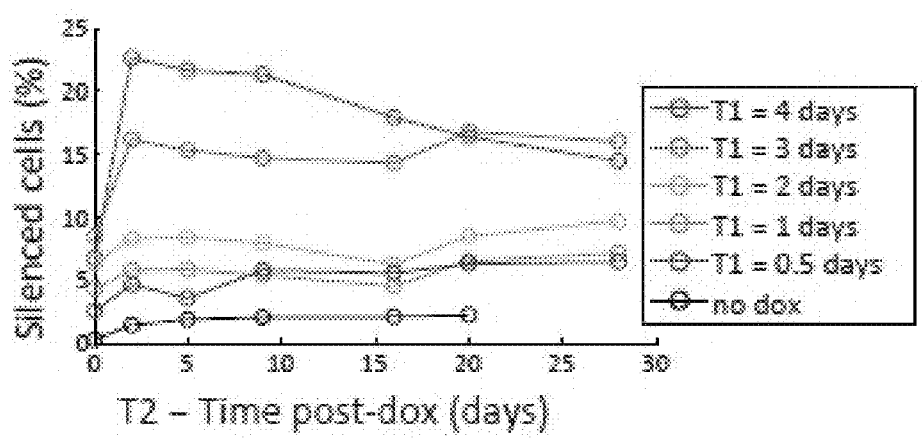
FIG. 2H is a graph plotting the percentage of silenced cells as a function of time post-dox (T2, release) for different periods of dox induction (T1, recruitment) corresponding to the cell line depicted in FIG. 1B.
Figure 9:
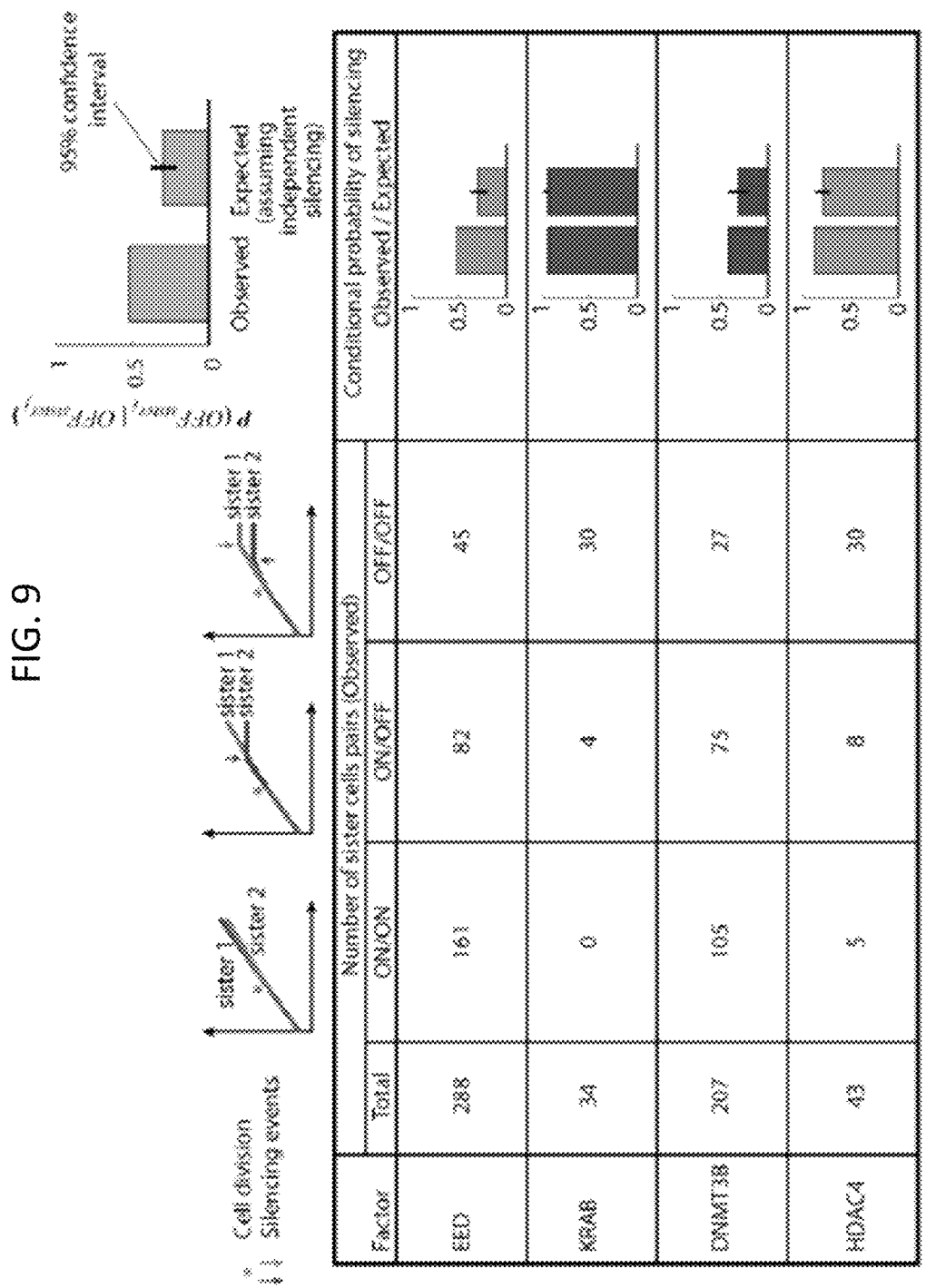
FIG. 9 shows analyses of sister cell correlation during silencing according to embodiments of the present invention. The numbers of sister cell pairs originating from an actively expressing parent cell were tabulated and their silencing behavior in the first cell cycle after division was compared with the parent cell where for each factor, the number of sister pairs in which both sister cells remained active (ON/ON column), only one sister cell was silenced (ON/OFF column), and both sister cells were silenced (OFF/OFF column). From these observations, the conditional silencing probability of a sister cell was computed given the other sister cell is silenced, i.e., $$P(OFF_{sister_i} \mid OFF_{sister_j}) = \frac{2*OFF/OFF}{2*OFF/OFF + ON/OFF},$$

In contrast to the overall similarity in silencing event profiles, the timing of silencing events varied between cells, and the rate of silencing depended strongly on the CR used (FIGS. 2C, 2F). Silencing by KRAB and HDAC4 was rapid, with all cells silenced within one cell cycle (approximately 20 hours), whereas EED and DNMT3B showed slower rates of silencing, reaching 50% of cells silenced at 35 and 62 hours, respectively. For these CRs, the broad cell-cell variability in $T_{off}$, defined as the delay between dox addition and silencing (FIG. 2C), and the lack of a strong correlation of silencing behavior between sister cells (FIG. 9) indicate that chromatin silencing is a stochastic process. In fact, after a relatively small time lag, the fraction of silenced cells as a function of time is well-described by a single-rate process for each CR (solid lines, FIG. 2F). Together, these results indicate that silencing occurs through stochastic, all-or-none events at distinct rates for each CR.

To analyze how the CRs differed in terms of reactivation dynamics and epigenetic memory, the dox was washed from the cells to release the CRs after 5 days of recruitment, and the resulting changes in gene expression was tracked in time-lapse movies, the images of which are shown in FIGS. 3A, 10A-10B. For EED, KRAB and HDAC4, reactivation occurred in stochastic all-or-none events, resembling silencing events in reverse (FIG. 3B). In contrast, no reactivation events occurred in cells silenced by DNMT3B recruitment, up to 80 hours after dox removal, after which cell density became too high for tracking.

Figure 3D:
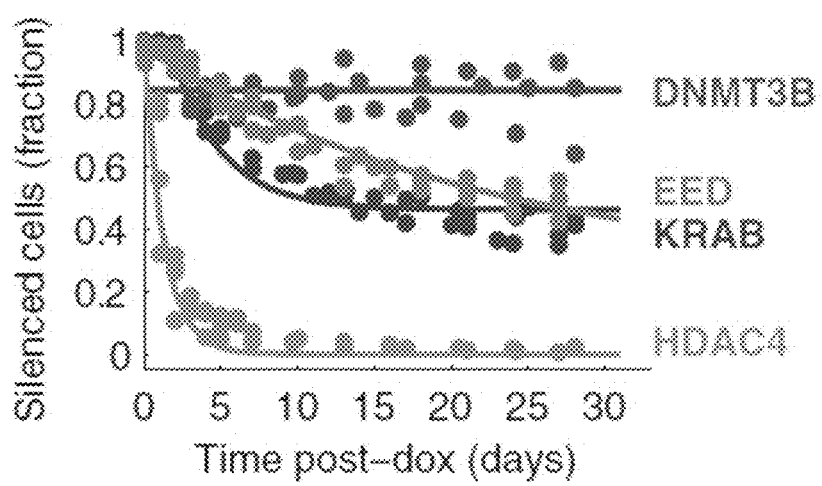
FIG. 3D is a graph of the fraction of silenced cells measured by flow cytometry at various time points (days) after CR release for which data from three independent experiments for each CR is shown with HDAC4 in green, KRAB in blue, EED in cyan, and DNMT3B in red, according to embodiments of the present invention, where the spontaneous background silencing rates have been subtracted and the solid lines are fits to the model shown in FIG. 5A.

To extend these measurements to longer durations, the cells expressing citrine were monitored by flow cytometry. As expected for all-or-none reactivation, distributions of total fluorescence were bimodal (FIGS. 3B, 11A-11C), allowing for quantitative tracking of the fraction of silent cells as a function of time (FIGS. 3D, 11D). The CRs produced qualitatively different modes of epigenetic memory (FIG. 3D), associated with distinct sets of chromatin modifications as measured by DNA and chromatin immunoprecipitation and qPCR (FIG. 12A-12B). HDAC4 imparted short-term memory, where upon release of CR (at the end of recruitment), silencing was lost (reversed) in all cells within five days, consistent with rapid dynamics of histone acetylation/deacetylation. In contrast, DNMT3B produced long-term memory where cells were irreversibly or permanently silenced for the duration of the experiment (30 days), in agreement with reports that DNA methylation is stably inherited as reported in Bird, 2002, *Genes Dev.* 16:6-21, the entire contents of which is incorporated by reference. Finally, both EED and KRAB enabled a novel type of hybrid memory that is not associated with DNA methylation (FIG. 12B). For these CRs, a fraction of the silenced cells fully reactivated within 2-3 weeks, whereas the remaining fraction of the silenced cells remained completely silenced for at least a month.

The hybrid memory could be explained by a model (FIG. 4A) in which recruitment of a silencing CR causes cells to stochastically advance from the actively expressing state (A) to a reversibly silent state (R), and then to an irreversibly silent state (I). It is assumed that after the end of recruitment, the forward silencing rates become negligible, allowing cells in the R state to revert to the A state, reactivating gene expression, while cells in the I state remain silenced.

This 3-state model predicts that longer durations of recruitment should increase the fraction of irreversibly silenced cells. To test this model, the duration of recruitment was varied and the subsequent reactivation dynamics were analyzed (FIG. 4B). For both EED and KRAB, the fraction of cells remaining silent after 30 days of CR release increased with the duration of the initial recruitment, as presented in the 3-state model (FIGS. 4C, 4D). Aside from a relatively small time lag before the onset of reactivation (1-2 days), all data for a given CR could be fit to the 3-state model with a single set of rate constants across the entire range of recruitment durations (solid lines, FIGS. 4C-4D). Moreover, simplified forms of this model can also explain the behavior of HDAC4 and DNMT3B, each requiring only 2 of the 3 states (FIGS. 4E-4F).

Figure 4G:
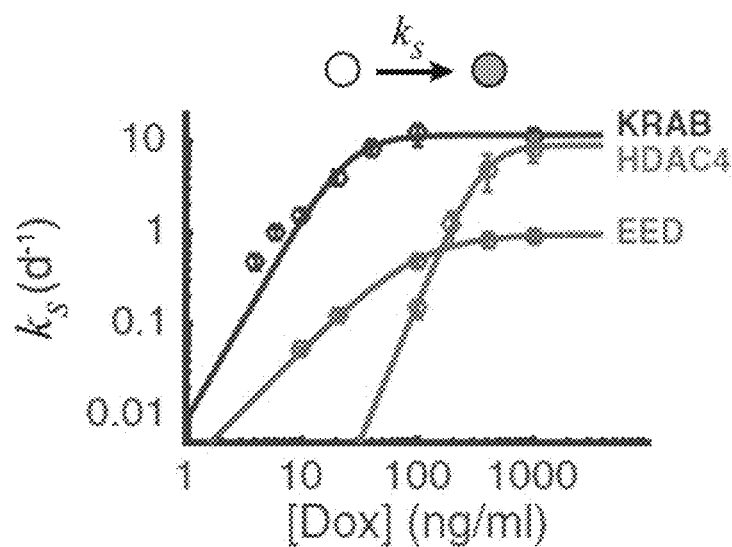
FIGS. 4G, 4H, and 4I are graphs showing the influence of the concentration of doxycycline on the silencing rate constant ($k_S$), the reactivation rate constant ($k_A$), and the irreversible rate constant ($k_I$), respectively, in which for each concentration, the data are fit with the corresponding model for each CR to extract the kinetic rates indicated in the diagram, where error bars represent 95% confidence interval (CI) of the fit and the curves of FIGS. 4G and 4I are fits to a Michaelis-Menten equation and lines in FIG. 4H are fits to a constant value, as disclosed herein, according to embodiments of the present invention.
Figure 4H:
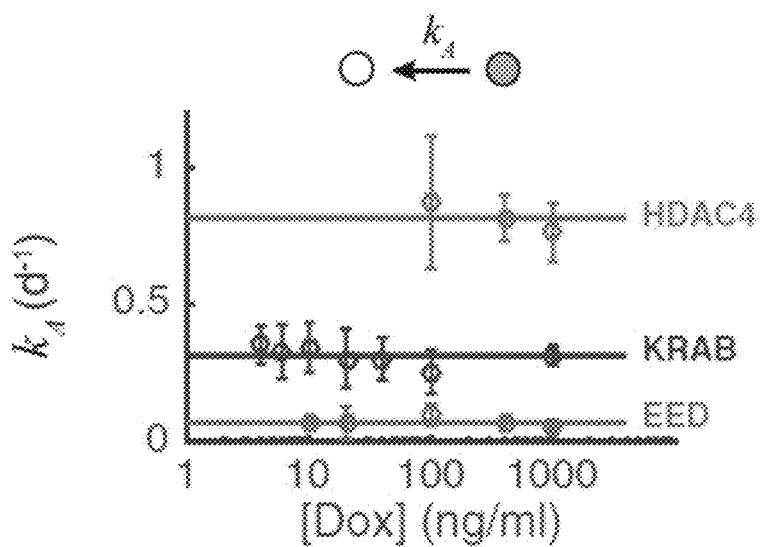
Figure 4I:
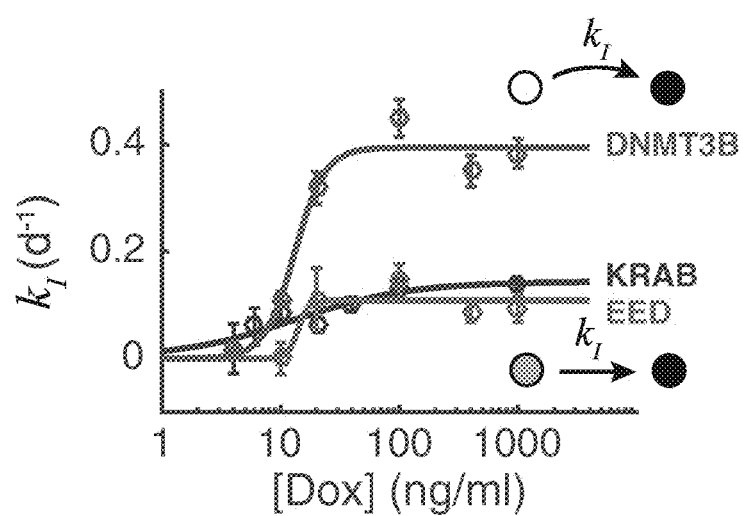

A key parameter in these experiments is the recruitment strength of the CR, which is controlled by dox concentration. To understand how recruitment strength affects silencing and reactivation capabilities, the effects of 5 days of CR recruitment were analyzed for a range of dox concentrations. Qualitatively, each CR produced the same number and type of states across dox concentrations (compare FIGS. 4C-4F and FIG. 13B). Quantitatively, recruitment strength modulated the silencing rates, but not the reactivation rates, which depended only on the identity of the silencing CR (FIGS. 4G-4I). Together, these data provide a comprehensive view of how the dynamic effects of each CR on gene expression depend on recruitment duration and strength.

The 3-state model (FIG. 4A) provides a unifying framework for comparing the operational capabilities of different CRs. For a given genomic context, cell type and promoter architecture, each CR traces a unique curve within the parameter space defined by the three rate constants of the model over a range of recruitment strengths (FIG. 5A). This operational view of CRs is complementary to mechanistic and genome-wide studies. At the same time, stochastic silencing and reactivation may be related to molecular models based on spreading of chromatin modifications (FIG. 14).

Figure 5C:
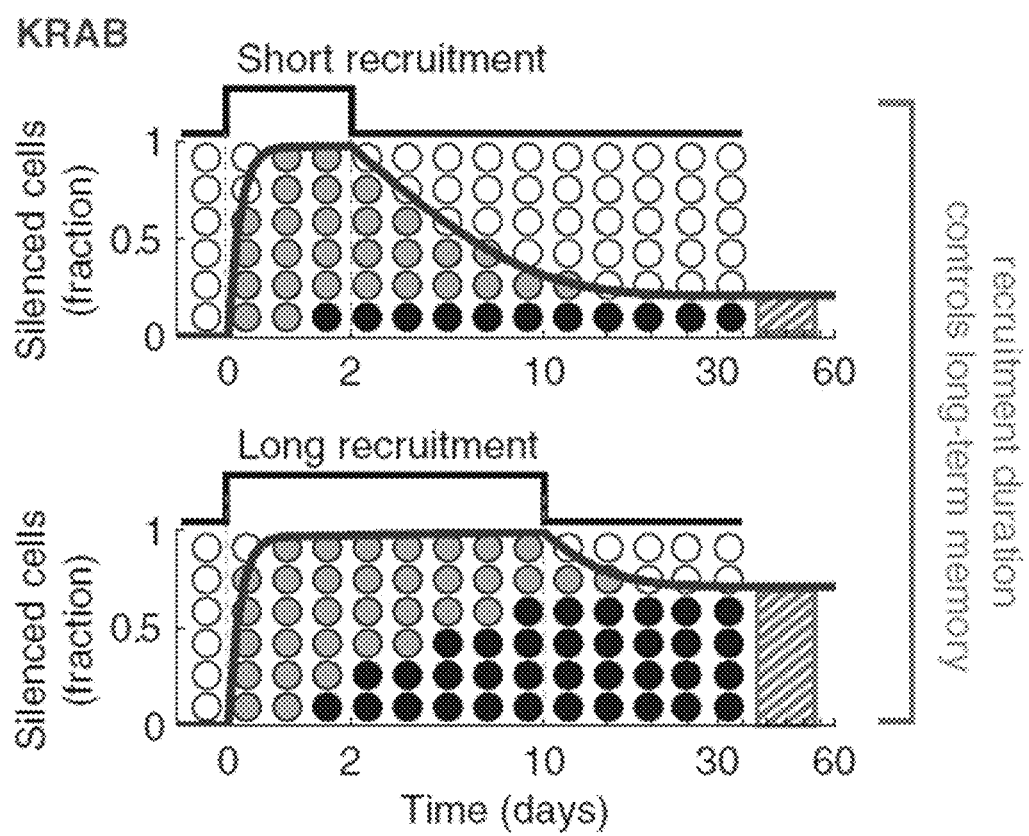
FIG. 5C is a set of two graphs representing the recruitment of KRAB in cells in which the upper graph shows the effects on reversibility of repressed gene expression after 2 days of doxycycline-induced KRAB recruitment and the lower graph shows the effects on reversibility of repressed gene expression after 10 days of doxycycline-induced KRAB recruitment, where longer recruitment results in more irreversibly repressed gene expression, according to embodiments of the present invention.

Despite their differences, the CRs analyzed here were all capable of regulating gene expression through duration-dependent fractional control. In this mode, the duration of CR recruitment controls the fraction of cells in which the target gene is silenced in an all-or-none fashion. This is possible when the lifetime of the reversible silenced state is long compared to the lifetimes of mRNA and protein (FIG. 15A-15E). Duration-dependent fractional control may be contrasted with other transcriptional regulation systems, in which more rapid dynamics enables the occupancy of a transcription factor at the promoter to control protein expression levels in a graded manner. Due to their different parameters, each CR generates a distinct control mode (FIG. 5B): DNMT3B faithfully records the duration or strength of recruitment; HDAC4 enables fast and reversible fractional control at maximum recruitment strengths, but can also lead to graded changes in protein levels at lower ones (FIGS. 15A-15E), and EED and KRAB, due to their hybrid memory, enable regulatory capabilities across multiple timescales. For example, according to some embodiments of the present invention, with these CRs, pulses of recruitment of different durations that both silence the entire population in the short term, establish different degrees of permanent memory in the longer term (FIG. 5C). These types of fractional control strategies may be used to integrate signals for cellular decision-making.

In addition to the EED, KRAB, DNMT3B and HDAC4, the chromatin regulators EZH2, REST, HDAC3 and RNF2 (RING1B) were also analyzed (FIGS. 16A-16D). For both EZH2 (part of PRC2) and REST, all-or-none silencing of most cells was observed after 5 days of recruitment, and no silencing was observed upon HDAC3 recruitment, and very little silencing with RNF2.

Silencing experiments for combined recruitment of HDAC4 and EED as shown in FIGS. 18A-18D were performed with a CHO-K1 cell line that is a stable monoclonal for the Citrine reporter and HDAC4, and a stable multiclonal for EED. This cell line was created as follows: First, the PhiC31-Neo-ins-5×TetO-pEF-H2B-Citrine-ins reporter was integrated in the HAC, and pEF-H2B-mCherry-T2A-rTet-HDAC4 was inserted by random integration, as described herein. Subsequently, pEF-H2B-Cerulean-T2A-rTet-EED-IRES-Blast was randomly integrated into this reporter line by transfection with Lipofectamine 2000 (Invitrogen). These cells were selected using 10 µg/ml blasticidin starting 24 hours after transfection for a total of 14 days. For all flow cytometry experiments, cells were first gated for cerulean expression. All other experimental details and analysis are similar to those performed for EED.

Example 2

Plasmid construction. The PhiC31-Neo-ins-5×TetO-pEF-H2B-Citrine-ins reporter construct (FIG. 1B) was assembled using a backbone containing the PhiC31 attB site, a neomycin resistance gene, and a multiple cloning site flanked by two 1.2 kb chicken HS4 insulators on each side (phiC31-Neomycin-2×cHS4ins-MCS-2×cHS4ins), as described in Yamaguchi et al., 2011, *PLOS ONE*, 6:e17267, the entire contents of which are herein incorporated by reference. Three elements of the reporter were PCR amplified from the following sources: five Tet binding sites from the TRE-tight plasmid (Clontech), pEF from pEF/FRT/V5-Dest (Life Technologies), and H2B-citrine from pEV2-12×CSL-H2B-Citrine, as described in Sprinzak et al., 2010, *Nature*, 465: 86-90, the entire contents of which are herein incorporated by reference. These components were first sequentially cloned into the pExchange1 backbone using standard molecular biology techniques. The entire TRE-pEF-H2B-citrine was then PCR-amplified and combined by Gibson assembly with the phiC31-Neomycin-2×cHS4ins-MCS-2× cHS4ins backbone cut by AvrII. This construct was designed such that after integration, the neomycin gene would be expressed from a PGK promoter situated upstream of the phiC31 site in the HAC, as described in Yamaguchi et al., 2011, supra. The PhiC31 integrase was a gift from the Oshimura Lab.

The plasmids containing the rTetR-CR fusions were built using Gibson assembly of the pExchange1 backbone containing the pEF promoter (cut with BamHI and KpnI), H2B-mCherry (PCR-amplified from a derivative of pEV-12×CSL-H2B-mCherry as described in Sprinzak et al., 2010, supra), rTetR (PCR-amplified from rtTA3 system, Clontech), and a PCR product for each CR. The source plasmids encoding the CRs were as follows: pCMV-HA-EED (Addgene 24231), HDAC4 Flag (Addgene 13821), DNMT3B cDNA (isoform 5, OpenBiosystems MMM1013-99827219), and PSV40-E-KRAB-pA (pWW43 as described in Weber et al., 2002, *Nat. Biotechnol.*, 20:901-907, the entire contents of which are herein incorporated by reference.

Example 3

Cell line construction. The random integration of the reporter gene as depicted in FIG. 1B was performed using Lipofectamine 2000 (Invitrogen) by co-transfecting 800 ng of the 5×TetO-pEF-H2B-Citrine reporter plasmid in CHO-K1 cells that do not carry the HAC. Cells were transferred from 24-well to 6-well plates 24 hours later and selected with 3 µg/ml puromycin for 12 days, starting 24 hours after the transfection. Single clones were obtained by limiting dilution. Subsequently, pEF-H2B-mCherry-T2A-rTet-EED was randomly integrated into these reporter lines by transfection with Lipofectamine 2000 (Invitrogen). These cells were selected using 300 µg/ml hygromycin starting 24 hours after transfection for a total of 12 days. Data shown herein is obtained using clone 3.

The reporter line as depicted in FIG. 1C was created by integrating the H2B-citrine reporter site-specifically in an artificial chromosome (MI-HAC) in CHO-K1 cells as described in Yamaguchi et al., 2011, supra. Since CHO-K1 cells form a monolayer with well-separated nuclei, they are amenable to long-term time-lapse imaging for up to ~5 days, allowing for characterization of silencing and reactivation events in single cells. In addition, they can be passaged for more than 30 days, allowing long-term measurements of epigenetic memory. The MI-HAC lacks endogenous genes, thus minimizing unknown interactions between our reporter and other genes. Moreover, the MI-HAC may be transferred to different cell lines by microcell-mediated chromosome transfer (MMCT) as described in Yamaguchi, et al., 2011, supra, allowing one to quantify the effect of cell type on the dynamics of silencing and reactivation, while maintaining a constant genetic context.

Integration of the reporter was performed by co-transfecting 600 ng PhiC31-Neo-ins-5×TetO-pEF-H2B-Citrine-ins reporter plasmid and 200 ng PhiC31 integrase plasmid, using Lipofectamine 2000 (Invitrogen). The transfection was performed in 24-well plates. Cells were transferred to 6-well plates 24 hours later and selected with 400 ng/ul geneticin for 12 days, starting 40 hours after the transfection. Single clones were obtained by limiting dilution. The integration of the reporter in the HAC was verified by genomic PCR, and a single clone was chosen for further analysis.

Each of the CR plasmids (pEF-H2B-mCherry-T2A-rTet-CR) was randomly integrated into this reporter line by transfection with Lipofectamine 2000 (Invitrogen). These cells were selected using 300 µg/ml zeocin starting 24 hours after transfection for a total of 12 days. Finally, single clones were selected for each CR by limiting dilution.

Example 4

Culture conditions. Cells were cultured at 37° C., in a humidified atmosphere with 5% CO2. For all experiments, the growth media consisted of Alpha MEM Earle's Salts (9144, Irvine Scientific) with 10% Tet Approved FBS (Clontech Laboratories) and 1× Penicillin/Streptomycin/L-glutamine (Life Technologies) added. Media containing the appropriate antibiotics (300 µg/ml neomycin and 300 µg/ml zeocin) were changed every 2-3 days during maintenance. During all recruitment and de-recruitment experiments, media without neomycin or zeocin were used and changed every 24 hours in all wells. Cells were harvested by rinsing with Dulbecco's Phosphate-Buffered Saline (DPBS, Life Technologies), and incubating at room temperature with 0.25% Trypsin (Life Technologies). For long-term storage, cells were frozen in growth media with 10% DMSO, placed at −80° C. (for up to a month), and then transferred to liquid nitrogen.

Example 5

Acquisition of time-lapse movies. Reporter cells expressing each of the four CRs were plated approximately 12 hours before imaging, at low density (1,500 cells/cm2) on glass-bottom plates (MatTek) coated with 5 µg/ml hamster fibronectin (Oxford Biomedical Research). Imaging was done using an inverted Olympus IX81 fluorescence microscope with Zero Drift Control (ZDC), a 20× dry objective, and an iKon-M CCD camera (Andor, Belfast, NIR). Fluorophores were excited using an X-Cite XLED1 light source (Lumen Dynamics). Images were automatically acquired every 20 minutes, using Metamorph software (Molecular Devices). The microscope was enclosed in a chamber kept at 37° C. and 5% CO2, and the imaging growth media (see Culture conditions) was changed daily. Silencing movies began with reporter cells actively expressing the reporter gene. Dox (1 µg/ml) was added to the cells at ~20 hours, after which imaging continued for at least 3 more days and until cell tracking became difficult due to high cell density. Cells were then re-plated at low density, in the presence of dox, for the subsequent acquisition of reactivation movies. Imaging began with these cells ~12 hours after re-plating, and dox was washed-out at ~20 hours into the movies (5 days since the beginning of dox addition).

Example 6

Analysis of time-lapse data and silencing event detection. Cells were segmented and tracked using the mCherry fluorescence signal with custom Matlab code (available upon request), as follows: (1) Initially, images were processed to correct for inhomogeneous fluorescent illumination by fitting a paraboloid to background (non-cell) pixel intensities, and then normalizing the image by this paraboloid. (2) An integrated segmentation and tracking procedure was used which combined (a) a pixel-based intensity threshold for segmentation, (b) a tracking algorithm based on global minimization of a cost function that incorporates cell positions and fluorescence intensities, and (c) heuristics that use discontinuities in tracking to correct segmentation. (3) Finally, all individual cell lineages were checked and corrected manually.

Using the contours obtained from this algorithm, total Citrine fluorescence levels were extracted for each of the cell lineages. Since the H2B-Citrine protein is stable, total fluorescence levels increased at a steady rate when the reporter was expressed at a constant level (FIG. 2A, '−dox'), but remained constant (flat) when the reporter gene was silenced. At each cell division, the total fluorescence signal was approximately halved as fluorescent protein molecules partitioned between daughter cells as described in Rosenfeld, et al., 2005, *Science*, 307:1962-1965, the entire contents of which are herein incorporated by reference. The fluorescence lost during these division events was computationally restored by computing the lost fluorescence and adding this constant value to all subsequent time points after a division event. This procedure, repeated for all division events, generated the cumulative total fluorescence traces (FIG. 2A, solid line), from which reporter production rates were assessed (slope of solid line in FIG. 2A).

Figure 7A:
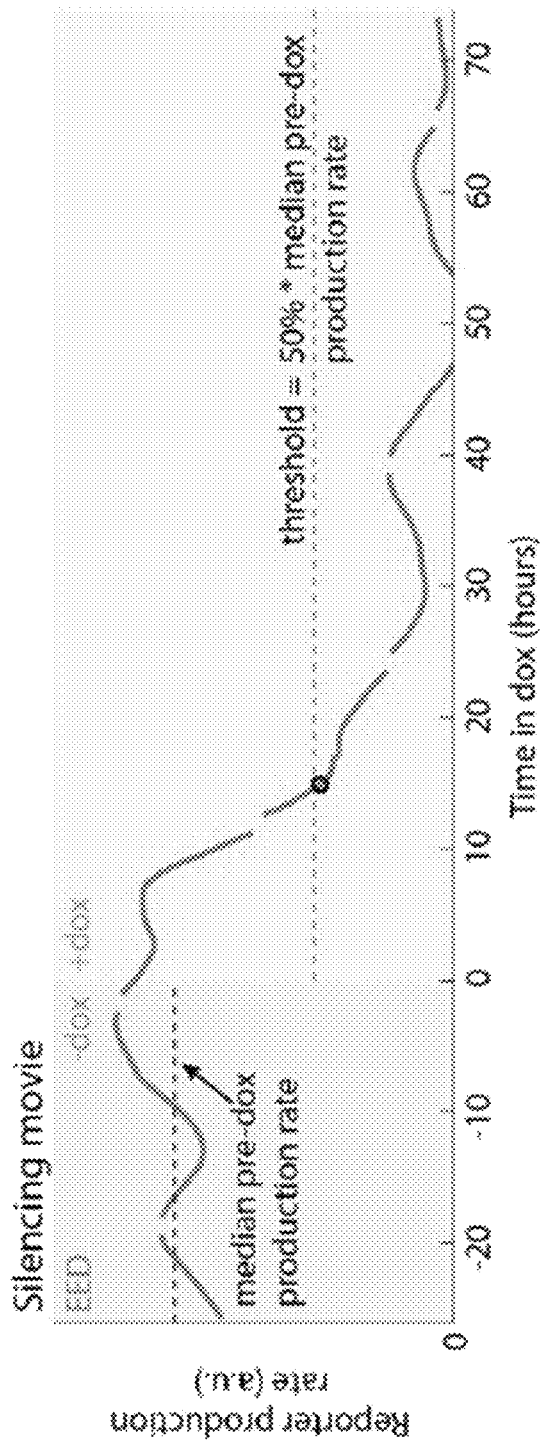
FIG. 7A is a graph of fluorescence tracing, according to embodiments of the present invention, for detection, specificity, and strength of silencing in which silence events were detected by setting a threshold on the reporter production rate, computed as the smoothed time derivative of the cumulative Citrine fluorescence trace (cyan curve, same cell lineage as in FIG. 2A), for which the frames immediately adjacent to cell division events were removed when the raw total fluorescence traces were processed to produce cumulative traces, resulting in gaps in the trace.

To detect silencing events, a threshold on reporter production rate was set for each individual lineage at 50% of its median before dox addition (FIG. 7A). To avoid misidentification of silencing events due to fluctuations in gene expression levels, a cell was marked silent when its reporter production rate dropped and remained below this threshold for at least 12 hours.

Reactivation events were identified when the reporter production rate of a silent cell increased beyond a global threshold, and remained above this threshold for at least 12 hours (FIG. 10A-10B). This global threshold was set at 50% of the median reporter production rate of all cells before the initial dox addition. The rationale for using a global threshold instead of a lineage-specific threshold for reactivation movies is that cells start these movies at zero production rate and in many cases do not reactivate during the movie. As a result, for many lineages, there is no natural lineage-specific threshold.

Example 7

ChIP-qPCR and MeDIP-qPCR. Each cell line was treated with dox (1 μg/ml) for 0, 3, 5, and 11 days before harvesting. ChIP and MeDIP were performed using LowCell #ChIP and MagMeDIP kits, respectively, with the Bioruptor sonicator (all from Diagenode). For ChIP, the following antibodies were used: anti-H3K27me3 (Milipore, 07-449), anti-H3K9me3 (Abcam, ab8898), anti-acetyl-H3 (Millipore, 06-599), anti-H3K4me3 (Abcam, ab8580). For MeDIP, the 5-methylcytidine antibody from the MagMeDIP kit (Diagenode) was used. qPCR was performed using SsoFast EvaGreen Supermix on a CFX96-C1000 Real-Time PCR System (both from Bio-Rad Laboratories). For qPCR primer sequences, see Table 1.

Reported fold-enrichment values from qPCR experiments used a standard $\Delta\Delta C_t$ method. Here, the threshold cycle number for amplification of a given locus in an experiment involving chromatin regulator CR was denoted as $C_t$ (locus, CR). In a first step, the data was normalized by an internal positive control locus for that particular modification, denoted $C_t$ (control, CR). Second, this value was normalized by the $\Delta C_t$ between the locus of interest and the control locus in the parental cell line without any CR:

$$\text{fold-change} = \frac{2^{\{C_t(locus,CR)-C_t(control,CR)\}}}{2^{\{C_t(locus,parental)-C_t(control,parental)\}}}$$

The internal control loci account for variations in the amount of DNA and pull-down efficiency for each sample. For this purpose β-actin was selected for the marks associated with active genes (H3K4me3 and histone acetylation) and Igf2 for the silencing marks (H3K27me3, H3K9me3, and 5mC). Igf2 was chosen for its lack of expression in mouse adult ovary cells (MGI Ref. ID J:46439) and elevated levels of H3K9me3 and H3K27me3 implicated in the imprinting of the locus as described in Li et al., 2008, Mol. Cel. Biol., 28:6473-6482, the entire contents of which are herein incorporated by reference.

Example 8

Flow cytometry for epigenetic memory analysis. For each cell line, cells were plated in multiple wells at the same time, and either treated with doxycycline (dox) at 1 μg/ml starting at different times (1, 2, 3, and 5 days before dox removal), or grown in the absence of dox (for background silencing correction). Dox was removed simultaneously from all samples. At different time points following dox removal, cells were harvested using 0.25% Trypsin (Life Technologies). A fraction of the cells (varying between one half to one tenth, depending on cell density) were re-plated for the next time point. The rest of the cells were resuspended in flow buffer (Hank's Balanced Salt Solution (Life Technology) and 2.5 mg/ml BSA), and filtered through 40 μm strainers (BD Falcon) to remove clumps. Cellular fluorescence distributions were measured with a MACSQuant VYB flow cytometer (Miltenyi Biotec, Bergisch Gladbach, Germany).

TABLE 1

| Locus | Name | Sequence |
| --- | --- | --- |
| pEF (promoter) | pEF_F_1013ChIP | SEQ ID NO: 1<br>ACGTATGTCGAGGTAGGCGT |
|  | pEF_R_1013ChIP | SEQ ID NO: 2<br>CTAGGCACCGGTTCAATTGC |
| citrine (gene body) | F_cit_Set2 | SEQ ID NO: 3<br>CGGCGACGTAAACGGCCACAAGTTCAG |
|  | R_cit_Set2 | SEQ ID NO: 4<br>CTTGCCGGTGGTGCAGATGAA |
| actin (control) | bActin F | SEQ ID NO: 5<br>ACTGGGACGATATGGAGAAG |
|  | bActin R | SEQ ID NO: 6<br>GGTCATCTTTTCACGGTTGG |
| Igf2 (control) | 5-42_Igf2_F | SEQ ID NO: 7<br>CTGTGGCCTGTAGGTCCTTG |
|  | 5-43_Igf2_R | SEQ ID NO: 8<br>CCTCTGCCTTTCCCTCTTGG |

The resulting data were analyzed with a custom Matlab program called EasyFlow (available upon request). Single cells were selected based on side and forward scatter properties, and only mCherry-expressing cells were analyzed. A manual gate was imposed on the Citrine fluorescence to determine the percent of silent cells for each sample (FIGS. 3C, 11A-11C). The gate was selected to contain 1-2% of the positive Citrine peak of untreated cells.

Example 9

Background silencing correction for long-term experiments. In all cell lines containing CRs, an increase in the percentage of silent cells over 30 days was observed, even in the absence of dox treatment (FIG. 11D). This background silencing is a combination of spontaneous silencing of the reporter locus (as seen in the parental line with no CRs, FIG. 11D), and non-specific silencing of the reporter by each rTet-CR fusion in the absence of dox (likely by dox-independent binding of rTetR to DNA). In order to correct for this background silencing, for each cell line, the fraction of cells silenced in the untreated line was subtracted and normalized by the fraction of untreated cells that were active at each time point. This allowed for the fraction of cells that were silenced specifically by CR recruitment to be obtained:

$$C_S(\text{background corrected}) = \frac{C_S(\text{dox treated}) - C_S(\text{untreated})}{C_A(\text{untreated})},$$

where $C_s(\text{dox treated})$ and $C_s(\text{untreated})$ are the fraction of cells silenced in the dox treated and untreated samples, respectively, and $C_A(\text{untreated})$ is the fraction of cells active in the untreated sample at the same time point.

Example 10

Extracting the transition rates. During EED and KRAB recruitment, using the model presented in FIG. 3A (upper panel), with an initial condition in which all cells are active, the exact solutions for the time evolution of the fraction of cells active ($C_A$), reversibly silent ($C_R$), and irreversibly silent ($C_I$) are:

$$C_A(t) = \frac{1}{\gamma_2 - \gamma_1}[(k_A + k_I - \gamma_1)e^{-\gamma_1 t} - (k_A + k_I - \gamma_2)e^{-\gamma_2 t}] \quad \text{(Eq. 1)}$$

$$C_R(t) = \frac{k_S}{\gamma_2 - \gamma_1}[e^{-\gamma_1 t} - e^{-\gamma_2 t}]$$

$$C_I(t) = \left[1 - \frac{k_S k_I}{\gamma_1(\gamma_2 - \gamma_1)}e^{-\gamma_1 t} + \frac{k_S k_I}{\gamma_2(\gamma_2 - \gamma_1)}e^{-\gamma_2 t}\right]$$

where $k_S$, $k_A$, and $k_I$ are the rates of silencing, reactivation, and irreversible commitment, respectively. The following was also defined:

$$\gamma_1 = \frac{k_S + k_A + k_I - \sqrt{(k_S + k_A + k_I)^2 - 4k_S k_I}}{2},$$

$$\gamma_2 = \frac{k_S + k_A + k_I - \sqrt{(k_S + k_A + k_I)^2 - 4k_S k_I}}{2}.$$

The total fraction of cells silent is the sum of cells that are reversibly and irreversibly (permanently) silent, which is denoted as:

$$C_S(t) = C_R(t) + C_I(t)$$

Additionally, during recruitment, a time lag was observed between dox addition and the onset of silencing, which we denote $T_{lag1}$. Therefore, for fitting purposes, in the equations above, t becomes $t - T_{lag1}$ for recruitment times larger than $T_{lag1}$. The fractions of silent/active cells were assumed to be constant before $T_{lag1}$.

During EED and KRAB release, it was assumed that the rates of silencing and irreversible commitment are negligible (FIG. 4A, lower panel). This means that the fraction of cells silent after CR release (dots in FIGS. 4C-4F) decays exponentially at a constant rate ($k_A$). More specifically, defining $C_S(t,\tau)$ as the fraction of cells silenced after a recruitment period of duration t, and release time $\tau$, is represented as:

$$C_S(t, \tau) = C_R(t) \cdot e^{-k_A(\tau - T_{lag\_2})} + C_I(t) \quad \text{(Eq. 2)}$$

where $C_R(t)$ and $C_I(t)$ are the fraction of cells in the R and I states, respectively, at the end of recruitment, and $T_{lag2}$ is the time lag before reactivation starts.

For EED and KRAB, the silencing and reactivation data at a given dox concentration were fit simultaneously using Equations 1 and 2 for silencing and reactivation phases, respectively. For maximum dox (1000 ng/ml), these data consist of the fraction of cells silent during recruitment (FIG. 2F), and the fraction of cells silent during release for all durations of recruitment (FIGS. 4C-4F). The "fit" function in MATLAB was used to perform a nonlinear least square fit with two independent parameters, t and τ, in order to extract $k_S$, $k_A$, $k_I$, $k_A$, $T_{lag\_1}$, and $T_{lag\_2}$. The fits are shown as solid lines in FIGS. 4C-4F and FIGS. 13A-13B. The values of the fitted parameters and their 95% confidence intervals for each dox concentration are plotted in FIGS. 4G-4I.

Note that during silencing at maximum recruitment strength, the rate of silencing ($k_S$) is much higher than the rates of reactivation ($k_A$) and irreversible commitment ($k_I$). Therefore, the fraction of silent cells over time during recruitment (dots in FIG. 2F) can be well-described using an exponential function that only depends on the rate of silencing ($k_S$):

$$C_S(t) = \begin{cases} 0, & \text{for } t < T_{lag\_1} \\ 1 - e^{-k_S(t - T_{lag\_s})}, & \text{for } t \geq T_{lag\_1} \end{cases},$$

where t is the recruitment duration, and $T_{lag\_1}$ is the time lag before the onset of silencing. The resulting fits using this approximation are plotted as solid lines in FIG. 2F.

During HDAC4 recruitment, the fraction of cells silent as a function of recruitment time is equal to the fraction of cells reversibly silent, since there is no irreversibly silent state:

$$C_S(t) = C_R(t) = \begin{cases} 0, & \text{for } t < T_{lag\_1} \\ \frac{k_S}{k_S + k_A}\left(1 - e^{-(k_S + k_A)(t - T_{lag\_1})}\right), & \text{for } t \geq T_{lag\_2} \end{cases}, \quad \text{(Eq. 3)}$$

During reactivation, for HDAC4, all cells that were reversibly silenced at the end of the recruitment period (t) reactivate at a constant rate ($k_A$):

$$C_S(t,\tau) = C_R(t) \cdot e^{-k_A \tau} \quad \text{(Eq. 4)}$$

The fraction of cells silent during recruitment and after release of HDAC4 were fit simultaneously with Equations 3 and 4 using nonlinear least square fitting in MATLAB to extract $k_S$, $k_A$, $T_{lag\_1}$, and their 95% confidence intervals.

For DNMT3B, the fraction of cells silent during recruitment is equal to the fraction of cells irreversibly silent (since we assume there is no reversible state), and increases with time as follows:

$$C_S(t) = C_I(t) = \begin{cases} 0, & \text{for } t < T_{lag\_1} \\ 1 - e^{-k_I(t - T_{lag\_1})}, & \text{for } t \geq T_{lag\_1} \end{cases} \quad \text{(Eq. 5)}$$

During release, the fraction of cells irreversibly silent is constant across all times post-dox ($\tau$), and only depends on the duration of recruitment, t:

$$C_S(t,\tau) = C_I(t) \quad \text{(Eq. 6)}$$

As with the other CRs, for DNMT3B the silencing and memory data was simultaneously fit with Equations 5 and 6 to determine a single $k_I$ and $T_{lag\_1}$, along with 95% confidence intervals.

At non-saturating dox concentration, for EED and DNMT3B, which silence slowly, the fraction of cells silenced during recruitment was measured only by flow cytometry. For KRAB and HDAC4, which silence fast, the fraction of cells silenced during recruitment at non-saturating dox concentrations were measured using time-lapse microscopy, as in FIG. A-2F.

Figure 15B:
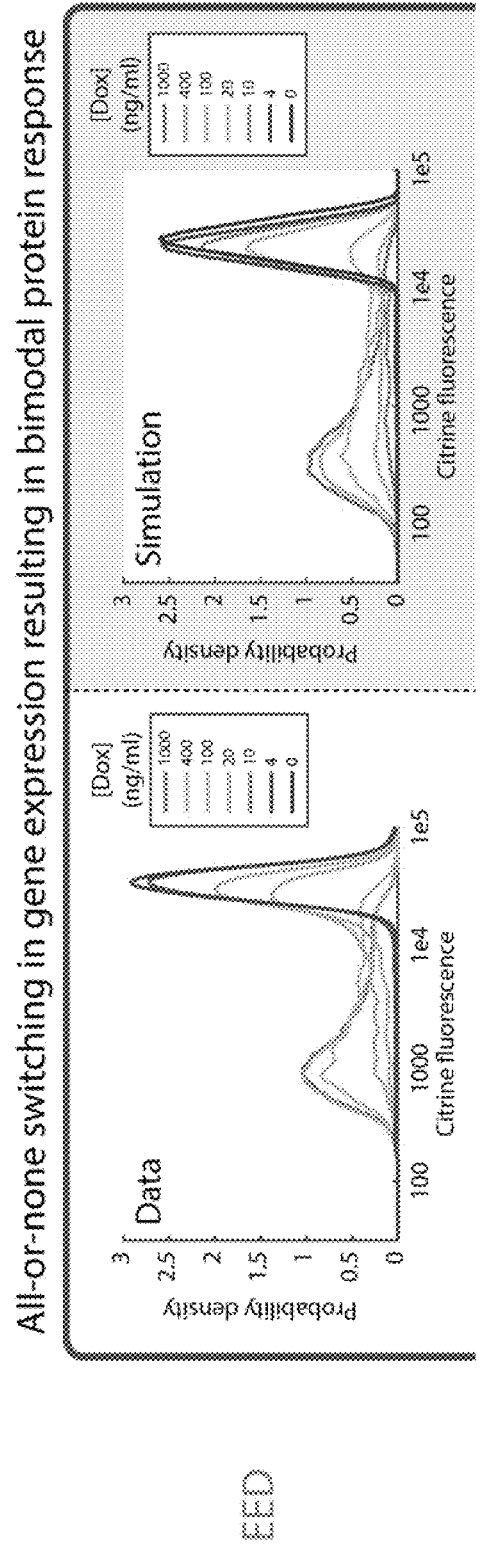
Figure 15C:
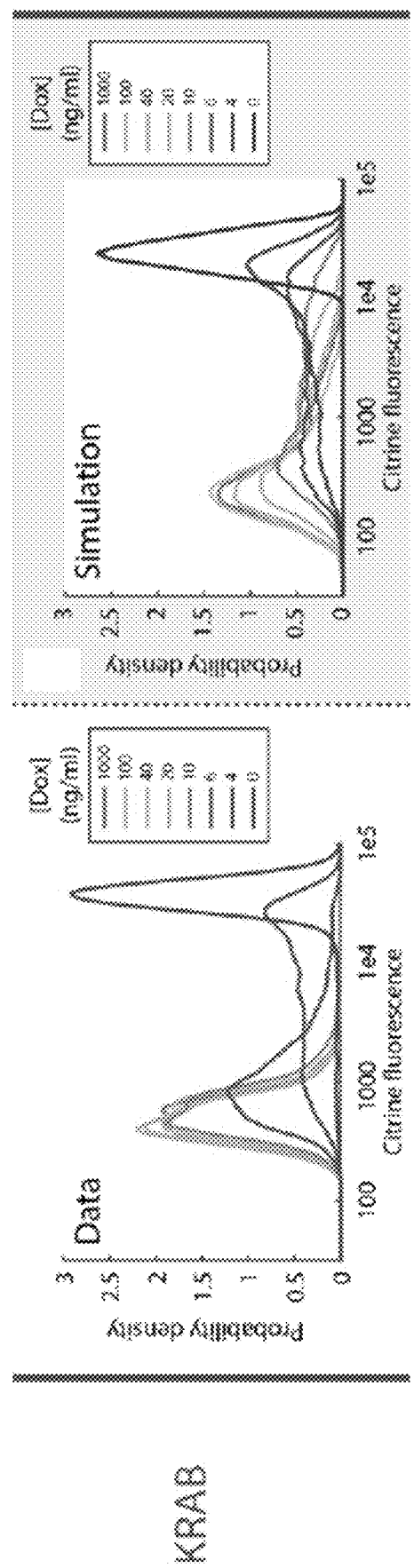
Figure 15D:
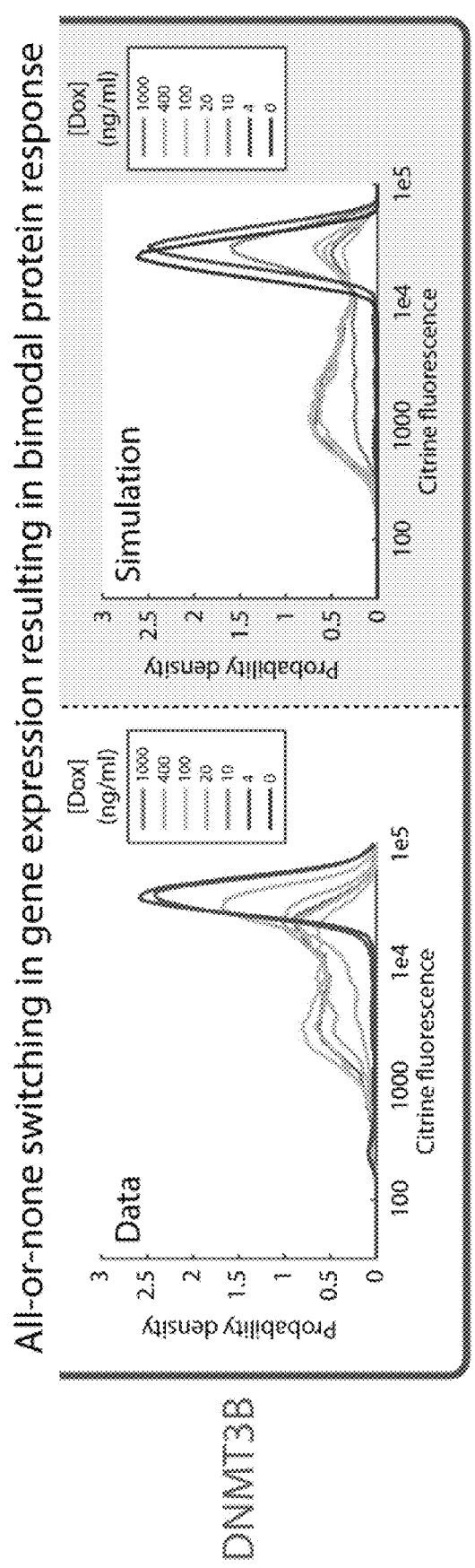
Figure 15E:
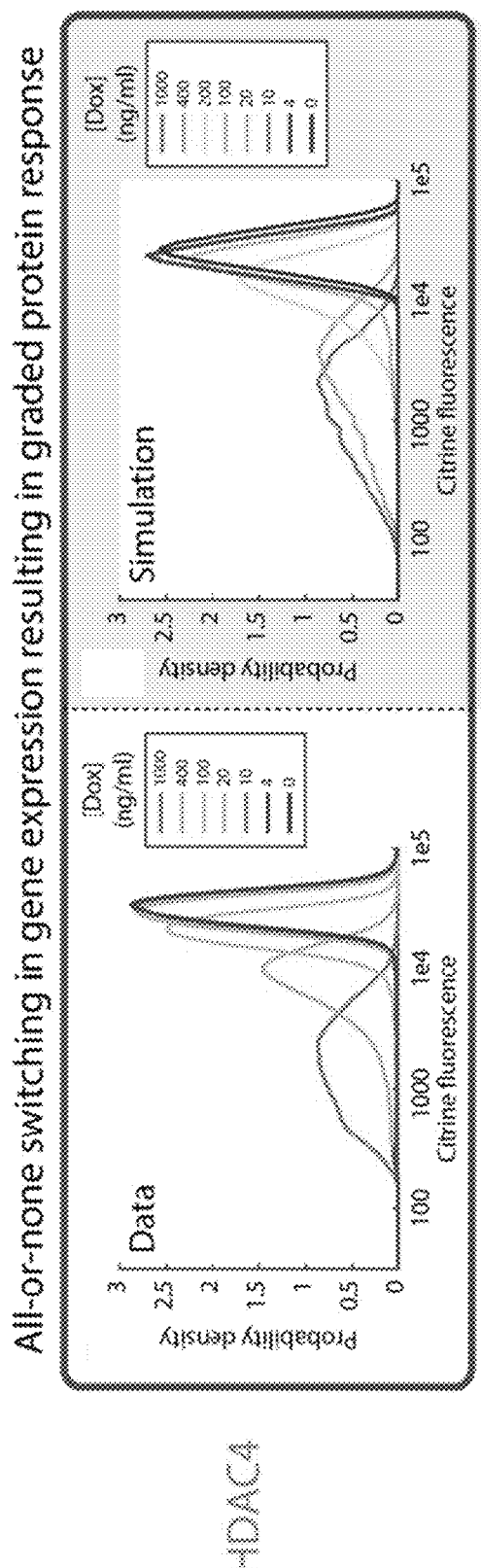
Figure 16A:
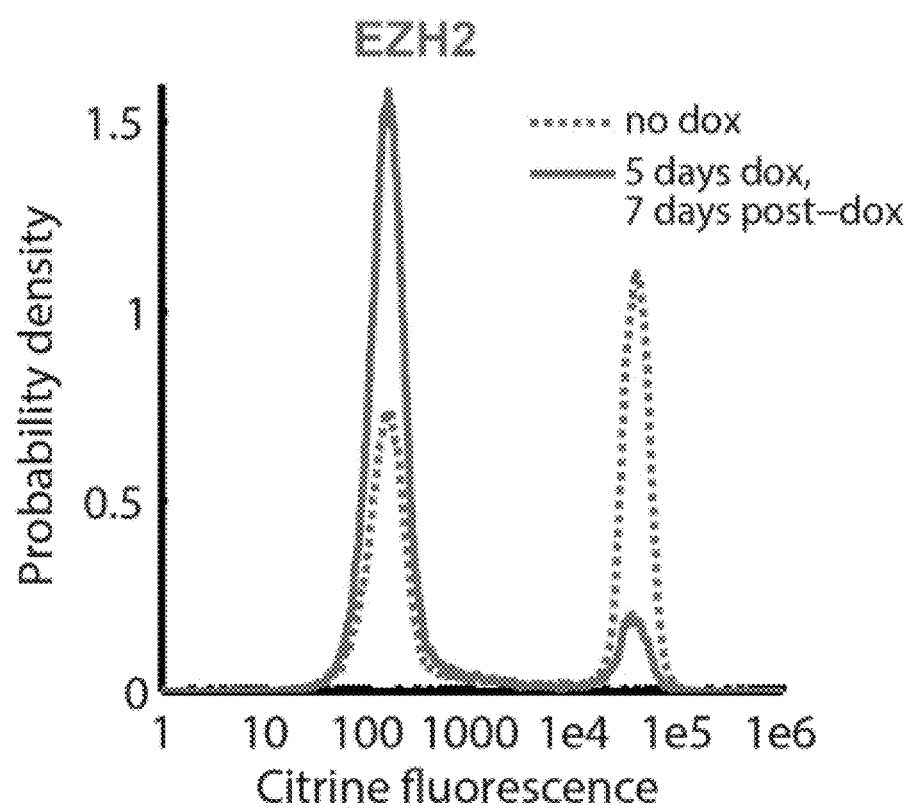
Figure 16B:
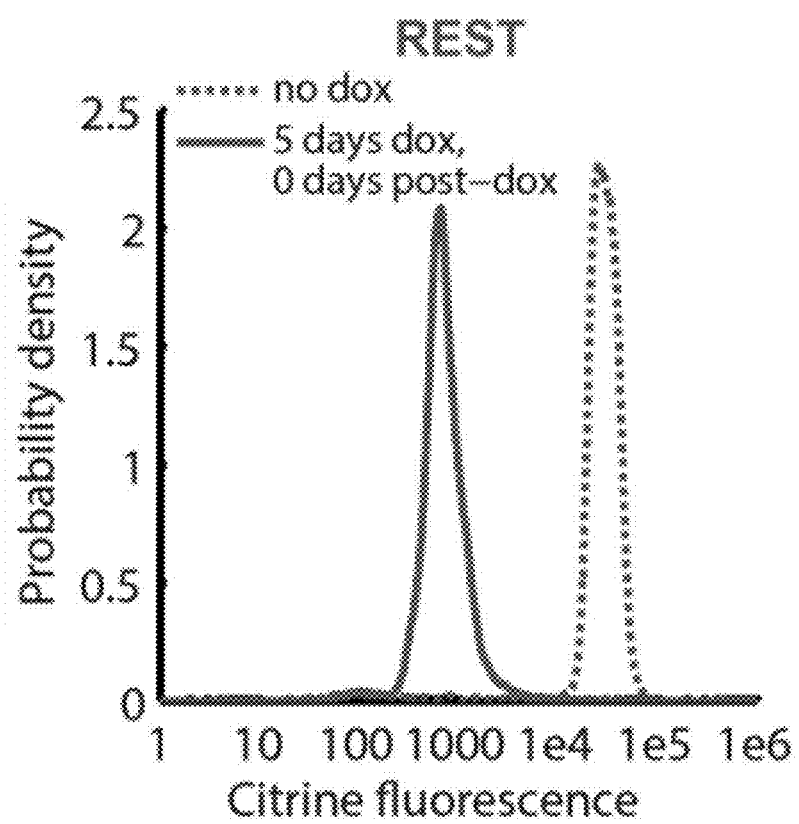
Figure 16C:
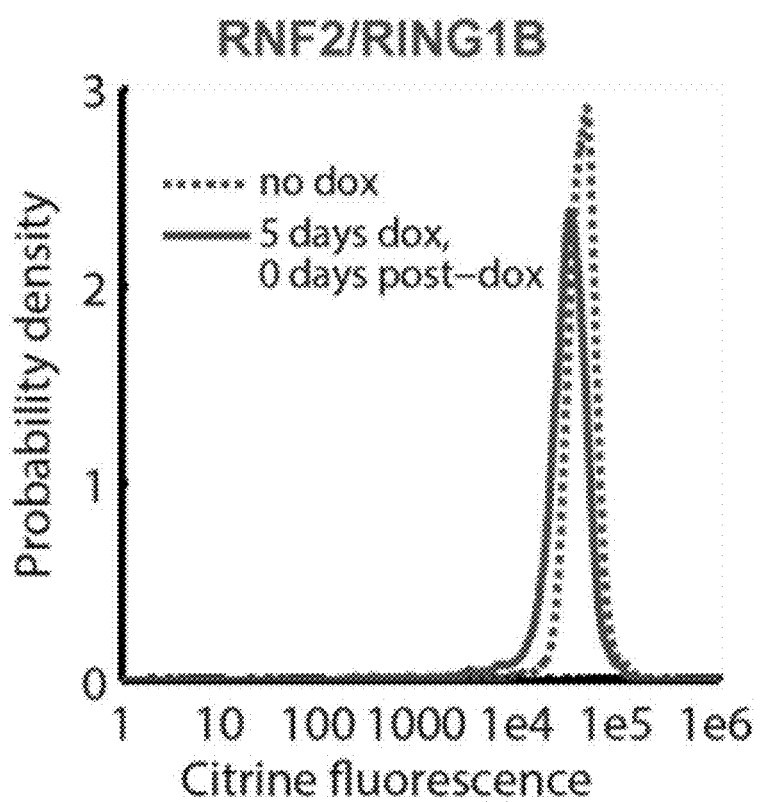
Figure 16D:
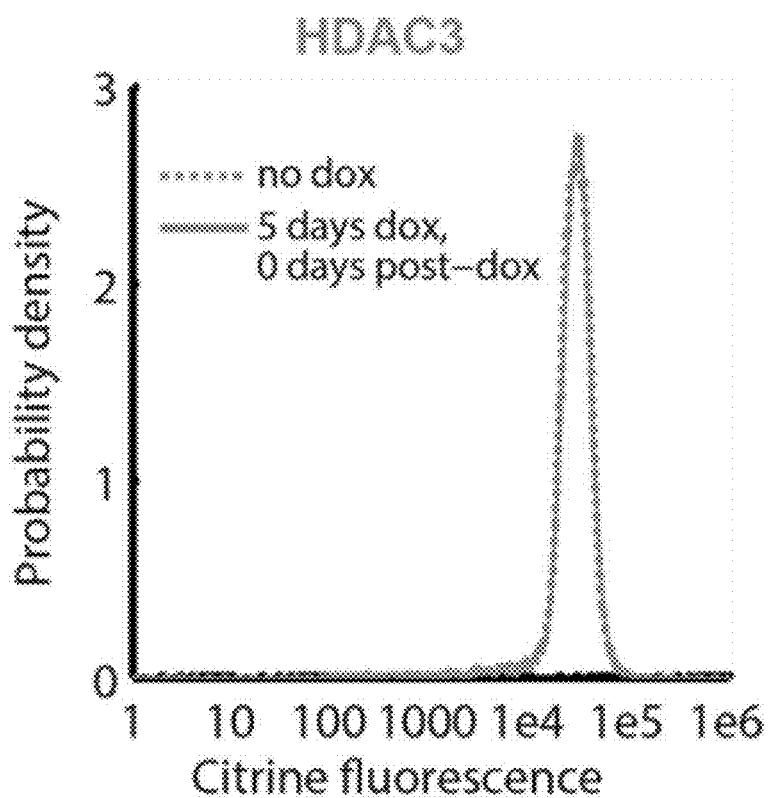

Based on the parameters measured here for CR-mediated silencing, EED, KRAB, and DNMT3B all operate in the slow switching regime that gives rise to bimodal protein distributions across various dox concentrations (FIG. 15B-15D). HDAC4 shows all-or-none stochastic silencing at strong recruitment strengths (saturating dox concentrations). However, as dox concentrations are decreased, the protein levels distributions shift in a graded manner (FIG. 15E).

To test if all-or-none silencing and reactivation at the chromatin level alone can recapitulate reporter protein distributions over various CRs and conditions, stochastic simulations were performed using the combined chromatin and transcription regulation model described in FIG. 15A. For these simulations we used the experimentally measured rates associated with chromatin-mediated gene switching—$k_S$, $k_A$, and $k_I$—for each CR across different dox concentrations (FIG. 3G-I). To simplify the simulation and limit the source of stochastic switching to the chromatin level, we consider the regime in which $k_{on} \gg k_{off}$. Under this approximation, the promoter is always active within the active chromatin state. The mRNA and protein production rates $\beta\_m$ (100 hr-1) and $\beta\_p$ (200 hr-1) are chosen such that the resulting mean H2B-Citrine fluorescence levels in the fully active state (without dox) from simulations match those obtained in flow cytometry experiments. We use the experimentally measured mRNA degradation rate $\gamma\_m = 0.1733$ hr-1 (corresponding to a half-live of 4 hours, as shown in FIG. 6B). The number of molecules for each mRNA and protein species is assumed to be halved at every cell division (dilution). Since H2B-citrine is stable, the protein degradation is set to zero. Lastly, each simulated cell has its cell cycle length drawn randomly from a normal distribution with mean and variance derived from those empirically observed in movie experiments.

Stochastic simulation of the model in this regime recapitulated bimodal responses of EED, KRAB and DNMT3B (FIGS. 15B-15D, simulation graphs), reflecting the fact the lifetime of the silent state remains longer than the protein and mRNA lifetimes, regardless of dox concentrations. The model also recapitulated the graded response of HDAC4 observed at sub-saturating dox concentrations (FIG. 15E, simulation graph), reflecting the fact that in these conditions $k_S$ and $k_A$ are similar, resulting in lifetimes of the silent state that are on the order of protein dilution (i.e. cell division time). Together, these results demonstrate how a stochastic, all-or-none model of chromatin-mediated silencing and reactivation is sufficient to explain the protein distributions obtained for the CRs as disclosed herein.

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A method of controlling a fraction of a population of single cells having a silencing and reactivation characteristic of a target gene, wherein the population of single cells each comprise the target gene, the method comprising:
identifying a desired silencing and reactivation characteristic of the target gene in the population of single cells;
selecting a chromatin regulator (CR) protein to be:
HDAC4 if the desired silencing and reactivation characteristic comprises reversible silencing, wherein the reversible silencing corresponds to a rate constant from a reversible silent state to an active state of about 0.76 d$^{-1}$, EED or KRAB if the desired silencing and reactivation characteristic comprises partial committing to silencing, wherein the partial committing to silencing corresponds to a rate constant from a reversible silent state to an irreversible silent state of about 0.09 d$^{-1}$ to about 0.13 d$^{-1}$, or DNMT3B if the desired silencing and reactivation characteristic comprises irreversible silencing, the irreversible silencing corresponds to a rate constant from an active state to an irreversible silent state of about 0.38 d$^{-1}$;

expressing a CR fusion protein comprising the selected CR protein fused to a deoxyribonucleic acid (DNA) binding domain protein in the population of single cells, wherein the CR fusion protein is capable of binding to a site proximal to a transcription initiation site of the target gene in the population of single cells in the presence of an inducer; and regulating the recruitment strength of the CR fusion protein by increasing or decreasing the concentration of the inducer, thereby increasing or decreasing the fraction of the population of single cells having the desired silencing and reactivation characteristic of the target gene.

2. The method of claim 1, wherein the DNA binding domain protein is selected from the group consisting of a tetracycline repressor (TetR) protein, a lactose inhibitor (LacI) protein, a Gal4 protein, a dead Cas9 (dCas9) protein, a transcription activator-like effector (TALE) protein, and a zinc finger protein.

3. The method of claim 1, wherein the DNA binding domain protein is a reverse TetR (rTetR).

4. The method of claim 1, wherein the site proximal to the transcription initiation site is at or within 5,000 basepairs upstream or downstream of the transcription initiation site of the target gene.

5. The method of claim 1, wherein the target gene encodes for a protein, a peptide, or a ribonucleic acid (RNA).

6. The method of claim 5, wherein the RNA is selected from the group consisting of a messenger RNA (mRNA), a long noncoding RNA (lncRNA), and an interfering RNA (RNAi).

7. The method of claim 1, wherein the site proximal to the transcription initiation site is at or within 3,000 basepairs upstream or downstream of the transcription initiation site of the target gene.

8. The method of claim 1, wherein the desired silencing and reactivation characteristic of the target gene occurs in an all-or-none fashion in single cells of the population of single cells.

9. The method of claim 1, wherein the desired silencing and reactivation characteristic comprises reversible silencing, and wherein said selecting comprises selecting the CR protein to be HDAC4.

10. The method of claim 1, wherein the reversible silencing corresponds to a rate constant from an active state to a reversible silent state of about 8.6 d$^{-1}$.

11. The method of claim 1, wherein the desired silencing and reactivation characteristic comprises partial committing to silencing, and wherein said selecting comprises selecting the CR protein to be EED.

12. The method of claim 1, wherein the partial committing to silencing comprises a rate constant from an active state to a reversible silent state of about 0.9 d$^{-1}$.

13. The method of claim 1, wherein the desired silencing and reactivation characteristic comprises partial committing to silencing, and wherein said selecting comprises selecting the CR protein to be KRAB.

14. The method of claim 1, wherein the partial committing to silencing comprises a rate constant from an active state to a reversible silent state of about 11 d$^{-1}$.

15. The method of claim 1, wherein the desired silencing and reactivation characteristic comprises irreversible silencing, and wherein said selecting comprises selecting the CR protein to be DNMT3B.

16. The method of claim 1, wherein the DNA binding protein is reverse TetR and the inducer is tetracycline or doxycycline.

17. The method of claim 1, further comprising releasing the binding of the CR fusion protein from the site proximal to the transcription initiation site of the target gene in the population of single cells by removing the inducer.

* * * * *